US012398209B2

(12) United States Patent
Attiyeh et al.

(10) Patent No.: US 12,398,209 B2
(45) Date of Patent: *Aug. 26, 2025

(54) METHODS OF TREATING CANCERS WITH ANTAGONISTIC ANTI-PD-1 ANTIBODIES

(71) Applicant: Janssen Biotech, Inc., Horsham, PA (US)

(72) Inventors: Edward Attiyeh, Villanova, PA (US); Kyounghwa Bae, Spring House, PA (US); James G. Greger, Wayne, PA (US); Christina Lourdes Mayer, Dallas, TX (US); Hong Xie, Dresher, PA (US)

(73) Assignee: Janssen Biotech, Inc., Horsham, PA (US)

( * ) Notice: Subject to any disclaimer, the term of this patent is extended or adjusted under 35 U.S.C. 154(b) by 606 days.

This patent is subject to a terminal disclaimer.

(21) Appl. No.: 16/252,295

(22) Filed: Jan. 18, 2019

(65) Prior Publication Data

US 2019/0225689 A1    Jul. 25, 2019

Related U.S. Application Data

(60) Provisional application No. 62/794,195, filed on Jan. 18, 2019, provisional application No. 62/620,106, filed on Jan. 22, 2018.

(51) Int. Cl.
*C07K 16/28* (2006.01)
*A61K 39/00* (2006.01)
*A61P 35/00* (2006.01)

(52) U.S. Cl.
CPC .......... *C07K 16/2818* (2013.01); *A61P 35/00* (2018.01); *A61K 2039/505* (2013.01); *A61K 2039/545* (2013.01); *C07K 2317/76* (2013.01)

(58) Field of Classification Search
CPC ..................... C07K 16/2818; A61K 2039/545
See application file for complete search history.

(56) References Cited

U.S. PATENT DOCUMENTS

| | | |
|---|---|---|
| 4,683,195 A | 7/1987 | Mullis et al. |
| 4,978,672 A | 12/1990 | Bowman et al. |
| 5,208,020 A | 5/1993 | Chari et al. |
| 5,223,409 A | 6/1993 | Ladner et al. |
| 5,225,539 A | 7/1993 | Winter |
| 5,403,484 A | 4/1995 | Ladner et al. |
| 5,416,064 A | 5/1995 | Chari et al. |
| 5,427,908 A | 6/1995 | Dower et al. |
| 5,571,698 A | 11/1996 | Ladner et al. |
| 5,580,717 A | 12/1996 | Dower et al. |
| 5,624,821 A | 4/1997 | Winter et al. |
| 5,635,483 A | 6/1997 | Pettit et al. |
| 5,688,690 A | 11/1997 | Valiante et al. |
| 5,712,374 A | 1/1998 | Kuntsmann et al. |
| 5,714,586 A | 2/1998 | Kunstmann et al. |
| 5,739,116 A | 4/1998 | Hamann et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,877,296 A | 3/1999 | Hamann et al. |
| 5,885,793 A | 3/1999 | Griffiths et al. |
| 5,897,862 A | 4/1999 | Hardy et al. |
| 5,969,108 A | 10/1999 | McCafferty et al. |
| 6,054,297 A | 4/2000 | Carter et al. |
| 6,150,584 A | 11/2000 | Kucherlapati et al. |
| 6,172,197 B1 | 1/2001 | McCafferty et al. |
| 6,180,370 B1 | 1/2001 | Queen et al. |
| 6,303,121 B1 | 10/2001 | Kwon |
| 6,479,638 B1 | 11/2002 | Adema et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,582,959 B2 | 6/2003 | Kim |
| 6,593,081 B1 | 7/2003 | Griffiths et al. |
| 6,630,579 B2 | 10/2003 | Chari et al. |
| 6,703,020 B1 | 3/2004 | Thorpe et al. |
| 6,737,056 B1 | 5/2004 | Presta |
| 6,818,749 B1 | 11/2004 | Kashmiri et al. |
| 6,884,879 B1 | 4/2005 | Baca et al. |
| 7,025,962 B1 | 4/2006 | Gorman |
| 7,029,674 B2 | 4/2006 | Carreno et al. |
| 7,060,269 B1 | 6/2006 | Baca et al. |
| 7,138,500 B1 | 11/2006 | Goodwin |
| 7,288,251 B2 | 10/2007 | Bedian |
| 7,288,638 B2 | 10/2007 | Jure-kunkel |
| 7,473,761 B2 | 1/2009 | Albert et al. |
| 7,479,544 B2 | 1/2009 | Clark et al. |

(Continued)

FOREIGN PATENT DOCUMENTS

| | | |
|---|---|---|
| AU | 2016348388 A1 | 5/2018 |
| AU | 2016348391 A1 | 5/2018 |

(Continued)

OTHER PUBLICATIONS

Wang et al., J Clin Pharmacol 49:1012-24 (Year: 2009).*
Blank et al., "Interaction of PD-L1 on tumor cells with PD-1 on tumor-specific T cells as a mechanism of immune evasion: implications for tumor immunotherapy.", Cancer Immunol Immunother, 2005, pp. 307-314, vol. 54.
Bolt et al., "The generation of a humanized, non-mitogenic CD3 monoclonal antibody which retains in vitro immunosuppressive properties*.", Eur J Immunol, 1993, pp. 403-411, vol. 23.

(Continued)

*Primary Examiner* — Jessica H Roark

(57) ABSTRACT

The present invention relates to methods of treating cancers with antagonistic anti-PD-1 antibodies, formulations of the antagonistic anti-PD-1 antibodies and drug products of the anti-PD-1 antibodies.

34 Claims, 4 Drawing Sheets

Specification includes a Sequence Listing.

(56) References Cited

U.S. PATENT DOCUMENTS

| | | |
|---|---|---|
| 7,488,802 B2 | 2/2009 | Collins et al. |
| 7,498,298 B2 | 3/2009 | Doronina et al. |
| 7,595,048 B2 | 9/2009 | Honjo et al. |
| 7,618,632 B2 | 11/2009 | Collins |
| 7,708,996 B2 | 5/2010 | Yu |
| 7,709,226 B2 | 5/2010 | Foote |
| 7,867,493 B2 | 1/2011 | Damiano et al. |
| 7,888,477 B2 | 2/2011 | Bangur et al. |
| 7,931,896 B2 | 4/2011 | Chen |
| 7,943,743 B2 | 5/2011 | Korman et al. |
| 7,960,515 B2 | 6/2011 | Min |
| 8,008,449 B2 | 8/2011 | Korman et al. |
| 8,034,953 B2 | 10/2011 | Combs et al. |
| 8,080,636 B2 | 12/2011 | Mikesell et al. |
| 8,101,719 B2 | 1/2012 | Kikuchi et al. |
| 8,133,983 B2 | 3/2012 | Bakker |
| 8,168,757 B2 | 5/2012 | Finnefrock et al. |
| 8,188,232 B1 | 5/2012 | Murphy et al. |
| 8,188,238 B2 | 5/2012 | Pease et al. |
| 8,242,247 B2 | 8/2012 | Klein et al. |
| 8,247,537 B2 | 8/2012 | Korman et al. |
| 8,303,955 B2 | 11/2012 | Presta |
| 8,354,509 B2 | 1/2013 | Carven et al. |
| 8,388,967 B2 | 3/2013 | Smith |
| 8,415,355 B2 | 4/2013 | Brain et al. |
| 8,546,541 B2 | 10/2013 | Murphy et al. |
| 8,552,002 B2 | 10/2013 | Ding et al. |
| 8,552,003 B2 | 10/2013 | Charest et al. |
| 8,563,694 B2 | 10/2013 | Mataraza et al. |
| 8,586,023 B2 | 11/2013 | Shiku |
| 8,591,886 B2 | 11/2013 | Ponath |
| 8,598,322 B2 | 12/2013 | Markel et al. |
| 8,609,816 B2 | 12/2013 | Korman et al. |
| 8,617,546 B2 | 12/2013 | Kang et al. |
| 8,685,980 B2 | 4/2014 | Besong et al. |
| 8,716,452 B2 | 5/2014 | Jure-kunkel |
| 8,728,474 B2 | 5/2014 | Honjo et al. |
| 8,735,553 B1 | 5/2014 | Li et al. |
| 8,748,356 B2 | 6/2014 | Raghunathan |
| 8,821,867 B2 | 9/2014 | Ahrens |
| 8,961,967 B2 | 2/2015 | Strohl et al. |
| 8,993,731 B2 | 3/2015 | Tyson |
| 9,102,727 B2 | 8/2015 | Freeman et al. |
| 9,163,087 B2 | 10/2015 | Kuchroo et al. |
| 9,181,342 B2 | 11/2015 | Davis |
| 9,220,776 B2 | 12/2015 | Sharma et al. |
| 9,243,052 B2 | 1/2016 | Olive et al. |
| 9,387,247 B2 | 7/2016 | Korman et al. |
| 9,457,080 B2 | 10/2016 | Freeman et al. |
| 9,676,853 B2 | 6/2017 | Zhou et al. |
| 9,683,043 B2 | 6/2017 | Davis et al. |
| 9,683,048 B2 | 6/2017 | Freeman et al. |
| 9,771,425 B2 | 9/2017 | Wang et al. |
| 9,815,897 B2 | 11/2017 | King et al. |
| 9,856,320 B2 | 1/2018 | Cogswell et al. |
| 9,914,783 B1 | 3/2018 | Afar et al. |
| 9,982,053 B2 | 5/2018 | Pantaleo et al. |
| 9,987,500 B2 | 6/2018 | Papadopoulos et al. |
| 10,160,806 B2 | 12/2018 | Bonvini et al. |
| 10,894,830 B2* | 1/2021 | Verona .............. C07K 16/2803 |
| 11,021,543 B2* | 6/2021 | Ahmadi .............. A61K 31/573 |
| 2002/0068276 A1 | 6/2002 | Winter et al. |
| 2002/0160000 A1 | 10/2002 | Wood et al. |
| 2003/0040044 A1 | 2/2003 | Heavner et al. |
| 2003/0079253 A1 | 4/2003 | Hiatt et al. |
| 2003/0096977 A1 | 5/2003 | Koike et al. |
| 2003/0103976 A1 | 6/2003 | Serizawa et al. |
| 2003/0190317 A1 | 10/2003 | Baca et al. |
| 2003/0203409 A1 | 10/2003 | Kim |
| 2003/0206899 A1 | 11/2003 | Ferrara et al. |
| 2003/0226155 A1 | 12/2003 | Sadeghi et al. |
| 2004/0047858 A1 | 3/2004 | Blumberg et al. |
| 2004/0133357 A1 | 7/2004 | Zhong et al. |
| 2004/0137513 A1 | 7/2004 | Devaux et al. |
| 2004/0166544 A1 | 8/2004 | Morton et al. |
| 2004/0208807 A1 | 10/2004 | Soderstrom |
| 2004/0208887 A1 | 10/2004 | Drakenberg et al. |
| 2005/0009136 A1 | 1/2005 | Nixon et al. |
| 2005/0025763 A1 | 2/2005 | Williams et al. |
| 2005/0112126 A1 | 5/2005 | Baca et al. |
| 2005/0186208 A1 | 8/2005 | Fyfe et al. |
| 2005/0215770 A1 | 9/2005 | Bell et al. |
| 2006/0009360 A1 | 1/2006 | Pifer et al. |
| 2006/0014768 A1 | 1/2006 | Kawasaki et al. |
| 2006/0034834 A1 | 2/2006 | Marasco et al. |
| 2006/0110383 A1 | 5/2006 | Hongo et al. |
| 2006/0167015 A1 | 7/2006 | Brietenstein et al. |
| 2006/0222645 A1 | 10/2006 | Lee et al. |
| 2006/0241106 A1 | 10/2006 | Drysdale et al. |
| 2006/0263361 A1 | 11/2006 | Moretta et al. |
| 2007/0014796 A1 | 1/2007 | Carr |
| 2007/0020267 A1 | 1/2007 | Fuh et al. |
| 2007/0036783 A1 | 2/2007 | Humeau et al. |
| 2007/0048315 A1 | 3/2007 | Presta |
| 2007/0048740 A1 | 3/2007 | Isogai et al. |
| 2007/0083334 A1 | 4/2007 | Mintz et al. |
| 2007/0104715 A1 | 5/2007 | Nordstedt et al. |
| 2007/0141065 A1 | 6/2007 | Fuh et al. |
| 2007/0248801 A1 | 10/2007 | Nakao |
| 2007/0287170 A1 | 12/2007 | Davis et al. |
| 2008/0166352 A1 | 7/2008 | Siu et al. |
| 2008/0194579 A1 | 8/2008 | Garcia-Echeverria et al. |
| 2008/0275067 A1 | 11/2008 | Fowler et al. |
| 2009/0055944 A1 | 2/2009 | Korman et al. |
| 2009/0110686 A1 | 4/2009 | Auer |
| 2009/0118127 A1 | 5/2009 | Raghunathan |
| 2009/0136490 A1 | 5/2009 | Pilkington et al. |
| 2009/0182127 A1 | 7/2009 | Kjaergaard et al. |
| 2009/0217401 A1 | 8/2009 | Korman et al. |
| 2009/0220485 A1 | 9/2009 | Tanha |
| 2010/0004269 A1 | 1/2010 | Price et al. |
| 2010/0011456 A1 | 1/2010 | Mathur et al. |
| 2010/0015133 A1 | 1/2010 | Igawa et al. |
| 2010/0021477 A1 | 1/2010 | Tsui et al. |
| 2010/0028637 A1 | 2/2010 | Tavsanli et al. |
| 2010/0105711 A1 | 4/2010 | Fairhurst et al. |
| 2010/0119516 A1 | 5/2010 | Wu |
| 2010/0150902 A1 | 6/2010 | Haeuw |
| 2010/0249126 A1 | 9/2010 | Burger et al. |
| 2010/0260754 A1 | 10/2010 | Chedid et al. |
| 2010/0261620 A1 | 10/2010 | Almagro et al. |
| 2011/0008369 A1 | 1/2011 | Finnefrock et al. |
| 2011/0027284 A1 | 2/2011 | Barske et al. |
| 2011/0077268 A1 | 3/2011 | Liu et al. |
| 2011/0112063 A1 | 5/2011 | Marsilje et al. |
| 2011/0123532 A1 | 5/2011 | Gurney et al. |
| 2011/0150870 A1 | 6/2011 | Rader |
| 2011/0150892 A1 | 6/2011 | Thudium et al. |
| 2011/0172228 A1 | 7/2011 | Ren et al. |
| 2011/0230444 A1 | 9/2011 | Garcia-Echeverria et al. |
| 2011/0237573 A1 | 9/2011 | Cheng et al. |
| 2011/0271358 A1 | 11/2011 | Freeman et al. |
| 2011/0280866 A1 | 11/2011 | Didierlaurent et al. |
| 2011/0281866 A1 | 11/2011 | Ren et al. |
| 2012/0017292 A1 | 1/2012 | Kovalic et al. |
| 2012/0039906 A1 | 2/2012 | Olive |
| 2012/0045437 A1 | 2/2012 | Ma et al. |
| 2012/0100158 A1 | 4/2012 | Markel et al. |
| 2012/0108795 A1 | 5/2012 | Kehoe et al. |
| 2012/0114652 A1 | 5/2012 | Elvin et al. |
| 2012/0149876 A1 | 6/2012 | Von Kreudenstein et al. |
| 2012/0189617 A1 | 7/2012 | Takayangi et al. |
| 2012/0237522 A1 | 9/2012 | Chang et al. |
| 2013/0034559 A1 | 2/2013 | Queva et al. |
| 2013/0039913 A1 | 2/2013 | Labrijn et al. |
| 2013/0045202 A1 | 2/2013 | Irving et al. |
| 2013/0149301 A1 | 6/2013 | Meade |
| 2013/0150342 A1 | 6/2013 | Brain et al. |
| 2013/0156774 A1 | 6/2013 | Kuchroo et al. |
| 2013/0186797 A1 | 7/2013 | Walsh et al. |
| 2013/0195849 A1 | 8/2013 | Von Kreudenstein et al. |
| 2013/0280275 A1 | 10/2013 | Liu |
| 2013/0281022 A1 | 10/2013 | Mahany et al. |
| 2013/0281922 A1 | 10/2013 | Teige |

(56) References Cited

U.S. PATENT DOCUMENTS

| | | |
|---|---|---|
| 2013/0336976 A1 | 12/2013 | Glennie |
| 2014/0011798 A1 | 1/2014 | Furet et al. |
| 2014/0037551 A1 | 2/2014 | Zang et al. |
| 2014/0044738 A1 | 2/2014 | Langermann et al. |
| 2014/0056890 A1 | 2/2014 | Gurney et al. |
| 2014/0112915 A1 | 4/2014 | Bardroff et al. |
| 2014/0141000 A1 | 5/2014 | Chiu et al. |
| 2014/0271618 A1 | 9/2014 | Markel et al. |
| 2014/0271629 A1 | 9/2014 | Corbit et al. |
| 2014/0273092 A1 | 9/2014 | Flikweert et al. |
| 2014/0294765 A1 | 10/2014 | Cojocaru et al. |
| 2014/0294852 A1 | 10/2014 | Korman et al. |
| 2014/0294860 A1 | 10/2014 | Platten et al. |
| 2014/0322218 A1 | 10/2014 | Xiao et al. |
| 2014/0341902 A1 | 11/2014 | Maecker et al. |
| 2015/0126485 A1 | 5/2015 | Furet et al. |
| 2015/0141427 A1 | 5/2015 | Furet et al. |
| 2015/0165025 A1 | 6/2015 | Korman et al. |
| 2015/0183801 A1 | 7/2015 | Furet et al. |
| 2015/0183874 A1 | 7/2015 | Liu et al. |
| 2015/0197505 A1 | 7/2015 | Lelais et al. |
| 2015/0216970 A1 | 8/2015 | Grogan et al. |
| 2015/0218274 A1 | 8/2015 | Sabatos-Peyton et al. |
| 2015/0259434 A1 | 9/2015 | Johnson et al. |
| 2015/0315275 A1 | 11/2015 | Langermann et al. |
| 2015/0353636 A1 | 12/2015 | Parren et al. |
| 2016/0017040 A1 | 1/2016 | Leong et al. |
| 2016/0032014 A1 | 2/2016 | Michaels et al. |
| 2016/0122707 A1 | 5/2016 | Swee et al. |
| 2016/0159905 A1 | 6/2016 | Abdiche et al. |
| 2016/0168236 A1 | 6/2016 | Shipp et al. |
| 2016/0222113 A1 | 8/2016 | Buchanan et al. |
| 2016/0251436 A1 | 9/2016 | Amirina et al. |
| 2016/0272708 A1 | 9/2016 | Chen |
| 2016/0311902 A1 | 10/2016 | Morsey et al. |
| 2016/0376367 A1 | 12/2016 | Yuan et al. |
| 2016/0376373 A1* | 12/2016 | Ahmadi .................. A61K 45/06 424/136.1 |
| 2017/0044259 A1 | 2/2017 | Tipton et al. |
| 2017/0044260 A1 | 2/2017 | Baruah et al. |
| 2017/0044265 A1 | 2/2017 | Ahmadi |
| 2017/0081409 A1 | 3/2017 | Dijk et al. |
| 2017/0088612 A1 | 3/2017 | Bigal |
| 2017/0088618 A1 | 3/2017 | Bennett et al. |
| 2017/0114135 A1 | 4/2017 | Codarri-Deak et al. |
| 2017/0121409 A1 | 5/2017 | Verona et al. |
| 2017/0137520 A1 | 5/2017 | Punnonen et al. |
| 2017/0145116 A1 | 5/2017 | Regula et al. |
| 2017/0158764 A1 | 6/2017 | Mizuno et al. |
| 2017/0166642 A1 | 6/2017 | Pantaleo et al. |
| 2017/0240644 A1 | 8/2017 | Zhou et al. |
| 2017/0247454 A1 | 8/2017 | Benz et al. |
| 2017/0267762 A1 | 9/2017 | Qiu et al. |
| 2017/0327560 A1 | 11/2017 | Armstrong et al. |
| 2018/0127502 A1 | 5/2018 | Brentjens et al. |
| 2018/0142022 A1 | 5/2018 | Yam et al. |
| 2018/0155429 A1* | 6/2018 | Finckenstein .... G01N 33/57423 |
| 2018/0179285 A1 | 6/2018 | Bennett et al. |
| 2018/0214548 A1 | 8/2018 | Liu et al. |
| 2018/0282412 A1 | 10/2018 | Gu et al. |
| 2018/0339045 A1 | 11/2018 | Li et al. |
| 2018/0346569 A1 | 12/2018 | Wang et al. |
| 2018/0371093 A1* | 12/2018 | Bilic ....................... A61K 45/06 |
| 2019/0016797 A1 | 1/2019 | Arenas-Ramirez et al. |
| 2019/0127467 A1 | 5/2019 | Shah et al. |
| 2019/0144542 A1 | 5/2019 | Galler et al. |
| 2019/0388338 A1 | 12/2019 | Giesing et al. |
| 2021/0069325 A1 | 3/2021 | Chan et al. |
| 2021/0277110 A1* | 9/2021 | Verona ............... C07K 16/4258 |

FOREIGN PATENT DOCUMENTS

| | | |
|---|---|---|
| CA | 3 004 134 A1 | 5/2017 |
| CA | 3 004 138 A1 | 5/2017 |
| CN | 1880446 A | 12/2006 |
| CN | 103721255 A | 4/2014 |
| CN | 104024276 A | 9/2014 |
| CN | 108430509 A | 8/2018 |
| EP | 0296122 B1 | 12/1988 |
| EP | 0666868 B1 | 4/2002 |
| EP | 0590058 B1 | 11/2003 |
| EP | 2360254 A | 8/2011 |
| EP | 1817055 B1 | 12/2012 |
| EP | 1866339 B1 | 5/2013 |
| EP | 1947183 B1 | 7/2013 |
| EP | 3370769 A4 | 5/2019 |
| EP | 3371226 A4 | 7/2019 |
| EP | 3505535 A1 | 7/2019 |
| EP | 3514177 A1 | 7/2019 |
| EP | 3370768 B1 | 1/2022 |
| EP | 3370768 B9 | 3/2022 |
| GB | 2408508 A | 6/2005 |
| JP | 2017-105754 | 6/2017 |
| JP | 7051692 B2 | 4/2022 |
| RU | 2420587 C2 | 12/2010 |
| WO | WO 1988/001649 A1 | 3/1988 |
| WO | 9004036 A1 | 4/1990 |
| WO | WO 1990/04036 A1 | 4/1990 |
| WO | WO 1990/007861 A1 | 7/1990 |
| WO | WO 1992/22653 A1 | 12/1992 |
| WO | 9410202 A1 | 5/1994 |
| WO | 9411026 A2 | 5/1994 |
| WO | WO 1994/10202 A1 | 5/1994 |
| WO | WO 1994/11026 A2 | 5/1994 |
| WO | 9630046 A1 | 10/1996 |
| WO | WO 1996/30046 A1 | 10/1996 |
| WO | 1997/011971 A1 | 4/1997 |
| WO | WO 1997/11971 A1 | 4/1997 |
| WO | WO 1998/045332 A2 | 10/1998 |
| WO | 9903854 A1 | 1/1999 |
| WO | WO 1999/003854 A1 | 1/1999 |
| WO | 9920758 A1 | 4/1999 |
| WO | 9940196 A1 | 8/1999 |
| WO | WO 1999/45962 A1 | 9/1999 |
| WO | 0103720 A2 | 1/2001 |
| WO | 0156603 A1 | 8/2001 |
| WO | WO 2011/110604 A1 | 9/2001 |
| WO | 0183755 A2 | 11/2001 |
| WO | WO 2002/010192 A3 | 2/2002 |
| WO | 0243478 A2 | 6/2002 |
| WO | WO 2002/043478 A2 | 6/2002 |
| WO | 02066470 A1 | 8/2002 |
| WO | WO 2002/066630 A1 | 8/2002 |
| WO | 0210192 A3 | 9/2002 |
| WO | 02078731 A1 | 10/2002 |
| WO | 03037347 A1 | 5/2003 |
| WO | WO 2003/037347 A1 | 5/2003 |
| WO | 03064383 A2 | 8/2003 |
| WO | WO 2003/064383 A1 | 8/2003 |
| WO | 03077914 A1 | 9/2003 |
| WO | WO 2003/077914 A1 | 9/2003 |
| WO | WO 2004/004771 A1 | 1/2004 |
| WO | WO 2004/005281 A1 | 1/2004 |
| WO | WO 2004/045532 A2 | 6/2004 |
| WO | WO 2004/056875 A1 | 7/2004 |
| WO | WO 2004/072051 A1 | 8/2004 |
| WO | 2005007190 A1 | 1/2005 |
| WO | WO 2005/012359 A2 | 2/2005 |
| WO | WO 2005/039549 A1 | 5/2005 |
| WO | WO 2005/044853 A2 | 5/2005 |
| WO | 2005055808 A2 | 6/2005 |
| WO | WO 2005/073224 A2 | 8/2005 |
| WO | 2005115451 A2 | 12/2005 |
| WO | WO 2005/113556 A1 | 12/2005 |
| WO | WO 2005/121142 A1 | 12/2005 |
| WO | 2006028936 A2 | 3/2006 |
| WO | 2006083289 A2 | 8/2006 |
| WO | WO 2006/121168 A1 | 11/2006 |
| WO | WO 2006/122806 A1 | 11/2006 |
| WO | WO 2007/005874 A2 | 1/2007 |
| WO | WO 2007/030377 A1 | 3/2007 |
| WO | WO 2007/070514 A1 | 6/2007 |
| WO | WO 2007/084786 A1 | 7/2007 |

(56) References Cited

FOREIGN PATENT DOCUMENTS

| | | |
|---|---|---|
| WO | 2007095337 A2 | 8/2007 |
| WO | 2007133822 A1 | 11/2007 |
| WO | WO 2007/131201 A2 | 11/2007 |
| WO | WO 2008/024725 A1 | 2/2008 |
| WO | WO 2008/073687 A2 | 6/2008 |
| WO | 2008077546 A1 | 7/2008 |
| WO | WO 2008/132601 A1 | 11/2008 |
| WO | WO 2008/156712 A1 | 12/2008 |
| WO | WO 2007/04415 A1 | 1/2009 |
| WO | WO 2009/018386 A1 | 2/2009 |
| WO | WO 2009/080251 A1 | 7/2009 |
| WO | WO 2009/080252 A1 | 7/2009 |
| WO | WO 2009/080254 A1 | 7/2009 |
| WO | WO 2009/085462 A1 | 7/2009 |
| WO | WO 2009/085983 A1 | 7/2009 |
| WO | WO 2009/114335 A2 | 9/2009 |
| WO | WO 2009/114870 A2 | 9/2009 |
| WO | WO 2009/115562 A2 | 9/2009 |
| WO | 2009141386 A1 | 11/2009 |
| WO | 2010003118 A1 | 1/2010 |
| WO | WO 2010/002655 A2 | 1/2010 |
| WO | WO 2010/006086 A2 | 1/2010 |
| WO | WO 2010/007120 A1 | 1/2010 |
| WO | WO 2010/019570 A2 | 2/2010 |
| WO | WO 2010/026124 A1 | 3/2010 |
| WO | WO 2010/029082 A1 | 3/2010 |
| WO | WO 2010/029435 A1 | 3/2010 |
| WO | WO 2010/036380 A1 | 4/2010 |
| WO | WO 2010/036959 A2 | 4/2010 |
| WO | WO 2010/060937 A2 | 6/2010 |
| WO | 2010079039 A1 | 7/2010 |
| WO | WO 2010/077634 A1 | 7/2010 |
| WO | WO 2010/078580 A2 | 7/2010 |
| WO | WO 2010/101849 A1 | 9/2010 |
| WO | WO 2010/149755 A1 | 12/2010 |
| WO | 2011028683 A1 | 3/2011 |
| WO | WO 2011/025927 A1 | 3/2011 |
| WO | WO 2011/066501 A1 | 3/2011 |
| WO | 2011051726 A2 | 5/2011 |
| WO | WO 2011/076786 A1 | 6/2011 |
| WO | 2011051726 A3 | 7/2011 |
| WO | 2011090754 A1 | 7/2011 |
| WO | WO 2011/101409 A1 | 8/2011 |
| WO | WO 2011/131746 A2 | 10/2011 |
| WO | WO 2011/159877 A2 | 12/2011 |
| WO | WO 2012/022814 A1 | 2/2012 |
| WO | WO 2012/061448 A1 | 5/2012 |
| WO | WO 2012/145493 A1 | 10/2012 |
| WO | WO 2012/177624 A2 | 12/2012 |
| WO | WO 2013/006490 A2 | 1/2013 |
| WO | 2013028231 A1 | 2/2013 |
| WO | WO 2013/019906 A1 | 2/2013 |
| WO | 2013034904 A1 | 3/2013 |
| WO | 2013039954 A1 | 3/2013 |
| WO | WO 2011/155607 A1 | 8/2013 |
| WO | WO 2013/111105 A1 | 8/2013 |
| WO | WO 2013/124826 A1 | 8/2013 |
| WO | WO 2013/132044 A1 | 9/2013 |
| WO | WO 2013/171639 A1 | 11/2013 |
| WO | WO 2013/171640 A1 | 11/2013 |
| WO | WO 2013/171641 A1 | 11/2013 |
| WO | WO 2013/171642 A1 | 11/2013 |
| WO | WO 2013/184757 A1 | 12/2013 |
| WO | 2014031718 A1 | 2/2014 |
| WO | WO 2014/02 2332 A1 | 2/2014 |
| WO | 2014070934 A1 | 5/2014 |
| WO | WO 2014/072493 A1 | 5/2014 |
| WO | WO 2014/085318 A1 | 6/2014 |
| WO | WO 2014/100483 A1 | 6/2014 |
| WO | WO 2014/108198 A1 | 7/2014 |
| WO | 2014148895 A1 | 9/2014 |
| WO | WO 2014/141104 A1 | 9/2014 |
| WO | WO 2014/144080 A2 | 9/2014 |
| WO | WO 2014/151616 A1 | 9/2014 |
| WO | WO 2014/159562 A1 | 10/2014 |
| WO | WO 2014/159835 A1 | 10/2014 |
| WO | WO 2014/160160 A2 | 10/2014 |
| WO | WO 2014/179664 A2 | 11/2014 |
| WO | WO 2014/183066 A2 | 11/2014 |
| WO | WO 2014/184360 A1 | 11/2014 |
| WO | WO 2014/194302 A2 | 12/2014 |
| WO | WO 2014/206107 A1 | 12/2014 |
| WO | WO 2015/013389 A2 | 1/2015 |
| WO | 2015026684 A1 | 2/2015 |
| WO | WO 2015/024060 A1 | 2/2015 |
| WO | WO 2015/035606 A1 | 3/2015 |
| WO | WO 2015/036394 A1 | 3/2015 |
| WO | WO 2015/058573 A1 | 4/2015 |
| WO | 2015066188 A1 | 5/2015 |
| WO | 2015095410 A1 | 6/2015 |
| WO | WO 2015/085847 A1 | 6/2015 |
| WO | 2015112800 A1 | 7/2015 |
| WO | WO 2015/097563 A2 | 7/2015 |
| WO | WO 2015/112805 A1 | 7/2015 |
| WO | WO 2015/112900 A1 | 7/2015 |
| WO | WO 2015/117002 A1 | 8/2015 |
| WO | WO 2015/173756 A2 | 11/2015 |
| WO | WO 2015195163 A1 | 12/2015 |
| WO | WO 2016/077397 A2 | 5/2016 |
| WO | WO 2016/168716 | 10/2016 |
| WO | WO 2016/210223 A1 | 12/2016 |
| WO | 2017017623 A1 | 2/2017 |
| WO | 2017017624 A1 | 2/2017 |
| WO | 2017025051 A1 | 2/2017 |
| WO | WO 2017/024515 A1 | 2/2017 |
| WO | 2017040790 A1 | 3/2017 |
| WO | WO 2017/055404 A1 | 4/2017 |
| WO | WO 2017/055537 A1 | 4/2017 |
| WO | WO 2017/055966 | 4/2017 |
| WO | 2017079112 A1 | 5/2017 |
| WO | 2017079115 A1 | 5/2017 |
| WO | WO 2017/071625 A1 | 5/2017 |
| WO | WO 2017/079116 A2 | 5/2017 |
| WO | 2017106656 A1 | 6/2017 |
| WO | WO 2017/122130 A1 | 7/2017 |
| WO | WO 2017/196847 A1 | 11/2017 |
| WO | 2017210637 A1 | 12/2017 |
| WO | WO 2017/210637 | 12/2017 |
| WO | WO 2017/214182 A1 | 12/2017 |
| WO | WO 2018/026248 A1 | 2/2018 |
| WO | WO 2018/028383 A1 | 2/2018 |
| WO | 2018053405 A1 | 3/2018 |
| WO | WO 2018/036472 A1 | 3/2018 |
| WO | WO 2018/050027 A1 | 3/2018 |
| WO | WO 2018/053709 A1 | 3/2018 |
| WO | 2018213302 A1 | 11/2018 |
| WO | WO-2019048629 A1 * | 3/2019 ......... A61K 31/4155 |

OTHER PUBLICATIONS

Borch et al., "Reorienting the immune system in the treatment of cancer by using anti-PD-1 and anti-PD-L1 antibodies.", Drug Discovery Today, Sep. 2015, pp. 1127-1134, vol. 20(9).
Brown et al., "Blockade of Programmed Death-1 Ligands on Dendritic Cells Enhances T Cell Activation and Cytokine Production.", J Immunol, 2003, pp. 1257-1266, vol. 170.
Brüggemann and Taussig, "Production of human antibody repertoires in transgenic mice.", Curr Opin Biotechnol, 1997, pp. 455-458, vol. 8.
Brüggemann et al., "Human antibody production in transgenic mice: expression from 100 kb of the human IgH locus*.", Eur J Immunol, 1991, pp. 1323-1326, vol. 21.
Brusasco, V., "Book Review, Airway Smooth Muscle: Modelling the Asthmatic Response in Vitro.", Respiratiory Medicine, 1997, p. 179, vol. 91.
Cai et al., "C-Terminal Lysine Processing of Human Immunoglobulin G2 Heavy Chain in Vivo.", Biotechnol Bioeng, Feb. 2011, pp. 404-412, vol. 108(2).
Chames and Baty, "Bispecific antibodies for cancer therapy.", Curr Opin Drug Disc Dev, 2009, pp. 276-283, vol. 12(2).
Chari et al., "Immunoconjugates Containing Novel Maytansinoids: Promising Anticancer Drugs.", Cancer Res, Jan. 1, 1992, pp. 127-131, vol. 52.

(56) References Cited

OTHER PUBLICATIONS

Chen et al., "Molecular Pathways: Next-Generation Immunotherapy-Inhibiting Programmed Death-Ligand 1 and Programmed Death-1.", Clin Cancer Res, 2012, pp. 6580-6587, vol. 8(24).
Chien et al., "Significant structural and functional change of an antigen-binding site by a distant amino acid substitution: Proposal of a structural mechanism.", Proc. Natl. Acad. Sci., Jul. 1989, pp., 5532-5536, vol. 86.
Chothia and Lesk, "Canonical Structures for the Hypervariable Regions of Immunoglobulins.", Mol Biol, 1987, pp. 901-917, vol. 196.
Clayton, et al., "T cell Ig and Mucin Domain-Containing Protein 3 is Recruited to the Immune Synapse, Disrupts Stable Synapse Formation, and Associates Receptor Phosphates.", J Immunol, 2014, pp. 782-791, vol. 192(2).
Cole et al., "HuM291, a Humanized Anti-CD3 Antibody, is Immunosuppressive to T Cells While Exhibiting Reduced Mitogenicity in Vitro[1].", Transplantation, 1999, pp. 563-571, vol. 68(4).
Cook, R. C., "Economic and Clinical Impact of Multiple Myeloma to Managed Care.", J Manag Care Pharm., 2008, pp. S18-S25, vol. 14(7).
Da Silva et al., "Reversal of NK-Cell Exhaustion in Advanced Melanoma by Tim-3 Blockade.", Cancer Immunol Res, 2014, pp. 410-422, vol. 2(5).
Dall'Acqua et al., "Properties of Human IgG1s Engineered for Enhanced Binding to the Neonatal Fc Receptor (FcRn)*.", J Biol Chem, 2006, pp. 23514-23524, vol. 281(33).
Datta-Mannan et al., "Humanized IgG1 Variants with Differential Binding Properties to the Neonatal Fc Receptor: Relationship to Pharmacokinetics in Mice and Primates.", Drug Metab Dispos, 2007, pp. 86-94, vol. 35(1).
Diebolder et al., "Complement is Activated by IgG Hexamers Assembled at the Cell Surface.", Science, Mar. 13, 2014, pp. 1260-1263, vol. 343.
Dong et al., "B7-H1 pathway and its role in the evasion of tumor immunity.", J Mol Med, 2003, pp. 281-287, vol. 81.
Dranoff et al., "Vaccination with irradiated tumor cells engineered to secrete murin granulocyte-macrophage colony-stimulating factor stimulates potent, specific, and long-lasting anti-tumor activity.", Proc Natl Acad Sci U.S.A., 1993, pp. 3539-3543, vol. 90.
Dubowchik et al., "Doxorubicin Immunoconjugates Containing Bivalent, Lysosomally-Cleavable Dipeptide Linkages.", Bioorg. & Med. Chem. Letters, 2002, pp. 1529-1532, vol. 12: 1529-1532.
Faghfuri et al., "Nivolumab and pembrolizumab as immune-modulating monoclonal antibodies targeting the PD-1 receptor to treat melanoma.", Expert Rev. Anticancer Ther., 2015, pp. 981-993, vol. 15(9).
Ferrara et al., "Modulation of Therapeutic Antibody Effector Functions by Glycosylation Engineering: Influence of Golgi Enzyme Localization Domain and Co-Expression of Heterologous β1,4-N-acetylglucosaminyltransferase III and Golgi α-mannosidase II.", Biotechnol Bioeng, 2006, pp. 851-861, vol. 93.
Ferrara et al., "The Carbohydrate at FcY RIIIa Asn-162. An Element Required For High Affinity Binding to Non-Fuscosylated IgG Glycoforms*.", J Biol Chem, 2006, pp. 5032-5036, vol. 281(8).
Ferris et al., "Too Much of a Good Thing? Tim-3 and TCR Signaling in T Cell Exhaustion.", J Immunol, 2004, pp. 1525-1530, vol. 193(4).
Fishwild et al., "High-avidity human IgGK monoclonal antibodies from a novel strain of minilocus transgenic mice.", Nat Biotechnol, 1996, pp. 845-851, vol. 14.
Fourcade et al., "Upregulation of Tim-3 and PD-1 expression is associated with tumor antigen-specific CD8+ T cell dysfunction in melanoma patients.", J Exp Med, 2010, pp. 2175-2186, vol. 207.
Fransson et al., "Human Framework Adaptation of a Mouse Anti-Human IL-13 Antibody.", J Mol Biol, 2010, pp. 214-231, vol. 398.
Freeman et al., "Protect the killer: CTLs need defenses against the tumor.", Nat Med, 2002, pp. 787-789, vol. 8(8).

Gautron et al., "Enhanced suppressor function of TIM-3+FoxP3+ regulatory T cells.", Eur J Immunol, 2014, pp. 2703-2711, vol. 44(9).
Ghevaert et al., "Developing recombinant HPA-1a-specific antibodies with abrogated FcY receptor binding for the treatment of fetomaternal alloimmune thrombocytopenia.", J Clin Invest, 2008, pp. 2929-2938, vol. 118(8).
Goding, *Monoclonal Antibodies: Principles and Practice*, Chapter 3, pp. 59-103, Academic Press, 1986.
Golden-Mason et al., "Negative Immune Regulator Tim-3 is Overexpressed on T Cells in Hepatitis C Virus Infection and Its Blockade Rescues Dysfunctional CD4+ and CD8+ T cells.", J Virol, Sep. 2009, pp. 9122-9130, vol. 83(18).
Green and Jakobovits, "Regulation of B Cell Development by Variable Gene Complexity in Mice Reconstituted with Human Immunoglobulin Yeast Artificial Chromosomes.", J. Exp. Med., Aug. 1998, pp. 483-495, vol. 188(3).
Green et al., "Antigen-specific human monoclonal antibodies from mice engineered with human Ig heavy and light chain YACs.", Nature Genet., 1994, pp. 13-21, vol. 7.
Gupta et al., "Development of a Multidose Formulation for a Humanized Monoclonal Antibody Using Experimental Design Techniques.", AAPS PharmSci, 2003, pp. 1-9, vol. 5(2), Article 8.
Hallett et al., "Immunosuppressive Effects of Multiple Myeloma Are Overcome by PD-L1 Blockade.", J of American Society for Blood and Marrow Transplantation, 2011, pp. 1133-1145, vol. 17(1).
Hastings et al., "TIM-3 is expressed on activated human CD41 T cells and regulates Th1 and Th17 cytokines.", Eur J Immunol, 2009, pp. 2492-2501, vol. 39.
Hinman et al., "Preparation and Characterization of Monoclonal Antibody Conjugates of the Calicheamicins: a Novel and Potent Family of Antitumor Antibiotics.", Jul. 1993, Cancer Res, pp. 3336-3342, vol. 53.
Hinton et al., "An Engineered Human IgG1 Antibody with Longer Serum Half-Life.", J Immunol, 2005, pp. 346-356, vol. 176.
Hinton et al., "Engineered Human IgG Antibodies with Longer Half-lives in Primates*.", J Biol Chem, 2004, pp. 6213-6216, vol. 279(8).
Honda et al., "Tuning of Antigen Sensitivity by T Cell Receptor-Dependent Negative Feedback Controls T Cell Effector Function in Inflamed Tissues.", Immunity, Feb. 20, 2014, pp. 235-247, vol. 40(2).
Hoogenboom and Winter, "By-passing Immunisation. Human Antibodies from Synthetic Repertoires of Germline $V_H$ Gene Segments Rearranged in Virto.", J Mol Biol, 1992, pp. 381-388, vol. 227.
Hudes et al., "Temsirolimus, Interferon Alfa, or Both for Advanced Renal-Cell Carcinoma.", N Engl J Med, May 2007, pp. 2271-2281, vol. 356(22).
Idusogie et al., "Engineered Antibodies with Increased Activity to Recruit Complement.", J Immunol, 2001, pp. 2571-2575, vol. 166.
Iwai et al., "Involvement of PD-L1 on tumor cells in the escape from host immune system and tumor immunotherapy by PD-L1 blockade.", ProcNatl Acad Sci, Sep. 17, 2002, pp. 12293-12297, vol. 99.
Jeffrey et al., "Dipeptide-based highly potent doxorubicin antibody conjugates.", Bioorganic & Med Chem Letters, 2006, pp. 358-362, vol. 16.
Jones et al., "Tim-3 expression defines a novel population of dysfunctional T cells with highly elevated frequencies in progressive HIV-1 infection.", J Exp Med, 2008, pp. 2763-2779, vol. 205(12).
Kaas, et al., "IMGT/3Dstructure-DB IMGT/Structural Query, a database and a tool for immunoglobulin, T cell receptor and MHC structural data.", Nucl Acids Res, 2004, pp. D208-D210, vol. 32.
Kim et al., "Scientific Association of Human Telomerase Activity with Immortal Cells and Cancer.", Science, 1994, pp. 2011-2013, vol. 266.
Kim et al., "Mapping the site on human IgG for binding of the MHC class I-related receptor, FcRn.", Eur J Immunol, 1999, pp. 2819-2825, vol. 29.

(56) References Cited

OTHER PUBLICATIONS

King et al., "Monoclonal Antibody Conjugates of Doxorubicin Prepared with Branched Peptide Linkers: Inhibition of Aggregation by Methoxytriethyleneglycol Chains.", J Med Chem, 2002, pp. 4336-4343, vol. 45.

Klinger et al., "Multiplex Identification of Antigen-Specific T Cell Receptors Using a Combination of Immune Assays and Immune Receptor Sequencing.", PLOS One, Oct. 28, 2015, pp. 1-21, vol. 8(9).

Knappik et al., "Fully Snythetic Human Combinatorial Antibody Libraries (HuCAL) Based on Modular Consensus Frameworks and CDRs Randomized with Trinucleotides.", J Mol Biol, 2000, pp. 57-86, vol. 296.

Knight et al., "Pharmacodynamic enhancement of the anti-platelet antibody Fab abciximab by site-specific pegylation.", Platelet, 2004, pp. 409-418, vol. 15(7).

Kobrin et al., "A V region mutation in a phosphocholine-binding monoclonal antibody results in loss of antigen binding.", The Journal of Immunology, 1991, pp. 2017-2020, vol. 146.

Kohler and Milstein, "Continuous cultures of fused cells secreting antibody of predefined specificity.", Nature, 1975, pp. 495-497, vol. 256.

Konishi et al., "B7-H1 Expression on Non-Small Cell Lung Cancer Cells and Its Relationship with Tumor-Infiltrating Lymphocytes and Their PD-1 Expression.", Clin Cancer Res, Aug. 1, 2004, pp. 5094-5510, vol. 10.

Konno et al., "Fucose content of monoclonal antibodies can be controlled by culture medium osmolality for high antibody-dependent cellular cytotoxicity.", Cytotechnology, 2012, pp. 249-265, vol. 64.

Kratz et al., "Prodrugs of Anthracyclines in Cancer Chemotherapy.", Current Med. Chem, 2006, pp. 477-523, vol. 13.

Krebs et al., "High-Throughput generation and engineering of recombinant human antibodies.", J Immunol Meth, 2001, pp. 67-84, vol. 254.

Kugler et al., "Retraction: Regression of human metastatic renal cell carcinoma after vaccination with tumor cell-dendritic cell hybrids.", Nature Medicine, 2000, pp. 332-336, vol. 6.".

Lazar et al., "Engineered antibody Fc variants with enhanced effector function.", Proc Natal Acad Sci, Mar. 14, 2006, pp. 4005-4010, vol. 103(11).

Lefranc et al., "IMGT unique numbering for immunoglobulin and T cell receptor variable domains and Ig superfamily V-like domains.", Dev Comparat Immunol, 2003, pp. 55-77, vol. 27.

Lefranc et al., "IMGT, the international ImMunoGeneTics information system®.", Nucl Acid Res, 2005, pp. D593-D597, vol. 33.

Leong et al., "Adapting Pharmacokinetic Properties of a Humanized Anti-Interleukin-8 Antibody for Therapeutic Applications Using Site-Specific Pegylation.", Cytokine, 2001, pp. 106-119, vol. 16(3).

Lepenies et al., "The Role of Negative Costimulators During Parasitic Infections.", Endocr Metab Immune Disord Drug Targets, 2008, pp. 279-288, vol. 8.

Li et al., "Design and Synthesis of Paclitaxel Conjugated with an ErfB2-Recognizing Peptide, EC-1.", Biopolymers, 2007, pp. 225-230, vol. 87.

Liu et al., "Synthesis of 20-paclitaxel methyl 2-glucopyranosyl succinate for specific targeted delivery to cancer cells.", Biorganic & Medicinal Chemistry Letters, 2007, pp. 617-620, vol. 17.

Lode et al., "Targeted Therapy with a Novel Enediyene Antibiotic Calicheamicin ΘI1 Effectively Suppress Growth and Dissemination of Liver Metastases in a Syngenic Model of Murine Neuroblastoma.", Cancer Res, 1998, pp. 2925-2928, vol. 58.

Lonberg and Huszar, "Human Antibodies from Transgenic Mice.", Int Rev Immunol, 1995, pp. 65-93, vol. 13.

Lonberg et al., "Antigen-specific human antibodies from mice comprising four distinct genetic modifications.", Nature, 1994, pp. 856-859, vol. 368.

Lote et al., "PD-1 and PD-L1 blockage in gastrointestinal malignancies.", Cancer Treatment Reviews, 2015, pp. 893-903, vol. 41.

Maa et al., "Aggregation of recombinant human growth hormone induced by phenolic compounds.", Int J Pharm, 1996, pp. 155-168, vol. 140.

MacLennan et al., "Structure-Function Relationships in the Ca2+—Binding and Translocation Domain of SERCA1: physiological correlates in Brody disease.", Acta Physiol Scand, 1998, pp. 55-67, Suppl 643.

Mahoney et al., "Combination cancer immunotherapy and new immunomodulatory targets.", Nature Reviews, Aug. 2015, pp. 561-587, vol. 14.

Marks et al., "By-passing Immunization. Human antibodies from V-gene Libraries Displayed on Phage.", J Mol Biol, 1991, pp. 581-587, vol. 222.

McDermott et al., "Pembrolizumab: PD-1 Inhibition as a Therapeutic Strategy in Cancer.", Drugs of Today, 2015, pp. 7-19, vol. 51(1).

Mendez et al., "Functional transplant of megabase human immunoglobulin loci recapitulates human antibody response in mice.", Nat Genet, Feb. 15, 1997, pp. 146-156, vol. 15.

Mokyr et al., "Realization of the Therapeutic Potential of CTLA-4 Blockade in Low-Dose Chemotherapy-treated Tumor-bearing Mice.", Cancer Research, 1998, pp. 5301-5304, vol. 58.

Monney et al., "Th1-specific cell surface protein Tim-3 regulates macrophage activation and severity of an autoimmune disease.", Nature, 2002, pp. 536-541, vol. 415(6871).

Moore et al., "Engineered Fc variant antibodies with enhanced ability to recruit complement and mediate effector functions.", Mabs, 2010, pp. 181-189, vol. 2.

Mori et al., "Engineering Chinese Hamster Ovary Cells to Maximize Effector Function of Produced Antibodies Using FUT8 siRNA.", Biotechnol Bioeng, 2004, pp. 901-908, vol. 88(7).

Nagy et al., "Stability of cytotoxic luteinizing hormone-releasing hormone conjugate (AN-152) containing doxorubicin 14-O-hemiglutarate in mouse and human serum in vitro: Implications for the design of preclinical studies.", Proc Natl Acad Sci, Jan. 18, 2000, USA, pp. 829-834, vol. 97.

Nestle et al., "Vaccination of melanoma patients with peptide-or tumor lysate-pulsed dendritic cells.", Nature Medicine, 1998, pp. 328-332, vol. 4(3).

Ngiow et al., "Anti-TIM3 Antibody Promotes T Cell IFN-g-Mediated Antitumor Immunity and Suppresses Established Tumors.", Cancer Res, May 15, 2011, pp. 3540-3551, vol. 71(10).

Nunez-Prado et al., "The coming of age of engineered multivalent antibodies.", Drug Discovery Today, May 2015, pp. 588-594, vol. 20(5).

Olivier et al., "EB66 cell line, a duck embryonic stem cell-derived substrate for the industrial production of therapeutic monoclonal antibodies with enhanced ADCC activity.", Mabs, 2010, pp. 405-415, vol. 2(4).

Padlan, E., "A Possible Procedure For Reducing the Immunogenicity of Antibody Variable Domains While Preserving Their Ligand-Binding Properties.", Mol Immunol, 1991, pp. 489-499, vol. 28(4/5).

Pal et al., "Programmed Death-1 Inhibition in Renal Cell Carcinoma: Clinical Insights and Future Directions.", Clin Advances in Hematology & Oncology, Feb. 2014, pp. 90-99, vol. 12(2).

Panka et al., "Defining The Structural Correlates Responsible For Loss of Arsonate Affinity in an $ID^{CR}$ Antibody Isolated From an Autoimmune Mouse*.", 1993, pp. 1013-1020, vol. 30(11).

Pauken_Wherry, "Overcoming T cell exhaustion in infection and cancer.", Trends in Immunology, Apr. 2015, pp. 265-276, vol. 36(4).

Petkova et al., "Enhanced half-life of genetically engineered human IgG1 antibodies in a humanized FcRn mouse model: potential application in humorally mediated autoimmune disease.", Int Immunol, 2006, pp. 1759-1769, vol. 18(12).

Pol et al., "Trial Watch: DNA vaccines for cancer therapy.", Oncoimmunology, Feb. 2014, pp. e28185-1-e28185-10, vol. 3.

Popkov et al., "Human/mouse cross-reactive anti-VEGF receptor 2 recombinant antibodies selected from an immune b9 allotype rabbit antibody library.", Journal of Immunological Methods, 2004, pp. 149-164, vol. 288.

(56) References Cited

OTHER PUBLICATIONS

Remmele et al., "Differential Scanning Calorimetry. A Practical Tool for Elucidating Stability of Liquid Biopharmaceuticals.", Biopharm, Jun. 2000, pp. 36-46.
Remmele et al., "Interleukin-1 Receptor (IL-1R) Liquid Formulation Development Using Differential Scanning Calorimetry.", Pharm Res, 1998, pp. 200-208, vol. 15(2).
Richards et al., "Optimization of antibody binding to FcγRIIa enhances macrophage phagocytosis of tumor cells.", Mol Cancer Ther, Aug. 2008, pp. 2517-2527, vol. 7(8).
Rini et al., "Phase III Trial of Bevacizumab Plus Interferon Alfa Versus Interferon Alfa Monotherapy in Patients With Metastatic Renal Cell Carcinoma: Final Results of CALGB 90206.", J Clin Oncol, May 1, 2010, pp. 2137-2143, vol. 28(13).
Rong et al., "Tim-3 expression on periphal monocytes and CD3+ CD16/CD56+ natural killer-like T cells in patients with chronic hepatitis B.", Tissue Antigens, 2014, pp. 76-81, vol. 83(2).
Rother et al., "Discovery and Development of the complement inhibitor eculizumab for the treatment of paroxysmal nocturnal hemoglobinuria.", Nat Biotechnol, Nov. 7, 2002, pp. 1256-1264, vol. 25(11).
Rudikoff et al., "Single Amino Acid Substitution Altering Antigen-Binding Specificity.", PNAS, 1982, pp. 1979-1983, vol. 79.
Sabatos et al., "Interaction of Tim-3 and Tim-3 ligand regulates T helper type 1 responses and induction of periphal tolerance.", Nat Immunol, Nov. 2003, pp. 1102-1110, vol. 4(11).
Sakuishi et al., "Targeting Tim-3 and PD-1 pathways to reverse T cell exhaustion and restore anti-tumor immunity.", J Exp Med, 2010, pp. 2187-2194, vol. 207(10).
Sakuishi et al., "TIM3+FOXP3+ regulatory T cells are tissue-specific promoters of T-cell dysfunction in cancer.", Oncoimmunology, 2013, pp. e23849-1-e23849-9, vol. 2(4).
Sakuishi, K. and A. C. Anderson (2014). Tim-3 Regulation of Cancer Immunity. Tumor-Induced Immune Suppression. D. I. Gabrilovich and A. A. Hurwitz, Springer New York: 239-261.
Sanchez-Fueyo et al., "Tim-3 inhibits T helper type 1-mediated auto-and alloimmune responses and promotes immunlogical tolerance.", Nat Immunol, 2003, pp. 1093-1101, vol. 4(11).
Sasaki et al., "Stucture-Mutation Analysis of the ATPase Site of *Dictyostellium Discoideum Myosin II*.", Adv Biophys, 1998, pp. 1-24, vol. 35.
Sheets et al., "Efficient construction of a large nonimmune phage antibody library: The production of high-affinity human single-chain antibodies to protein antigens.", PTAS (USA), May 1998, pp. 6157-6162, vol. 95.
Shi et al., "De Novo Selection of High-Affinity Antibodies from Synthetic Fab Libraries Displayed on Phage as pIX Fusion Proteins.", J Mol Biol, 2010, pp. 385-396, vol. 397.
Shields et al., "High Resolution Mapping of the Binding Site on Human IgG1 for FcγRI, FcγRII, FcγRIII, and FcRn and Design of IgG1 Variants with Improved Binding to the FcγR*.", J Biol Chem, Mar. 2, 2001, pp. 6591-6604, vol. 276.
Shields et al., "Lack of Fucose on Human IgG1 N-Linked Oligosaccharide Improves Binding to Human FcRIII and Antibody-dependent Cellular Toxicity*.", J Biol Chem, 2002, pp. 26733-26740, vol. 277(30).
Shinkawa et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity*.", J Biol Chem, 2003, pp. 3466-3473, vol. 278.
Stavenhagen et al., "Fc Optimization of Therapeutic Antibodies Enhances Their Ability to Kill Tumor Cells In vitro and Controls Tumor Expansion In vivo via Low-Affinity Activating Fc; Receptors.", Cancer Res, 2007, pp. 8882-8890, vol. 67.
Stickler et al., "The human G1m1 allotype associates with CD4+ T-cell responsiveness to a highly conserved IgG1 constant region peptide and confers an asparaginyl endopeptidase cleavage site.", Genes and Immunity, 2011, pp. 213-221, vol. 12.
Suto and Srivastava, "A Mechanism for the Specific Immunogenicity of Heat Shock Protein-Chaperoned Peptides.", Science, 1995, pp. 1585-1588, vol. 269.
Swaika et al., "Current state of anti-PD-L1 and anti-PD-1 agents in cancer therapy*.", Mol Immunol, 2015, pp. 4-17, vol. 67.
Tamura et al., "Immunotherapy of Tumors with Autologous Tumor-Derived Heat Shock Protein Preparations.", Science, 1997, vol. 117-120, vol. 278.
Torgov et al., "Generation of an Intensely Potent Anthracycline by a Monoclonal Antibody-β-Galactosidase Conjugate.", Bioconj Chem, 2005, pp. 717-721, vol. 16.
UniProtKB Accession No. A0A0D9XEF3, 9ORYZ Uncharacterized protein. May 27, 2015 [found online Apr. 4, 2017 at http://www.uniprolorg/uniprot/A0A0D9XEF3] aa residues 111-118.
UniProtKB Accession No. E5ATZ2, PARRH Non-ribosomal peptide synthetase modules (EC 6.3.2.-) Feb. 8, 2011 [found online Apr. 5, 2017 athttp://www.uniprotorg/uniprot/E5ATZ2] aa residues 4403-4414.
UniProtKB Accession No. F4GQK8, PUSST Amino acid adenylation. Jun. 28, 2011 [found online Apr. 4, 2017 at http://www.uniprot.org/uniprot/F4GQK8] aa residues 482-490.
UniProtKB Accession No. W7MRS3, GIBM7 Uncharacterized protein. Apr. 16, 2014 [found online Apr. 5, 2017 at http://www.uniprot.org/uniprot/W7MRS3] aa residues 643-655.
Vaccaro et al., "Engineering the Fc Region of immunoglobin G to modulate in vivo antibody levels.", Nat Biotechnol, 2005, pp. 1283-1288, vol. 23.
Vaughan et al., "Human Antibodies with Sub-nanomolar Affinities Isolated from a large Non-immunized Phage Display Library.,", Nature Biotechnology, 1996, pp. 309-314, vol. 14.
Vitetta et al., "Redesigning Nature's Poisons to Create Anti-Tumor Reagents.", Science, Nov. 20, 1987, pp. 1098-1104, vol. 238.
Wang et al., "VISTA, a novel mouse Ig superfamily ligand that negatively regulates T cell responses.", J Exp Med, Mar. 14, 2011, pp. 577-592, vol. 208(3).
Winkler et al., "Changing the Antigen Binding Specificity by Single Point Mutations of an Anti-p24 (HIV-1) Antibody.", The Journal of Immunology, 2000, pp. 4505-4513, vol. 165.
Wolfl et al., "Activation-induced expression of CD137 permits detection, isolation, and expansion of the full repertoire of CD8+T cells responding to antigen without requiring knowledge of epitope specificities.", Blood, 2007, pp. 201-210, vol. 110(1).
Worn et al., "Stability engineering of antibody single-chain Fv fragments.", J Mol Biol, 2001, pp. 989-1010, vol. 305.
Wranik et al., "LUZ-Y, a Novel Platform for the Mammalian Cell Production of Full-length IgG-bispecific Antibodies*.", J Biol Chem, 2012, pp. 43331-43339, vol. 287(52).
Wu and Kabat, "An Analysis of the Sequences of the Variable Regions of Bence Jones Proteins and Myeloma Light Chains and Their Implications for Anti-body Complementarity*.", J Exp Med, 1970, pp. 211-250, vol. 132.
Xu et al., "In Vitro Characterization of Five Humanized OKT3 Effector Function Variant Antibodies.", Cell Immunol, 2000, pp. 16-26, vol. 200.
Yan et al., "Tim-3 Expression Defines Regulatory T Cells in Human Tumors.", PLoS One, Mar. 2013, pp. 1-10, vol. 8(3):e58006.
Yang et al., "Eradication of Established Tumors by a Fully Human Monoclonal Antibody to the Epidermal Growth Factor Receptor without Concomitant Chemotherapy.", Cancer Res, Mar. 15, 1999, pp. 1236-1243, vol. 59.
Yang et al., "Tailoring structure-function and pharmacokinetic properties of single-chain Fv proteins by site-specific PEGylation.", Protein Eng, 2003, pp. 761-770. vol. 16.
Yeung et al., "A Therapeutic Anti-VEGF Antibody with Increased Potency Independent of Pharmacokinetic Half-life.", Cancer Res, Apr. 15, 2010, pp. 3269-3277, vol. 70(8).
Yi, Q., "Novel Immunotherapies.", Cancer J, 2009, pp. 502-510, vol. 15(6).
Zalevsky et al., "Enhanced antibody half-life improves in vivo activity.", Nat Biotechnol, 2010, pp. 157-159, vol. 28.
Zhang et al., "Mechanism for Benzyl Alcohol-Induced Aggregation of Recombinant Human Interkeukin-1 Receptor Antagonist in Aqueous Solution.", J Pharm Sci, Dec. 2004, pp. 3076-3089, vol. 93(12).

(56) References Cited

OTHER PUBLICATIONS

Zhou et al., "Development of A Simple and Rapid Method for Producing Non-Fucosylated Oligomannose Containing Antibodies With Increased Effector Function.", Biotechnol Bioeng, Feb. 15, 2008, pp. 652-665, vol. 99(3).

Zhuang et al., "Ectopic Expression of TIM-3 in Lung Cancers. a Potential Independent Prognostice Factor for Patients With NSCLC.", Am J Clin Pathol, 2012, pp. 978-985, vol. 137(6).

Alegre et al., "A Non-Activating "Humanized" Anti-CD3 Monoclonal Antibody Retains Immunosuppressive Properties In Vivo.", Transplantation, Jun. 1994, pp. 1537-1543, vol. 57(11).

An et al., "IgG2m4, an engineered antibody isotype with reduced Fc function.", mAbs, 2009, pp. 572-579, vol. 1(6).

Baert et al., "Influence of Immunogenicity on the Long-Term Efficacy of Infliximab in Crohn's Disease.", N. Engl. J. Med, 2003, pp. 602-608, vol. 348(7).

Beduaddo et al., "Use of Biophysical Characterization in Preformulation Development of a Heavy-Chain Fragment of Botulinum Serotype B: Evaluation of Suitable Purification Process Conditions.", Pharm Res., Aug. 2004, pp. 1353-1361, vol. 21(8).

Dardalhon et al., "Tim-3/Galectin-9 Pathway: Regulation of Th1 Immunity through Promotion of CD11b+Ly-6G= Myeloid Cells.", J. of Immunology, Jun. 23, 2020, pp. 1383-1392, vol. 185(3).
UniProtKB/TrEMBL Accession No. A0A068NMJ6, Jul. 22, 2015 [online]. [Retrieved on Mar. 1-3, 28, 17-19, 25<URL: http://www.uniprot.org/uniprot/A0A068NMJ6.txt?version=6> entire document.
UniProtKB/TrEMBL Accession No. A0A068NN74, Jul. 22, 2015 [online]. [Retrieved on Mar. 1-3, 28, 17-19, 25 2017]. Retrieved from the internet: < URL: http://www.uniprotorg/uniprot/A0A068NN74.txt?version=6> entire document.
UniProtKB/TrEMBL Accession No. F4GQK8, Jul. 22, 2015 [online]. [Retrieved on Mar. 28, 2017]. Retrieved from the internet: <URL: 1-3, 17-19, 25 http://www.uniprot.org/uniprot1F4GQK8.txt?version=25> entire document.
UniProtKB/TrEMBL Accession No. A0A087NGW6, Apr. 29, 2015 [online]. [Retrieved on Mar. 28, 2017]. Retrieved from the internet: <URL: 1-3, 17-19, 25 http://www.uniprotorg/uniprot/A0A087NGW6.txt?version=3> entire document.
UniProtKB/TrEMBL Accession No. E5ATZ2, Jan. 7, 2015 [online]. [Retrieved on Mar. 28, 2017]. Retrieved from the Internet: <URL: 1-3, 17-19, 25 http://www.uniprot.org/uniprot/E5ATZ2.txt?version=24> entire document.
UniProtKB/TrEMBL Accession No. G9POK7, Jan. 7, 2015 [online]. [Retrieved on Mar. 28, 2017). Retrieved from the internet: <URL: 1-3, 17-19, 25 http://www.uniprot.org/uniprot/G9POK7.txt?version=13> entire document.
Kang et al., "Apoptosis of tumor infiltrating effector TIM-3+CD8+ T cells in colon cancer.", Scientific Reports, Oct. 23, 2015, 15659, pp. 1-12, vol. 5(1).
Kikushige et al., "TIM-3 as a novel therapeutic target for eradicating acute myelogenous leukemia stem cells.", International Journal of Hematology, Sep. 18, 2013, pp. 627-633, vol. 98.
Wang et al., "Tim-3 signaling pathway as a novel negative mediator in lipopolysaccharide-induced endotoxic shock.", Human Immunology, May 2014, pp. 470-478, vol. 75(5).
Heon et al., "IL-15 induces strong but short-lived tumor-infiltrating CD8 T cell responses through the regulation of Tim-3 in breast cancer.", Biochemical and Biophysical Research Communications, Aug. 2015, pp. 360-366, vol. 464(1).
Li et al., "The Galectin-9/Tim-3 pathway is involved in the regulation of NK cell function at the maternal-fetal interface in early pregnancy.", Cellular & Molecular Immunology, 2016, pp. 73-81, vol.
Morei da Silva et al., "Nivolumab: Anti-PD-1 monocl onal anti body cancer immunotherapy.", Drugs of the Future, Jan. 1, 2014, pp. 15-24, vol. 39(1).
Zhou et al., "Coexpression of Tim-3 and PD-1 identifies a CD8+ T-cell exhaustion phenotype in mice with disseminated acute myelogenous leukemia.", Blood, 2011, pp. 4501-4510, vol. 117(17).
Marwick et al., "Blockade of PD1 and TIM3 Restores Innate and Adaptive Immunity in Patients With Acute Alcoholic Hepatitis.", Gastroenterology : Official Publication of the AM Erican Gastroenterologi CAL Association, Mar. 1, 2015, pp. 590-610, vol. 148(3).
Collin, M., "Immune checkpoint inhibitors: a patent review (2010-2015).", Expert Opin. On Therapeuitc Agents, Apr. 18, 2016, pp. 555-564, vol. 26(5).
Green, L., "Antibody engineering via genetic engineering of the mouse: XenoMouse strains are a vehicle for the facile generation of therapeutic human monoclonal antibodies.", J Immunol Methods, 1999, pp. 11-23, vol. 231.
Wolchok et al., "Guidelines for the Evaluation of Immune Therapy Activity in Solid Tumors: Immune-Related Response Criteria.", (2009) Clin Cancer Res, pp. 7412-7420, vol. 15(23).
Honegger and Plückthun, "Yet Another Numbering Scheme for Immunoglobin Variable Domains: an Automatic Modeling and Analysis Tool.", J Mol Biol, 2001, pp. 657-670, vol. 309.
Mackiewicz and Mackiewicz, "BRAF and MEK inhibitors in the era of immunotherapy in melanoma patients.", Contem Oncol, 2018, pp. 68-72, vol. 22.
Motzer et al., "Efficacy of everolimus in advanced renal cell carcinoma: a double-blind, randomised, placebo-controlled phase III trial.", Lancet, Aug. 9, 2008, pp. 449-456, vol. 372(9637).
Anonymous: HNCT02908906 a Study to Evaluate the Safety, Pharmacokinetics, Pharmacodynamics, and Clinical Activity of JNJ-63723283, an Anti-PD-1 Monoclonal Antibody, in Participants With Advanced Cancers-H, Jan. 4, 2018 (Jan. 4, 2018), XP055579182, Retrieved from the Internet: URL:https://clinicaltrials.gov/ct2/history/NCT02908906?V 15=View#StudyPageTop [retrieved on Apr. 9, 2019].
Xinsheng Tian et al: "Small-Angle X-ray 37-46 Scattering Screening Complements Conventional Biophysical Analysis: Comparative Structural and Biophysical Analysis of Monoclonal Antibodies IgGI, IgG2, and IgG4", Journal of Pharmaceutical Sciences, vol. 103, No. 6, Jun. 1, 2014 (Jun. 1, 2014), pp. 1701-1710, XP055576640, US ISSN: 0022-3549.
Tomoko Freshwater et al: "Evaluation of dosing strategy for pembrolizumab for oncology indications", Journal for Immunotherapy of Cancer, Biomed Central LTD, London, UK, vol. 5, No. 1, May 16, 2017 (May 16, 2017), pp. 1-9, XP021245121, DOI: 10.1186/S40425-017-0242-5.
Jeroen J.M.A. Hendrikx et al: "Fixed 1-36 Dosing of Monoclonal Antibodies in Oncology", The Oncologist, vol. 22, No. 10, Jul. 28, 2017 (Jul. 28, 2017), pp. 1212-1221, XP055579196, US ISSN: 1083-7159, DOI: 10.1634/theoncologist.2017-0167.
International Search Report relating to International Patent Application No. PCT/US2016/059833, filed on Nov. 1, 2016. Date of Mailing of International Search Report: Apr. 13, 2017.
Written Opinion of the International Search Authority relating to International Patent Application No. PCT/US2016/059833, filed on Nov. 1, 2016. Date of Mailing of Written Opinion: Apr. 13, 2017.
International Search Report relating to International Patent Application No. PCT/US2016/059836, filed on Nov. 1, 2016. Date of Mailing of International Search Report: Apr. 10, 2017.
Written Opinion of the International Search Authority relating to International Patent Application No. PCT/US2016/059836, filed on Nov. 1, 2016. Date of Mailing of Written Opinion: Apr. 10, 2017.
International Search Report relating to International Patent Application No. PCT/US2016/059837, filed on Nov. 1, 2016. Date of Mailing of International Search Report: May 22, 2017.
Written Opinion of the International Search Authority relating to International Patent Application No. PCT/US2016/059837, filed on Nov. 1, 2016. Date of Mailing of Written Opinion: May 22, 2017.
Supplementary European Search Report, EP 16862773.5, Mailed Jun. 26, 2019.
Supplementary European Search Report, EP 16862775.0, Mailed Apr. 24, 2019.
Supplementary European Search Report, EP 16862776.8, Mailed Jun. 18, 2019.
International Search Report relating to International Patent Application No. PCT/1B2019/050449, filed on Jan. 19, 2019. Date of Mailing of International Search Report: Jul. 19, 2019.

(56) References Cited

OTHER PUBLICATIONS

Written Opinion of the International Search Authority relating to International Patent Application No. PCT/IB2019/050449, filed on Jan. 19, 2019. Date of Mailing of Written Opinion: Jul. 19, 2019.
Calvo et al., "Interim results of a phase 1/2 study of JNJ-63723283, an anti-PD-1 monoclonal antibody, in patients with advanced cancers", *Journal of Clinical Oncology*, Feb. 10, 2018, p. 58, vol. 36.
Rutkowski et al., "Anti-PD-1 antibody cetrelimab (JNJ-63723283) in patients with advanced cancers: Updated phase I/II study results", *Journal of Clinical Oncology*, Mar. 10, 2019, p. 31, vol. 37.
Ferrante et al., "Discovery and pharmacological characterization of JNJ-63723283, an anti-programmed cell death protein-1 (PD-1) antibody that blocks PD-1 function", Poster No. P364. SITC 2017 Conference, Nov. 8-12, 2017, National Harbor, Maryland.
Rutkowski et al., "Anti-PD-1 antibody cetrelimab (JNJ-63723283) in patients with advanced cancers: updated phase 1/2 study results", Abstract No. 131, ASCO-SITC Clinical Immuno-Oncology Symposium, Feb. 28-Mar. 2, 2019, San Francisco, California.
Calvo et al., "Interim Results of a Phase 1/2 Study of JNJ-63723283, an Anti-PD-1 Monoclonal Antibody, in Patients with Advanced Cancers", Abstract No. 58, ASCO-SITC Clinical Immuno-Oncology Symposium, Jan. 25-27, 2018, San Francisco, California.
Ferrante et al., "Discovery and pharmacological characterization of JNJ-63723283, an anti-programmed cell death protein-1 (PD-1) antibody that blocks PD-1 function", SITC 2017 Annual Meeting Abstracts Book Abstract P364 at pp. 437-438, SITC 2017 Conference, Nov. 8-12, 2017, National Harbor, Maryland.
Deangelis et al., "Discovery and pharmacological characterization of cetrelimab (JNJ-63723283), an anti-programmed cell death protein-1 (PD-1) antibody, in human cancer models", Cancer Chemotherapy and Pharmacology, 2022, 89(4), pp. 515-527.
DiMasi et al., "Innovation in the pharmaceutical industry: New estimates of R&D costs", Journal of Health Economics 47 (2016) pp. 20-33.
Felip et al., "First-in-human, open-label, phase 1/2 study of the monoclonal antibody programmed cell death protein-1 (PD-1) inhibitor cetrelimab (JNJ-63723283) in patients with advanced cancers", Cancer Chemotherapy and Pharmacology, 2022, 89(4), pp. 499-514.
Geoerger at al., "Atezolizumab for children and young adults with previously treated solid tumours, non-Hodgkin lymphoma, and Hodgkin lymphoma (iMATRIX): a multicentre phase 1-2 study", www.thelancet.com/oncology, vol. 21, Jan. 2020, pp. 134-144.
OSI Pharmaceuticals, *LLC* v. *Apotex Inc.*, No. 2018-1925 (Fed. Cir. Oct. 4, 2019).
U.S. National Library of Medicine, ClinicalTrials.gov, "A Study to Evaluate the Safety, Pharmacokinetics, Pharmacodynamics, and Clinical Activity of JNJ-63723283, an Anti-PD-1 Monoclonal Antibody, in Participants With Advanced Cancers", First Posted:Sep. 21, 2016, [retrieved on Oct. 26, 2022], retrieved from the internet: URL: https://clinicaltrials.gov/ct2/show/NCT02908906>.
Wang et al., "Unexpected Toxicities When Nivolumab Was Given as Maintenance Therapy following Allogeneic Stem Cell Transplantation", Biol Blood Marrow Transplant 26 (2020) 1025_1027.
Winkler et al., *J Immunol*(2000) 165 (8): 4505-4514.
Qin et al., "PD-1/PD-L1 signaling pathway and the application of its antibody in cervical cancer immunotherapy", Chemistry of Life, 2017, vol. 37, No. 6, pp. 992-997 (see English Abstract as provided).
Hendrikx, et al., "Fixed 1-36 Dosing of Monoclonal Antibodies in Oncology", The Oncologist, vol. 22, No. 10, Jul. 28, 2017 (Jul. 28, 2017), pp. 1212-1221, XP055579196, US ISSN: 1083-7159, DOI: 10.1634/theoncologist.2017-0167 the whole document.
Martin and Thornton, "Structural Families in Loops of Homologous Proteins: Automatic Classification, Modelling and Application to Antibodies.", J Bmol Biol, 1996, pp. 800-815, vol. 263.
Tian, et al., "Small-Angle X-ray 37-46 Scattering Screening Complements Conventional Biophysical Analysis: Comparative Structural and Biophysical Analysis of Monoclonal Antibodies IgGI, IgG2, and IgG4", Journal of Pharmaceutical Sciences, vol. 103, No. 6, Jun. 1, 2014 (Jun. 1, 2014), pp. 1701-1710, XP055576640, US ISSN: 0022-3549.

\* cited by examiner

METHODS OF TREATING CANCERS WITH ANTAGONISTIC ANTI-PD-1 ANTIBODIES

CROSS-REFERENCE TO RELATED APPLICATIONS

This application claims the benefit of U.S. Provisional Application Ser. No. 62/620,106, filed 22 Jan. 2018, and U.S. Provisional Application Ser. No. 62/794,195, filed 18 Jan. 2019, the entire contents of which are incorporated herein by reference.

FIELD OF THE INVENTION

The present invention relates to methods of treating cancers with antagonistic anti-PD-1 antibodies, formulations of the antagonistic anti-PD-1 antibodies and drug products of the anti-PD-1 antibodies.

SEQUENCE LISTING

This application contains a Sequence Listing submitted via EFS-Web, the entire content of which is incorporated herein by reference. The ASCII text file, created on 18 Jan. 2019, is named JBI5152USNP_ST25.txt and is 12 kilobytes in size.

BACKGROUND OF THE INVENTION

The immune system is tightly controlled by a network of costimulatory and co-inhibitory ligands and receptors. These molecules provide secondary signals for T cell activation and provide a balanced network of positive and negative signals to maximize immune responses against infection and tumors, while limiting immunity to self (Wang et al., (Epub Mar. 7, 2011) *J Exp Med* 208(3):577-92; Lepenies et al., (2008) *Endocr Metab Immune Disord Drug Targets* 8:279-288). Immune checkpoint therapy, targeting co-inhibitory pathways in T cells to promote antitumor immune responses, has led to advances in clinical care of cancer patients.

PD-1 is a negative immune checkpoint molecule that suppresses $CD4^+$ and $CD8^+$ T cell functions in the tumor microenvironment (TME). PD-1 engagement with its ligands (PD-L1 and PD-L2) drives T cell anergy and exhaustion in tumors by inhibiting multiple pathways downstream of the T cell receptor signaling, resulting in decreased T cell survival, growth and proliferation, compromised effector function, and altered metabolism. Preclinical studies have demonstrated that the PD-1 pathway blockade can reverse T cell exhaustion and stimulate anti-tumor immunity.

While anti-PD-1/PD-L1 antibodies are demonstrating encouraging clinical responses in patients with multiple solid tumors, the response rates are still fairly low, about 15%-20% in pretreated patients (Swaika et al., (2015) *Mol Immunol.* doi: 10.1016/j.molimm.2015.02.009).

Therefore, there is a need for new therapeutics that inhibit the immunosuppressive activity of checkpoint inhibitors such as PD-1 to be used for cancer immunotherapy.

SUMMARY OF THE INVENTION

The invention provides a method of treating a cancer, comprising administering to a subject diagnosed with the cancer an antagonistic anti-PD1 antibody or an antigen binding fragment thereof, comprising a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6 at a dose of between about 240 mg and about 480 mg.

The invention also provides a pharmaceutical composition comprising between about 10 mg/ml and about 30 mg/ml cetrelimab, about 10 mM histidine, about 8.0% (w/v) sucrose, about 0.04% (w/v) polysorbate-20 and about 20 μg/ml EDTA at pH 6.5;

about 10 mg/ml cetrelimab, about 10 mM histidine, about 8.0% (w/v) sucrose, about 0.04% (w/v) polysorbate-20 and about 20 μg/ml EDTA at pH 6.5;

about 30 mg/ml cetrelimab, about 10 mM histidine, about 8.0% (w/v) sucrose, about 0.04% (w/v) polysorbate-20 and about 20 μg/ml EDTA at pH 6.5;

a lyophilized formulation comprising between about 90 mg and about 240 mg of cetrelimab and one or more pharmaceutically acceptable excipients;

a lyophilized formulation comprising about 90 mg of cetrelimab and one or more pharmaceutically acceptable excipients; or a lyophilized formulation comprising about 240 mg of cetrelimab and one or more pharmaceutically acceptable excipients.

The invention also provides a drug product comprising between about 10 mg/ml and about 30 mg/ml cetrelimab, about 10 mM histidine, about 8.0% (w/v) sucrose, about 0.04% (w/v) polysorbate-20 and about 20 μg/ml EDTA at pH 6.5;

about 10 mg/ml cetrelimab, about 10 mM histidine, about 8.0% (w/v) sucrose, about 0.04% (w/v) polysorbate-20 and about 20 μg/ml EDTA at pH 6.5;

about 30 mg/ml cetrelimab, about 10 mM histidine, about 8.0% (w/v) sucrose, about 0.04% (w/v) polysorbate-20 and about 20 μg/ml EDTA at pH 6.5;

a lyophilized formulation comprising between about 90 mg and about 240 mg of cetrelimab and one or more pharmaceutically acceptable excipients;

a lyophilized formulation comprising about 90 mg of cetrelimab and one or more pharmaceutically acceptable excipients; or a lyophilized formulation comprising about 240 mg of cetrelimab and one or more pharmaceutically acceptable excipients.

The invention also provides a drug product comprising between about 10 mg/ml and about 30 mg/ml cetrelimab, about 10 mM histidine, about 8.0% (w/v) sucrose, about 0.04% (w/v) polysorbate-20 and about 20 μg/ml EDTA at pH 6.5;

about 10 mg/ml cetrelimab, about 10 mM histidine, about 8.0% (w/v) sucrose, about 0.04% (w/v) polysorbate-20 and about 20 μg/ml EDTA at pH 6.5;

about 30 mg/ml cetrelimab, about 10 mM histidine, about 8.0% (w/v) sucrose, about 0.04% (w/v) polysorbate-20 and about 20 μg/ml EDTA at pH 6.5;

a lyophilized formulation comprising between about 90 mg and about 240 mg of cetrelimab and one or more pharmaceutically acceptable excipients;

a lyophilized formulation comprising about 90 mg of cetrelimab and one or more pharmaceutically acceptable excipients; or a lyophilized formulation comprising about 240 mg of cetrelimab and one or more pharmaceutically acceptable excipients, for the treatment of a cancer.

DETAILED DESCRIPTION OF THE INVENTION

Figure 1:
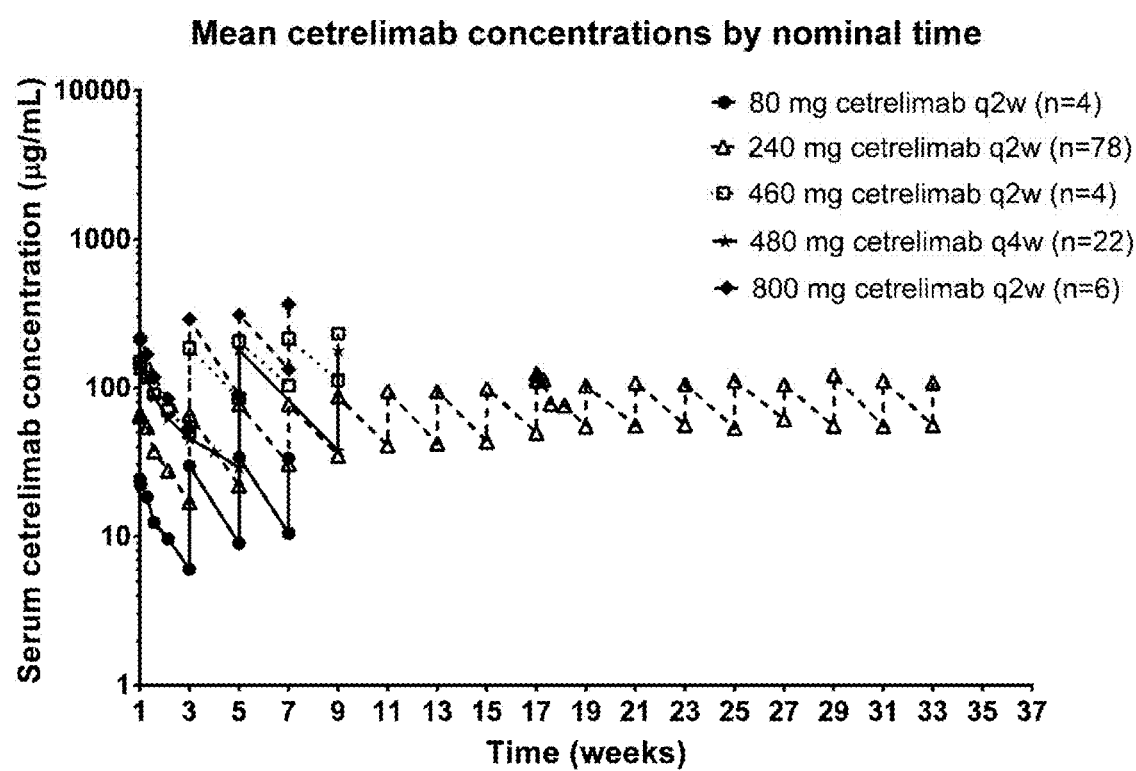
FIG. 1 shows the mean serum concentration (g/ml) of JNJ-63723283 (cetrelimab) over time in subjects dosed 80 mg, 240 mg, 460 mg, 480 mg or 800 mg once in two weeks (q2w) or once in four weeks (q4w) as indicated. The number of patients (n) dosed is shown in parenthesis.

All publications, including but not limited to patents and patent applications, cited in this specification are herein incorporated by reference as though fully set forth.

It is to be understood that the terminology used herein is for the purpose of describing embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein may be used in the practice for testing of the present invention, exemplary materials and methods are described herein. In describing and claiming the present invention, the following terminology will be used.

As used in this specification and the appended claims, the singular forms "a," "an," and "the" include plural referents unless the content clearly dictates otherwise. Thus, for example, reference to "a cell" includes a combination of two or more cells, and the like.

The transitional terms "comprising," "consisting essentially of," and "consisting of" are intended to connote their generally accepted meanings in the patent vernacular; that is, (i) "comprising," which is synonymous with "including," "containing," or "characterized by," is inclusive or open-ended and does not exclude additional, unrecited elements or method steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents) also provide as embodiments those independently described in terms of "consisting of" and "consisting essentially of."

"Antagonist" or "antagonistic" refers to an anti-PD1 antibody which upon binding to PD-1 suppresses at least one biological activity mediated by PD-1 ligand PD-L1 or PD-L2. The anti-PD-1 antibody is an antagonist when the at least one biological activity mediated by PD-L1 or PD-L2 is suppressed by at least about 20%, 30%, 40%, 45%, 50%, 55%, 60%, 65%, 70%, 75%, 80%, 85%, 90%, 95%, or 100% greater than in the absence of the antagonist (e.g., negative control), or when the suppression is statistically significant when compared to the suppression in the absence of the antagonist. A typical biological activity that is mediated by PD-L1 or PD-L2 binding to PD-1 is inhibition of antigen-specific CD4+ and/or CD8+ T cells. Therefore, antagonistic antibody relieves PD-L1 mediated suppression resulting in enhancement of immune responses.

"PD-1" refers to human programmed cell death protein 1, PD-1. PD-1 is also known as CD279 or PDCD1. The amino acid sequence of the mature human PD-1 (without signal sequence) is shown in SEQ ID NO: 11. The extracellular domain spans residues 1-150, the transmembrane domain spans residues 151-171 and the cytoplasmic domain spans residues 172-268 of SEQ ID NO: 11.

SEQ ID NO: 11
PGWFLDSPDRPWNPPTFSPALLVVTEGDNATFTCSFSNTSESFVLNWYRM
SPSNQTDKLAAFPEDRSQPGQDCRFRVTQLPNGRDFHMSVVRARRNDSGT
YLCGAISLAPKAQIKESLRAELRVTERRAEVPTAHPSPSPRPAGQFQTLV
VGVVGGLLGSLVLLVWVLAVICSRAARGTIGARRTGQPLKEDPSAVPVFS
VDYGELDFQWREKTPEPPVPCVPEQTEYATIVFPSGMGTSSPARRGSADG
PRSAQPLRPEDGHCSWPL

"Antibodies" is meant in a broad sense and includes immunoglobulin molecules belonging to any class, IgA, IgD, IgE, IgG and IgM, or sub-class IgA1, IgA2, IgG1, IgG2, IgG3 and IgG4 and including either kappa (κ) and lambda (λ) light chain. Antibodies include monoclonal antibodies, full length antibodies, antigen binding fragments, bispecific or multispecific antibodies, dimeric, tetrameric or multimeric antibodies, single chain antibodies, domain antibodies and any other modified configuration of the immunoglobulin molecule that comprises an antigen binding fragment of the required specificity. "Full length antibodies" are comprised of two heavy chains (HC) and two light chains (LC) inter-connected by disulfide bonds. Each heavy chain is comprised of a heavy chain variable region (VH) and a heavy chain constant region (comprised of domains CH1, hinge, CH2 and CH3). Each light chain is comprised of a light chain variable region (VL) and a light chain constant region (CL). The VH and the VL may be further subdivided into regions of hypervariability, termed complementarity determining regions (CDR), interspersed with framework regions (FR). Each VH and VL is composed of three CDRs and four FR segments, arranged from amino-terminus to carboxy-terminus in the following order: FR1, CDR1, FR2, CDR2, FR3, CDR3, and FR4. Antibodies include antibodies generated using various technologies, including antibodies generated from immunized mice or rat or identified from phage or mammalian display libraries as described herein.

"Complementarity determining regions (CDR)" are antibody regions that bind an antigen. There are three CDRs in the VH (HCDR1, HCDR2, HCDR3) and three CDRs in the VL (LCDR1, LCDR2, LCDR3). CDRs may be defined using various delineations such as Kabat (Wu et al. (1970) *J Exp Med* 132: 211-50) (Kabat et al., Sequences of Proteins of Immunological Interest, 5th Ed. Public Health Service, National Institutes of Health, Bethesda, Md., 1991), Chothia (Chothia et al. (1987) *J Mol Biol* 196: 901-17), IMGT (Lefranc et al. (2003) *Dev Comp Immunol* 27: 55-77) and AbM (Martin and Thornton (1996) *J Bmol Biol* 263: 800-15). The correspondence between the various delineations and variable region numbering are described (see e.g. Lefranc et al. (2003) *Dev Comp Immunol* 27: 55-77; Honegger and Pluckthun, (2001) *J Mol Biol* 309:657-70; International ImMunoGeneTics (IMGT) database; Web resources, http://www_imgt_org). Available programs such as abYsis by UCL Business PLC may be used to delineate the CDRs. The term "CDR", "HCDR1", "HCDR2", "HCDR3", "LCDR1", "LCDR2" and "LCDR3" as used herein includes CDRs defined by any of the methods described supra, Kabat, Chothia, IMGT or AbM, unless otherwise explicitly stated in the specification.

"Antigen binding fragment" refers to a portion of an immunoglobulin molecule that retains the antigen binding properties of the parental full length antibody. Exemplary antigen binding fragments are heavy chain complementarity determining regions (HCDR) 1, 2 and/or 3, light chain complementarity determining regions (LCDR) 1, 2 and/or 3, the VH, the VL, the VH and the VL, Fab, F(ab')2, Fd and Fv fragments as well as domain antibodies (dAb) consisting of either one VH domain or one VL domain. The VH and the VL domains may be linked together via a synthetic linker to form various types of single chain antibody designs in which the VH/VL domains pair intramolecularly, or intermolecularly in those cases when the VH and VL domains are expressed by separate chains, to form a monovalent antigen binding site, such as single chain Fv (scFv) or diabody; described for example in Int. Pat. Publ. No. WO1998/44001, Int. Pat. Publ. No. WO1988/01649; Int. Pat. Publ. No. WO1994/13804; Int. Pat. Publ. No. WO1992/01047.

"Humanized antibody" refers to an antibody in which CDR sequences are derived from non-human species and the frameworks are derived from human immunoglobulin sequences. Humanized antibody may include substitutions in the framework so that the framework may not be an exact copy of expressed human immunoglobulin or human immunoglobulin germline gene sequences. Antibodies in which at least one CDR is derived from non-human species and at least one framework is derived from human immunoglobulin sequences are humanized antibodies. Humanized antibody may include substitutions in the frameworks so that the frameworks may not be exact copies of expressed human immunoglobulin or human immunoglobulin germline gene sequences.

"Human antibody" refers to an antibody that is optimized to have minimal immune response when administered to a human subject. Variable regions of human antibody are derived from human germline immunoglobulin sequences. If the antibody contains a constant region or a portion of the constant region, the constant region is also derived from human germline immunoglobulin sequences.

Human antibody comprises heavy or light chain variable regions that are "derived from" human germline immunoglobulin sequences if the variable regions of the antibody are obtained from a system that uses human germline immunoglobulin genes. Such exemplary systems are human immunoglobulin gene libraries displayed on phage or mammalian cells, and transgenic non-human animals such as mice, rats or chicken carrying human immunoglobulin loci. "Human antibody" typically contains amino acid differences when compared to the immunoglobulins expressed in humans due to differences between the systems used to obtain the antibody and human immunoglobulin loci, introduction of naturally occurring somatic mutations, intentional introduction of substitutions into the framework or the CDRs. "Human antibody" is typically about 80%, 81%, 82%, 83%, 84%, 85%, 86%, 87%, 88%, 89%, 90%, 91%, 92%, 93%, 94%, 95%, 96%, 97%, 98% or 99% identical in amino acid sequence to an amino acid sequence encoded by human germline immunoglobulin sequences. In some cases, "human antibody" may contain consensus framework sequences derived from human framework sequence analyses, for example as described in (Knappik et al. (2000) *J Mol Biol* 296: 57-86), or synthetic HCDR3 incorporated into human immunoglobulin gene libraries displayed on phage, for example as described in (Shi et al. (2010) *J Mol Biol* 397: 385-96), and in Int. Patent Publ. No. WO2009/085462. Antibodies in which CDRs are derived from a non-human species are not included in the definition of "human antibody".

"Monoclonal antibody" refers to an antibody population with single amino acid composition in each antibody chain except for possible well known alterations such as removal of C-terminal lysine from the antibody heavy chain or alterations due to post-translational modification(s) of amino acids, such as methionine oxidation or asparagine or glutamine deamidation. Monoclonal antibodies typically specifically bind one antigenic epitope, except that bispecific or multispecific monoclonal antibodies specifically bind two or more distinct antigenic epitopes. Monoclonal antibodies may have heterogeneous glycosylation within the antibody population. Monoclonal antibody may be monospecific or multispecific, or monovalent, bivalent or multivalent. A bispecific antibody is included in the term monoclonal antibody.

"Isolated" refers to a homogenous population of molecules (such as synthetic polynucleotides or a protein such as an antibody) which have been substantially separated and/or purified away from other components of the system the molecules are produced in, such as a recombinant cell, as well as a protein that has been subjected to at least one purification or isolation step. "Isolated antibody" refers to an antibody that is substantially free of other cellular material and/or chemicals and encompasses antibodies that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

A "cancer cell" or a "tumor cell" refers to a cancerous, pre-cancerous or transformed cell, either in vivo, ex vivo, or in tissue culture, that has spontaneous or induced phenotypic changes. These changes do not necessarily involve the uptake of new genetic material. Although transformation may arise from infection with a transforming virus and incorporation of new genomic nucleic acid, uptake of exogenous nucleic acid or it can also arise spontaneously or following exposure to a carcinogen, thereby mutating an endogenous gene. Transformation/cancer is exemplified by morphological changes, immortalization of cells, aberrant growth control, foci formation, proliferation, malignancy, modulation of tumor specific marker levels, invasiveness, tumor growth in suitable animal hosts such as nude mice, and the like, in vitro, in vivo, and ex vivo (Freshney, Culture of Animal Cells: A Manual of Basic Technique (3rd ed. 1994)).

"Cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor.

"About" means within an acceptable error range for the particular value as determined by one of ordinary skill in the art, which will depend in part on how the value is measured or determined, i.e., the limitations of the measurement system. Unless explicitly stated otherwise within the Examples or elsewhere in the Specification in the context of a particular assay, result or embodiment, "about" means within one standard deviation per the practice in the art, or a range of up to 5%, whichever is larger.

"Subject" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. The terms "subject" and "patient" can be used interchangeably herein.

"Treat" or "treatment" refers to both therapeutic treatment and prophylactic or preventative measures, wherein the object is to prevent or slow down (lessen) an undesired physiological change or disorder, such as growth and/or spreading of tumor cells. Beneficial or desired clinical results include alleviation of symptoms, shrinkage of tumor size, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if a subject was not receiving treatment. Those in need of treatment include those already with the condition or disorder as well as those prone to have the condition or disorder or those in which the condition or disorder is to be prevented.

"Therapeutically effective amount" refers to an amount effective, at doses and for periods of time necessary, to achieve a desired therapeutic result. A therapeutically effective amount may vary depending on factors such as the disease state, age, sex, and weight of the individual, and the ability of a therapeutic or a combination of therapeutics to elicit a desired response in the individual. Exemplary indicators of an effective therapeutic or combination of therapeutics that include, for example, improved well-being of the patient.

"Anti-PD-1 antibody" refers to an antibody that specifically binds PD-1.

"Specifically binds", "specific binding" or "binds" refer to antibody binding to an antigen (e.g. PD-1) or an epitope within the antigen with greater affinity than for other antigens. Typically, the antibody binds to the antigen or the epitope within the antigen with an equilibrium dissociation constant ($K_D$) of about $1\times10^{-8}$ M or less, for example about $1\times10^{-9}$ M or less, about $1\times10^{-10}$ M or less, about $1\times10^{-11}$ M or less, or about $1\times10^{-12}$ M or less, typically with a $K_D$ that is at least one hundred-fold less than its $K_D$ for binding to a non-specific antigen (e.g., BSA, casein). The $K_D$ may be measured using standard procedures. Antibodies that specifically bind to the antigen or the epitope within the antigen may, however, have cross-reactivity to other related antigens, for example to the same antigen from other species (homologs), such as human or monkey, for example *Macaca fascicularis* (cynomolgus, cyno), *Pan troglodytes* (chimpanzee, chimp) or *Callithrix jacchus* (common marmoset, marmoset).

"Dosage" refers to the information of the amount of the therapeutic to be taken by the subject and the frequency of the number of times the therapeutic is to be taken by the subject.

"Dose" refers to the amount or quantity of the therapeutic to be taken each time.

"Relapsed" refers to the return of a disease or the signs and symptoms of a disease after a period of improvement after prior treatment with a therapeutic.

"Refractory" refers to a disease that does not respond to a treatment. A refractory disease can be resistant to a treatment before or at the beginning of the treatment, or a refractory disease can become resistant during a treatment.

"Drug substance" or "DS" refers to any substance or mixture of substances intended to be used in the manufacture of a drug (medicinal) product and that, when used in the production of a drug, becomes an active ingredient of the drug product. Such substances are intended to furnish pharmacological activity or other direct effect in the diagnosis, cure, mitigation, treatment, or prevention of disease or to affect the structure or function of the body.

"Drug product" or "DP" refers to a finished dosage form, for example, a tablet, capsule or solution that contains an active pharmaceutical ingredient (e.g. drug substance), generally, but not necessarily, in association with inactive ingredients.

"Wild-type BRAF" refers to the serine/threonine protein kinase B-raf having an amino acid sequence shown in UniProt accession number P15056.

"Mutant" refers to a polypeptide or a polynucleotide that differs from a reference polypeptide or a reference polynucleotide by one or more modifications, for example one or more substitutions, insertions or deletions. For example, the reference BRAF polypeptide is the wild-type BRAF. Mutations are indicated using well-known numbering system, e.g. V600E refers to a substitution of glutamic acid for valine at position 600.

"Immune condition" or "immune disorder" encompasses, e.g., pathological inflammation, an inflammatory disorder, and an autoimmune disorder or disease. "Immune condition" also refers to infections, persistent infections, and proliferative conditions, such as cancer, tumors, and angiogenesis, including infections, tumors, and cancers that resist eradication by the immune system.

The invention provides a method of treating a cancer, comprising providing an antagonistic anti-PD1 antibody or an antigen binding fragment thereof comprising a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6 for administration at a dosage of between about 80 mg and about 1000 mg once every two weeks, once every three weeks, once every four weeks, once every five weeks or once every six weeks to a subject diagnosed with the cancer, and administering the antagonistic anti-PD-1 antibody to the subject diagnosed with the cancer.

The invention also provides a method of treating an immune condition, comprising providing an antagonistic anti-PD1 antibody or an antigen binding fragment thereof comprising a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6 for administration at a dosage of between about 80 mg and about 1000 mg once every two weeks, once every three weeks, once every four weeks, once every five weeks or once every six weeks to a subject diagnosed with the immune condition, and administering the antagonistic anti-PD-1 antibody to the subject diagnosed with the cancer.

In some embodiments, the immune condition is a cancer.

In some embodiments, the immune condition is a viral infection, a persistent viral infection, inflammation, an inflammatory disorder or an autoimmune disorder or disease.

In some embodiments, the antagonistic anti-PD-1 antibody or the antigen binding fragment thereof is administered at a dosage of about 80 mg, about 160 mg, about 240 mg, about 320 mg, about 400 mg, about 480 mg, about 560 mg, about 720 mg, about 800 mg, about 880 mg or about 960 mg once every two weeks, once every three weeks, once every four weeks, once every five weeks or once every six weeks.

The invention also provides a method of treating a cancer, comprising administering to a subject diagnosed with the cancer an antagonistic anti-PD1 antibody or an antigen binding fragment thereof, comprising a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6 at a dose of between about 240 mg and about 480 mg.

In some embodiments, the antagonistic anti-PD-1 antibody or the antigen binding fragment thereof is administered once every two weeks, once every three weeks, once every four weeks, once every five weeks or once every six weeks.

The invention also provides a method of treating an immune condition, comprising administering to a subject diagnosed with the immune condition an antagonistic anti-PD1 antibody or an antigen binding fragment thereof, comprising a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6 at a dose of between about 240 mg and about 480 mg.

In some embodiments, the antagonistic anti-PD-1 antibody or the antigen binding fragment thereof is administered once every two weeks, once every three weeks, once every four weeks, once every five weeks or once every six weeks.

In some embodiments, the antagonistic anti-PD-1 antibody or the antigen binding fragment thereof is administered at a dosage of about 240 mg once every two weeks, once every three weeks, once every four weeks, once every five weeks or once every six weeks.

In some embodiments, the antagonistic anti-PD-1 antibody or the antigen binding fragment thereof is administered at the dosage of about 240 mg once every two weeks.

In some embodiments, the antagonistic anti-PD-1 antibody or the antigen binding fragment thereof is administered at the dosage of about 240 mg once every three weeks.

In some embodiments, the antagonistic anti-PD-1 antibody or the antigen binding fragment thereof is administered at the dosage of about 240 mg once every four weeks.

In some embodiments, the antagonistic anti-PD-1 antibody or the antigen binding fragment thereof is administered at the dosage of about 240 mg once every five weeks.

In some embodiments, the antagonistic anti-PD-1 antibody or the antigen binding fragment thereof is administered at the dosage of about 240 mg once every six weeks.

In some embodiments, the antagonistic anti-PD-1 antibody or the antigen binding fragment thereof is administered at the dosage of about 480 mg once every two weeks, once every three weeks, once every four weeks, once every five weeks or once every six weeks.

In some embodiments, the antagonistic anti-PD-1 antibody or the antigen binding fragment thereof is administered at the dosage of about 480 mg once every two weeks.

In some embodiments, the antagonistic anti-PD-1 antibody or the antigen binding fragment thereof is administered at the dosage of about 480 mg once every three weeks.

In some embodiments, the antagonistic anti-PD-1 antibody or the antigen binding fragment thereof is administered at the dosage of about 480 mg once every four weeks.

In some embodiments, the antagonistic anti-PD-1 antibody or the antigen binding fragment thereof is administered at the dosage of about 480 mg once every five weeks.

In some embodiments, the antagonistic anti-PD-1 antibody or the antigen binding fragment thereof is administered at the dosage of about 480 mg once every six weeks.

Diagnosis and staging of cancers is conducted by an oncologist using established diagnostic criteria.

In some embodiments, the cancer is a solid tumor. In some embodiments, the cancer is an advanced solid tumor. "Advanced solid tumor" refers to metastatic, unresectable, Stage III or Stage IV solid tumor.

In some embodiments, the cancer is selected from the group consisting of a lung cancer, a non-small cell lung cancer (NSCLC), a melanoma, a head and neck cancer, a bladder cancer, a gastrointestinal cancer, a gastric cancer, a gastro-esophageal junction cancer, an esophageal cancer, a liver cancer, a colorectal cancer (CRC), a colon cancer, a gallbladder cancer, a biliary tract cancer, a bladder cancer, an ovarian cancer, a fallopian tube cancer, a cervical cancer, a peritoneal cancer, an endometrial cancer, a small cell lung cancer (SCLC), a breast cancer, a pancreatic cancer, a renal cell carcinoma, a liver cancer, a Merkel cell carcinoma, a primary mediastinal B-cell lymphoma (PMBCL), a Hodgkin's lymphoma, a non-Hodgkin's lymphoma, a large diffuse B-cell cell lymphoma (DLBLC), a multiple myeloma, a glioblastoma, an urothelial cancer, a salivary cancer, a mesothelioma, an anal cancer, a prostate cancer, a basal cell carcinoma and an advanced cutaneous squamous cell carcinoma (CSCC), or any combination thereof.

In some embodiments, the cancer is selected from the group consisting of a thymus cancer, a non-small cell lung cancer (NSCLC), a small cell lung cancer (SCLC), a melanoma, a bladder cancer, a renal cancer, a gastric cancer, an esophageal cancer or a colorectal cancer (CRC).

In some embodiments, the cancer is the lung cancer.

In some embodiments, the cancer is the NSCLC

In some embodiments, the cancer is the melanoma.

In some embodiments, the cancer is the head and neck cancer.

In some embodiments, the cancer is the bladder cancer.

In some embodiments, the cancer is the gastrointestinal cancer.

In some embodiments, the cancer is the gastric cancer.

In some embodiments, the cancer is the gastro-esophageal junction cancer.

In some embodiments, the cancer is the esophageal cancer.

In some embodiments, the cancer is the liver cancer.

In some embodiments, the cancer is the CRC.

In some embodiments, the cancer is the colon cancer.

In some embodiments, the cancer is the gallbladder cancer.

In some embodiments, the cancer is the biliary tract cancer.

In some embodiments, the cancer is the ovarian cancer.

In some embodiments, the cancer is the fallopian tube cancer.

In some embodiments, the cancer is the cervical cancer.

In some embodiments, the cancer is the peritoneal cancer.

In some embodiments, the cancer is the endometrial cancer.

In some embodiments, the cancer is the SCLC.

In some embodiments, the cancer is the breast cancer.

In some embodiments, the cancer is the pancreatic cancer.

In some embodiments, the cancer is the renal cell carcinoma.

In some embodiments, the cancer is the Merkel cell carcinoma.

In some embodiments, the cancer is the PMBCL.

In some embodiments, the cancer is the Hodgkin's lymphoma.

In some embodiments, the cancer is the non-Hodgkin's lymphoma.

In some embodiments, the cancer is the DLBLC.

In some embodiments, the cancer is the multiple myeloma.

In some embodiments, the cancer is the glioblastoma.

In some embodiments, the cancer is the urothelial cancer.

In some embodiments, the cancer is the salivary cancer.

In some embodiments, the cancer is the mesothelioma.

In some embodiments, the cancer is the anal cancer.

In some embodiments, the cancer is the prostate cancer.

In some embodiments, the prostate cancer is an adenocarcinoma.

In some embodiments, the prostate cancer is a metastatic prostate cancer.

In some embodiments, the prostate cancer has metastasized to rectum, lymph node or bone, or any combination thereof.

In some embodiments, the prostate cancer is relapsed or refractory prostate cancer.

In some embodiments, the prostate cancer is a castration resistant prostate cancer.

In some embodiments, the prostate cancer is sensitive to androgen deprivation therapy.

In some embodiments, the prostate cancer is insensitive to androgen deprivation therapy.

In some embodiments, the cancer is the CSCC.

In some embodiments, the cancer is the basal cell carcinoma.

In some embodiments, the cancer is the thymus cancer.

The invention also provides a method of treating a cancer, comprising administering to a subject diagnosed with the cancer an antagonistic anti-PD1 antibody or an antigen binding fragment thereof comprising a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6 at a dosage of between about 80 mg and about 1000 mg once every two weeks, once every three weeks, once every four weeks, once every five weeks or once every six weeks, wherein the subject is PD-1 axis naïve.

The invention also provides a method of treating a cancer, comprising administering to a subject diagnosed with the cancer an antagonistic anti-PD1 antibody or an antigen binding fragment thereof comprising a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6 at a dose of between about 240 mg and about 480 mg, wherein the subject is PD-1 axis naïve.

The invention also provides a method of treating a cancer, comprising administering to a subject diagnosed with the cancer an antagonistic anti-PD1 antibody or an antigen binding fragment thereof comprising a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6 at a dosage of between about 80 mg and about 1000 mg once every two weeks, once every three weeks, once every four weeks, once every five weeks or once every six weeks, wherein the subject is PD-1 axis naïve and has received at least one prior therapeutic for the treatment of the cancer.

The invention also provides a method of treating a cancer, comprising administering to a subject diagnosed with the cancer an antagonistic anti-PD1 antibody or an antigen binding fragment thereof, comprising a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6 at a dose of between about 240 mg and about 480 mg, wherein the subject has received one, two, three or more prior therapeutics to treat the cancer.

The invention also provides a method of treating a cancer, comprising administering to a subject diagnosed with the cancer an antagonistic anti-PD1 antibody or an antigen binding fragment thereof, comprising a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6 at a dose of between about 240 mg and about 480 mg, wherein the subject is PD-1 axis naïve and has received one, two, three or more prior therapeutics to treat the cancer.

"PD-1 axis naïve" refers to a subject who has not been treated with PD-1, PD-L1 or PD-L2 antagonists. Exemplary PD-1, PD-L1 or PD-L2 antagonists are nivolumab (OPDIVO®), pembrolizumab (KEYTRUDA®), cemiplimab (Libtayo®), sintilimab, tislelizumab, tripolibamab durvalumab (IMFINZI®), atezolizumab (TECENTRIQ®), avelumab (BAVENCIO®) or envafolimab, or any other PD-1, PD-L1 or PD-L2 antagonist. Additional such antagonists are known and include those listed for example at Citeline PharmaIntelligence website.

In some embodiments, the cancer is PD-L1 positive.

In some embodiments, the cancer is PD-L1 high.

In some embodiments, PD-L1 expression in the cancer is undetermined.

"PD-L1 positive" refers to a tumor in which at least about 1% of the cells in a sample obtained from the tumor (such as a paraffin embedded formalin fixed tumor tissue sample) comprising of tumor cells and tumor-infiltrating inflammatory cells stain positive for PD-L1 surface expression.

"PD-L1 high" refers to a tumor in which at least 50% of the tumor cells or tumor-infiltrating inflammatory cells in a sample obtained from the tumor (such as a paraffin embedded formalin fixed tumor tissue sample) stain positive for PD-L1 surface expression. Commercial kits from for example from Ventana, DAKO or PharmDx may be used to assess PD-L1 positive or PD-L1 high status. In these assays, PD-L1 expression on tumor cell membrane is evaluated using anti-PD-L1 antibodies such as 28-8, 22C3, SP142, SP263 and 73-10, and a Tumor Proportion Score (TPS) indicative of percentage of PD-L1 positive tumor cells is calculated.

"PD-L1 expression in the cancer is undetermined" refers to a tumor in which PD-L1 surface expression has not been assessed.

In some embodiments, the cancer expresses a mutant BRAF.

In some embodiments, the mutant BRAF comprises a V600E mutation.

In some embodiments, the cancer expresses a wild-type BRAF.

In some embodiments, the mutant BRAF comprises one or more mutations selected from the group consisting of: V600E, V600L, R462I, 1463 S, G464E, G464R, G464V, G466A, G469A, N581 S, E586K, F595L, L597Q, L597R, L597S, L597V, A598V, T599E, V600R, K601E, S602D and A728V, and any combination thereof (see e.g. Int. Pat. Publ. No. WO2018/213302).

Mitogen-activated protein kinase (MAPK) or RAS/RAF/MEK/ERK signaling is responsible for several cell signaling pathways involved in control of proliferation, differentiation, and apoptosis. Activating mutations of the serine-threonine kinase BRAF gene is the most frequent genetic alteration in melanomas; the BRAF mutation is observed in about 50% of skin melanoma and in about 10-20% of mucosal melanoma cases (MacKiewicz and Mackiewicz, *Contem Oncol* 22:68-72, 2018). Treatment of patients harboring BRAF mutations with BRAF inhibitors (such as vemurafenib, dabrafenib and encorafenib) is associated with acquired resistance to treatment and hence MEK inhibitor such as cobimetinib, trametinib or binimetinib may be combined to the treatment regimen. MEK inhibitors have also been tested as monotherapy in BRAF mutant subjects.

BRAF status may be assessed for example from tumor biopsy samples using known methods such as sequencing.

In some embodiments, the subject has received or is ineligible to receive at least one prior therapeutic to treat the cancer.

In some embodiments, the subject has received one, two, three or more prior therapeutics to treat the cancer.

Therapeutics to treat various cancers are known, and include surgery, radiation therapy, chemotherapy, hormone therapy, immunotherapy, targeted therapy or any combination thereof.

Therapeutics to treat lung cancer, such as a non-small cell lung cancer (NSCLC) or a small cell lung cancer (SCLC) include methotrexate, paclitaxel (ABRAXANE®), afatinib (GILOTRIF®), everolimus (AFINITOR®), alectinib (ALECENSA®), pemetrexed disodium (ALIMTA®), bevacizumab (AVASTIN®), carboplatin, ceritinib (ZYKADIA®), crizotinib (XALKORI®), ramucirumab (CYRAMZA®), docetaxel, everolimus (AFINITOR®), gefitinib (IRESSA®), gemcitabine hydrochloride (GMEZAR®), pembrolizumab (KEYTRUDA®), mechlorethamine hydrochloride (MUSTARGEN®), vinorelbine tartrate (NAVELBINE®), necitumumab (PORTRAZZA®), nivolumab (OPDIVO®), carboplatin, pemetrexed disodium, ramucirumab (CYRAMZA®), osimertinib (TAGRISSO®), an anti-CTLA4 antibody, a BRAF/MEK inhibitor or interferon alpha. An exemplary anti-CTLA4 antibody is ipilimumab (YERVOY®). Exemplary BRAF/MEK inhibitors are vemurafenib (ZELBORAF®), dabrafenib, encorafenib, cobimetinib (COTELLIC®), trametinib (MEKINIST®), and binimetinib.

Therapeutics to treat melanoma include Aldesleukin, cobimetinib (COTELLIC®), dabrafenib (TAFINLAR®), dacarbazine (DTIC-Dome®), talimogene laherparepvec (IMLYGIC®), ipilimumab (YERVOY®), pembrolizumab (KEYTRUDA®), trametinib (MEKINIST®), nivolumab (OPDIVO®), Peginterferon Alfa-2b (PEG-INTRON®, SYLATRON®), recombinant interferon Alfa-2b and vemurafenib (ZELBORAF®).

Therapeutics to treat a bladder cancer include surgery, chemotherapy (such as cisplatin, gemcitabine, carboplatin, methotrexate, vinblastine, doxorubicin or any combination thereof), immunotherapy (such as weakened bacterium *bacillus* Calmette-Guerin (BCG), interferon, atezolizumab (TECENTRIQ®), nivolumab (OPDIVO®), durvalumab (IMFINZI®), avelumab (BAVENCIO®), or pembrolizumab (KEYTRUDA®) or radiation therapy. Therapeutics to treat a renal cancer include everolimus (AFINITOR®), aldesleukin, bevacizumab (AVASTIN®), axitinib (INLYTA®), cabozantinib-S-Malate (CABOMETYX®), aldesleukin (PROLEUKIN®), lenvatinib mesylate (LENVIMA®), sorafenib tosylate (NEXAVAR®), nivolumab (OPDIVO®), pazopanib hydrochloride, sorafenib tosylate, sunitinib (SUTENT®), temsirolimus (TORISEL®) and pazopanib hydrochloride (VOTRIENT®).

Therapeutics to treat a gastric cancer include surgery or chemotherapy (such as 5-fluorouracil or capecitabine, irinotecan, docetaxel or paclitaxel, or any combination thereof). Therapeutics to treat an esophageal cancer include surgery, endoscopic therapy, radiation therapy, chemotherapy or targeted immunotherapy.

Therapeutics to treat a colorectal cancer (CRC) include 5-fluorouracil and leucovorin, capecitabine (XELODA®), irinotecan (CAMPTOSAR®), cetuximab (ERBITUX®), panitumumab (VECTIBIX®), pegorafenib (STIVARGA®), a chemotherapy regimen oftrifluridine and tiptracil (LONSURF®), FOLFOX: chemotherapy regimen ofleucovorin, 5-fluorouracil and oxaliplatin (ELOXATIN®), FOLFIRI: chemotherapy regimen of leucovorin, 5-fluorouracil, and irinotecan (CAMPTOSAR®), CapeOX: chemotherapy regimen of capecitabine (XELODA®) and oxaliplatin (ELOXATIN®), FOLFOXIRI: chemotherapy regimen of leucovorin, 5-fluorouracil, oxaliplatin (ELOXATIN®), and irinotecan (CAMPTOSAR®), or any of the above individual agents or chemotherapy regiments in combination with each other or in combination with a drug that targets VEGF such as bevacizumab (AVASTIN®), ziv-aflibercept (ZALTRAP®) or ramucirumab (CYRAMZA®).

Therapeutics to treat thymus cancer include surgery, radiation therapy, a chemotherapy (such as carboplatin, cisplatin, cyclophosphamide, doxorubicin, etoposide, ifosfamide, octreotide, paclitaxel or pemetrexed, or any combination thereof) or a hormone therapy (such as corticosteroids).

Radiation therapy includes external beam radiation, intensity modulated radiation therapy (IMRT), focused radiation, and any form of radiosurgery including Gamma Knife, Cyberlaiife, Linac, and interstitial radiation (for example implanted radioactive seeds, GliaSite balloon), and/or with surgery.

Focused radiation methods that may be used include stereotactic radiosurgery, fractionated stereotactic radiosurgery, and intensity-modulated radiation therapy (IMRT). It is apparent that stereotactic radiosurgery involves the precise delivery of radiation to a tumorous tissue, while avoiding the surrounding non-tumorous, normal tissue. The dosage of radiation applied using stereotactic radiosurgery may vary typically from 1 Gy to about 30 Gy, and may encompass intermediate ranges including, for example, from 1 to 5, 10, 15, 20, 25, up to 30 Gy in dosage. Because of noninvasive fixation devices, stereotactic radiation need not be delivered in a single treatment. The treatment plan may be reliably duplicated day-to-day, thereby allowing multiple fractionated dosages of radiation to be delivered. When used to treat a tumor over time, the radiosurgery is referred to as "fractionated stereotactic radiosurgery" or FSR. In contrast, stereotactic radiosurgery refers to a one-session treatment. Fractionated stereotactic radiosurgery may result in a high therapeutic ratio, i.e., a high rate of killing of tumor cells and a low effect on normal tissue. The tumor and the normal tissue respond differently to high single dosages of radiation vs. multiple smaller dosages of radiation. Single large dosages of radiation may kill more normal tissue than several smaller dosages of radiation may. Accordingly, multiple smaller dosages of radiation can kill more tumor cells while sparing normal tissue. The dosage of radiation applied using fractionated stereotactic radiation may vary from range from 1 Gy to about 50 Gy, and may encompass intermediate ranges including, for example, from 1 to 5, 10, 15, 20, 25, 30, 40, up to 50 Gy in hypofractionated dosages. Intensity-modulated radiation therapy (IMRT) may also be used. IMRT is an advanced mode of high-precision three-dimensional conformal radiation therapy (3DCRT), which uses computer-controlled linear accelerators to deliver precise radiation dosages to a malignant tumor or specific areas within the tumor, the profile of each radiation beam is shaped to fit the profile of the target from a beam's eye view (BEV) using a multileaf collimator (MLC), thereby producing a number of beams. IMRT allows the radiation dosage to conform more precisely to the three-dimensional (3-D) shape of the tumor by modulating the intensity of the radiation beam in multiple small volumes. Accordingly, IMRT allows higher radiation dosages to be focused to regions within the tumor while minimizing the dosage to surrounding normal critical structures. IMRT improves the ability to conform the treatment volume to concave tumor shapes, for example, when the tumor is wrapped around a vulnerable structure, such as the spinal cord or a major organ or blood vessel. Suitable radiation sources for use as a cell conditioner include both solids and liquids.

In some embodiments the one, two, three or more prior therapeutics to treat the cancer are an anti-CTLA4 antibody, ipilimumab (YERVOY®), BRAF/MEK inhibitor, chemotherapy or interferon alpha, or any combination thereof.

"BRAF/MEK inhibitor" refers to a molecule, such as a small molecule, that inhibits at least one biological activity mediated by BRAF and/or MEK. The inhibition may be at least about 20%, 30%, 40%, 45%, 50%, 55%, 60%, 65%, 70%, 75%, 80%, 85%, 90%, 95%, or 100% greater than in the absence of the inhibitor (e.g., negative control), or when the inhibition is statistically significant when compared to a control. Typical biological activities mediated by BRAF and/or MEK are protein phosphorylation, cell proliferation, cell survival and apoptosis, which can be measured using standard methods.

Exemplary BRAF inhibitors are vemurafenib (ZELBORAF®), pazopanib, dabrafenib and encorafenib.

Exemplary MEK inhibitors are cobimetinib (COTELLIC®), trametinib (MEKINIST®), and binimetinib.

In some embodiments, the subject is resistant, refractory or resistant and refractory to the one, two, three or more prior therapeutics to treat the cancer, or any combination thereof.

In some embodiments, the subject is resistant, refractory or resistant and refractory to an anti-CTLA4 antibody, ipilimumab, BRAF/MEK inhibitor, chemotherapy or interferon alpha, or any combination thereof.

Various qualitative and/or quantitative methods may be used to determine relapse or refractory nature of the disease. Symptoms that may be associated with relapse or resistance are, for example, a decline or plateau of the well-being of the patient or re-establishment or worsening of various symptoms associated with solid tumors, and/or the spread of cancerous cells in the body from one location to other organs, tissues or cells.

In some embodiments, the antagonistic anti-PD-1 antibody or the antigen binding fragment thereof is administered or provided for administration in a pharmaceutical composition comprising between about 10 mg/ml to about 30 mg/ml of the antagonistic anti-PD-1 antibody or the antigen binding fragment thereof and one or more pharmaceutically acceptable excipients.

"Pharmaceutically acceptable excipients" refer to solvents, dispersion media, coatings, antibacterial and antifungal agents, isotonic and absorption delaying agents, and the like that are physiologically compatible, such as salts, buffers, antioxidants, saccharides, aqueous or non-aqueous carriers, preservatives, wetting agents, surfactants or emulsifying agents, or combinations thereof.

Exemplary buffers that may be used are acetic acid, citric acid, formic acid, succinic acid, phosphoric acid, carbonic acid, malic acid, aspartic acid, histidine, boric acid, Tris buffers, HEPPSO and HEPES.

Exemplary antioxidants that may be used are ascorbic acid, methionine, cysteine hydrochloride, sodium bisulfate, sodium metabisulfite, sodium sulfite, lecithin, citric acid, ethylenediamine tetraacetic acid (EDTA), sorbitol and tartaric acid.

Exemplary amino acids that may be used are histidine, isoleucine, methionine, glycine, arginine, lysine, L-leucine, tri-leucine, alanine, glutamic acid, L-threonine, and 2-phenylamine.

Exemplary surfactants that may be used are polysorbates (e.g., polysorbate-20 or polysorbate-80); polyoxamers (e.g., poloxamer 188); Triton; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUA™ series (Mona Industries, Inc., Paterson, N.J.), polyethyl glycol, polypropyl glycol, and copolymers of ethylene and propylene glycol (e.g., PLURONICS™, PF68, etc).

Exemplary preservatives that may be used are phenol, m-cresol, p-cresol, o-cresol, chlorocresol, benzyl alcohol, phenylmercuric nitrite, phenoxyethanol, formaldehyde, chlorobutanol, magnesium chloride, alkylparaben (methyl, ethyl, propyl, butyl and the like), benzalkonium chloride, benzethonium chloride, sodium dehydroacetate and thimerosal, or mixtures thereof.

Exemplary saccharides that may be used are monosaccharides, disaccharides, trisaccharides, polysaccharides, sugar alcohols, reducing sugars, nonreducing sugars such as glucose, sucrose, trehalose, lactose, fructose, maltose, dextran, glycerin, dextran, erythritol, glycerol, arabitol, sylitol, sorbitol, mannitol, mellibiose, melezitose, raffinose, mannotriose, stachyose, maltose, lactulose, maltulose, glucitol, maltitol, lactitol or iso-maltulose.

Exemplary salts that may be used are acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like. An exemplary salt is sodium chloride.

The amounts of pharmaceutically acceptable carrier(s) in the pharmaceutical compositions may be determined experimentally based on the activities of the carrier(s) and the desired characteristics of the formulation, such as stability and/or minimal oxidation.

In some embodiments, the pharmaceutical composition comprises histidine.

In some embodiments, the pharmaceutical composition comprises histidine at a concentration of from about 1 mM to about 50 mM.

In some embodiments, the pharmaceutical composition comprises histidine at a concentration of from about 5 mM to about 50 mM.

In some embodiments, the pharmaceutical composition comprises histidine at a concentration of from about 5 mM to about 30 mM.

In some embodiments, the pharmaceutical composition comprises histidine at a concentration of from about 5 mM to about 20 mM.

In some embodiments, the pharmaceutical composition comprises histidine at a concentration of from about 5 mM to about 15 mM.

In some embodiments, the pharmaceutical composition comprises histidine at a concentration of from about 5 mM to about 10 mM.

In some embodiments, the pharmaceutical composition comprises histidine at a concentration of about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM or about 50 mM.

In some embodiments, the pharmaceutical composition comprises histidine at a concentration of about 10 mM.

In some embodiments, the pharmaceutical composition comprises sucrose.

In some embodiments, the pharmaceutical composition comprises sucrose at a concentration of from about 1% (w/v) to about 20% (w/v).

In some embodiments, the pharmaceutical composition comprises sucrose at a concentration of from about 2% (w/v) to about 18% (w/v).

In some embodiments, the pharmaceutical composition comprises sucrose at a concentration of from about 4% (w/v) to about 16% (w/v).

In some embodiments, the pharmaceutical composition comprises sucrose at a concentration of from about 6% (w/v) to about 14% (w/v).

In some embodiments, the pharmaceutical composition comprises sucrose at a concentration of from about 6% (w/v) to about 12% (w/v).

In some embodiments, the pharmaceutical composition comprises sucrose at a concentration of from about 6% (w/v) to about 10% (w/v).

In some embodiments, the pharmaceutical composition comprises sucrose at a concentration of about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), about 11% (w/v), about 12% (w/v), about 13% (w/v), about 14% (w/v), about 15% (w/v), about 16% (w/v), about 17% (w/v), about 18% (w/v), about 19% (w/v) or about 20% (w/v), In some embodiments, the pharmaceutical composition comprises sucrose at a concentration of about 8% (w/v).

In some embodiments, the pharmaceutical composition comprises polysorbate-20.

In some embodiments, the pharmaceutical composition comprises polysorbate-20 (PS-20) at a concentration of from about 0.01% (w/v) to about 0.1% (w/v).

In some embodiments, the pharmaceutical composition comprises polysorbate-20 (PS-20) at a concentration of from about 0.01% (w/v) to about 0.08% (w/v).

In some embodiments, the pharmaceutical composition comprises polysorbate-20 (PS-20) at a concentration of from about 0.02% (w/v) to about 0.06% (w/v).

In some embodiments, the pharmaceutical composition comprises polysorbate-20 (PS-20) at a concentration of about 0.01% (w/v), about 0.02% (w/v), about 0.03% (w/v), about 0.04% (w/v), about 0.05% (w/v), about 0.06% (w/v), about 0.07% (w/v), about 0.08% (w/v), about 0.09% (w/v) or about 0.1% (w/v).

In some embodiments, the pharmaceutical composition comprises polysorbate-20 (PS-20) at a concentration of about 0.04% (w/v).

In some embodiments, the pharmaceutical composition comprises EDTA.

In some embodiments, the pharmaceutical composition comprises EDTA at a concentration of from about 1 µg/ml to about 50 µg/ml.

In some embodiments, the pharmaceutical composition comprises EDTA at a concentration of from about 5 µg/ml to about 50 µg/ml.

In some embodiments, the pharmaceutical composition comprises EDTA at a concentration of from about 5 µg/ml to about 30 µg/ml.

In some embodiments, the pharmaceutical composition comprises EDTA at a concentration of from about 5 µg/ml to about 20 µg/ml.

In some embodiments, the pharmaceutical composition comprises EDTA at a concentration of from about 5 µg/ml to about 15 µg/ml.

In some embodiments, the pharmaceutical composition comprises EDTA at a concentration of from about 5 µg/ml to about 10 µg/ml.

In some embodiments, the pharmaceutical composition comprises EDTA at a concentration of about 1 µg/ml, about 2 µg/ml, about 3 µg/ml, about 4 µg/ml, about 5 µg/ml, about 6 µg/ml, about 7 µg/ml, about 8 µg/ml, about 9 µg/ml, about 10 µg/ml, about 11 µg/ml, about 12 µg/ml, about 13 µg/ml, about 14 µg/ml, about 15 µg/ml, about 16 µg/ml, about 17 µg/ml, about 18 µg/ml, about 19 µg/ml, about 20 µg/ml, about 21 µg/ml, about 22 µg/ml, about 23 µg/ml, about 24

µg/ml, about 25 µg/ml, about 26 µg/ml, about 27 µg/ml, about 28 µg/ml, about 29 µg/ml, about 30 µg/ml, about 31 µg/ml, about 32 µg/ml, about 33 µg/ml, about 34 µg/ml, about 35 µg/ml, about 36 µg/ml, about 37 µg/ml, about 38 µg/ml, about 39 µg/ml, about 40 µg/ml, about 41 µg/ml, about 42 µg/ml, about 43 µg/ml, about 44 µg/ml, about 45 µg/ml, about 46 µg/ml, about 47 µg/ml, about 48 µg/ml, about 49 µg/ml or about 50 µg/ml.

In some embodiments, the pharmaceutical composition comprises EDTA at a concentration of about 20 µg/ml.

In some embodiments, the antagonistic anti-PD-1 antibody or the antigen binding fragment thereof is administered or provided for administration in a pharmaceutical composition comprising between about 10 mg/ml to about 30 mg/ml of the antagonistic anti-PD-1 antibody or the antigen binding fragment thereof, histidine, sucrose, polysorbate-20 and EDTA.

In some embodiments, the antagonistic anti-PD-1 antibody or the antigen binding fragment thereof is administered or provided for administration in a pharmaceutical composition comprising between about 10 mg/ml to about 30 mg/ml of the antagonistic anti-PD-1 antibody or the antigen binding fragment thereof, about 10 mM histidine, about 8.0% (w/v) sucrose, about 0.04% (w/v) polysorbate-20 and about 20 µg/ml EDTA at pH 6.5.

In some embodiments, the antagonistic anti-PD-1 antibody or the antigen binding fragment thereof is administered or provided for administration in a pharmaceutical composition comprising about 10 mg/ml of the antagonistic anti-PD-1 antibody or the antigen binding fragment thereof, about 10 mM histidine, about 8.0% (w/v) sucrose, about 0.04% (w/v) polysorbate-20 and about 20 µg/ml EDTA at pH 6.5.

In some embodiments, the antagonistic anti-PD-1 antibody or the antigen binding fragment thereof is administered or provided for administration in a pharmaceutical composition comprising about 30 mg/ml of the antagonistic anti-PD-1 antibody or the antigen binding fragment thereof, about 10 mM histidine, about 8.0% (w/v) sucrose, about 0.04% (w/v) polysorbate-20 and about 20 µg/ml EDTA at pH 6.5.

In some embodiments, the antagonistic anti-PD-1 antibody or the antigen binding fragment thereof is provided for administration as a lyophilized formulation comprising between about 90 mg and about 240 mg of the antagonistic anti-PD-1 antibody or the antigen binding fragment thereof and one or more pharmaceutically acceptable excipients.

In some embodiments, the antagonistic anti-PD-1 antibody or the antigen binding fragment thereof is provided for administration as a lyophilized formulation comprising about 90 mg of the antagonistic anti-PD-1 antibody or the antigen binding fragment thereof and one or more pharmaceutically acceptable excipients.

In some embodiments, the antagonistic anti-PD-1 antibody or the antigen binding fragment thereof is provided for administration as a lyophilized formulation comprising about 240 mg of the antagonistic anti-PD-1 antibody or the antigen binding fragment thereof and one or more pharmaceutically acceptable excipients.

In some embodiments, the lyophilized formulation, once reconstituted, comprises about 30 mg/ml of the antagonistic anti-PD-1 antibody or the antigen binding fragment thereof, about 10 mM histidine, about 8.0% (w/v) sucrose, about 0.04% (w/v) polysorbate-20 and about 20 µg/ml EDTA at pH 6.5.

In some embodiments, the pharmaceutical composition is a liquid.

In some embodiments, the pharmaceutical composition is a frozen liquid.

In some embodiments, the pharmaceutical composition is a lyophilized powder.

In some embodiments, the pharmaceutical composition is provided in a volume of between about 1 ml to about 20 ml.

In some embodiments, the pharmaceutical composition is provided in a volume of about 1 ml, about 2 ml, about 3 ml, about 4 ml, about 5 ml, about 6 ml, about 7 ml, about 8 ml, about 9 ml, about 10 ml, about 11 ml, about 12 ml, about 13 ml, about 14 ml, about 15 ml, about 16 ml, about 17 ml, about 18 ml, about 19 ml or about 20 ml.

In some embodiments, the pharmaceutical composition is provided or reconstituted in a volume of about 3 ml.

In some embodiments, the pharmaceutical composition is provided or reconstituted in a volume of about 3.3 ml.

In some embodiments, the pharmaceutical composition is provided or reconstituted in a volume of about 8 ml.

In some embodiments, the pharmaceutical composition is provided or reconstituted in a volume of about 8.6 ml.

In some embodiments, the pharmaceutical composition is provided or reconstituted in a volume of about 8.8 ml.

In some embodiments, the antagonistic anti-PD-1 antibody or the antigen binding fragment thereof is administered or provided for administration in a pharmaceutical composition comprising about 10 mg/ml of the antagonistic anti-PD-1 antibody or the antigen binding fragment thereof, about 10 mM histidine, about 8.0% (w/v) sucrose, about 0.04% (w/v) polysorbate-20 and about 20 µg/ml EDTA at pH 6.5 in a volume of about 3.3 ml.

In some embodiments, the antagonistic anti-PD-1 antibody is cetrelimab. Cetrelimab is an IgG4/κ antibody characterized by following amino acid sequences: the HCDR1 of SEQ ID NO: 1, the HCDR2 of SEQ ID NO: 2, the HCDR3 of SEQ ID NO: 3, the LCDR1 of SEQ ID NO: 4, the LCDR2 of SEQ ID NO: 5, the LCDR6 of SEQ ID NO: 6, the VH of SEQ ID NO: 7, the VL of SEQ ID NO: 8, the HC of SEQ ID NO: 9 and the LC of SEQ ID NO: 10.

In some embodiments, the antagonistic anti-PD-1 antibody or the antigen binding fragment thereof is administered or provided for administration as a lyophilized formulation comprising about 90 mg of the antagonistic anti-PD-1 antibody or the antigen binding fragment thereof and one or more pharmaceutically acceptable excipients that upon reconstitution into about 3.3 ml comprises about 30 mg/ml of the antagonistic anti-PD-1 antibody or the antigen binding fragment thereof, about 10 mM histidine, about 8.0% (w/v) sucrose, about 0.04% (w/v) polysorbate-20 and about 20 µg/ml EDTA at pH 6.5.

In some embodiments, the antagonistic anti-PD-1 antibody is cetrelimab.

In some embodiments, the antagonistic anti-PD-1 antibody or the antigen binding fragment thereof is administered or provided for administration as a lyophilized formulation comprising about 240 mg of the antagonistic anti-PD-1 antibody or the antigen binding fragment thereof and one or more pharmaceutically acceptable excipients that upon reconstitution into about 8.6 ml comprises about 30 mg/ml of the antagonistic anti-PD-1 antibody or the antigen binding fragment thereof, about 10 mM histidine, about 8.0% (w/v) sucrose, about 0.04% (w/v) polysorbate-20 and about 20 µg/ml EDTA at pH 6.5.

In some embodiments, the antagonistic anti-PD-1 antibody is cetrelimab.

"Lyophilization," "lyophilized," and "freeze-dried" refer to a process by which the material to be dried is first frozen and then the ice or frozen solvent is removed by sublimation in a vacuum environment. An excipient may be included in pre-lyophilized formulations to enhance stability of the lyophilized product upon storage.

"Reconstitute", "reconstituted" or "reconstitution" refers to dissolving the lyophilized formulation in a diluent so that the protein in the lyophilized formulation is dispersed in the reconstituted formulation. The reconstituted formulation is suitable for administration, e.g. parenteral administration), and may optionally be suitable for subcutaneous administration. In some embodiments, the diluent is sterile water for injection (sWFI).

"Pharmaceutical composition", "pharmaceutical formulation" or "formulation" refers to a combination of an active ingredient (e.g. the anti-PD-1 antibody) and one or more excipients in either liquid or solid (e.g. lyophilized) form.

In some embodiments, the antagonistic anti-PD-1 antibody or the antigen binding fragment thereof is administered by an intravenous infusion.

In some embodiments, the antagonistic anti-PD-1 antibody or the antigen binding fragment thereof is diluted into a volume of between about 100 ml and 1000 ml prior to administration.

In some embodiments, duration of the intravenous infusion is between about 20 minutes and about 80 minutes.

In some embodiments, duration of the intravenous infusion is about 20, about 30, about 40, about 50, about 60, about 70 or about 80 minutes.

In some embodiments, the antagonistic anti-PD-1 antibody or the antigen binding fragment thereof is administered by one or more subcutaneous injections.

The invention also provides a method of treating a cancer, comprising administering to a subject diagnosed with the cancer an antagonistic anti-PD1 antibody or an antigen binding fragment thereof comprising a heavy chain complementarity determining region 1 (HCDR1) of SEQ ID NO: 1, a HCDR2 of SEQ ID NO: 2, a HCDR3 of SEQ ID NO: 3, a light chain complementarity determining region 1 (LCDR1) of SEQ ID NO: 4, a LCDR2 of SEQ ID NO: 5 and a LCDR3 of SEQ ID NO: 6 at a dosage of between about 80 mg and about 1000 mg once every two weeks, once every three weeks, once every four weeks, once every five weeks or once every six weeks, wherein the subject is PD-1 axis naïve, has received and/or is ineligible for at least one prior therapeutic for the treatment of the cancer, or any combination thereof.

In some embodiments, the method achieves an overall response rate (ORR) of at least 15% in a group of subjects diagnosed with the cancer. ORR is defined as a percentage of subjects achieving partial response (PR) or complete response (CR). ORR may be assessed per the Response Evaluation Criteria in Solid Tumors (RECIST) v1.1 or per irRC in subjects with selected advanced solid tumors (irRC=–IRRC=Immune-Related Response Criteria from Wolchok et al. (2009) *Clin Cancer Res* 15: 7412-20).

In some embodiments, the ORR of at least about 15% is achieved after a median duration of treatment of about 1½ months or more.

In some embodiments, the ORR of at least about 15% is achieved after a median duration of treatment of about 1 months or more, about 2 months or more, about 3 months or more, about 4 months or more, about 5 months or more, about 6 months or more, about 7 months or more, about 8 months or more, about 9 months or more, about 10 months or more, about 11 months or more, or about 12 months or more.

In some embodiments, the method achieves an ORR of at least about 19% in the group of subjects diagnosed with the cancer.

In some embodiments, the cancer is the NSCLC.

In some embodiments, the method achieves an ORR of at least about 30% in a group of subjects diagnosed with PD-L1 high NSCLC or an ORR of at least about 25% in a group of subjects whose PD-L1 expression in the cancer is undetermined.

In some embodiments, the method achieves an ORR of at least about 35% in the group of subjects diagnosed with PD-L1 high NSCLC.

In some embodiments, the cancer is the melanoma.

In some embodiments, the method achieves or an ORR of at least about 25% in a group of subjects diagnosed with melanoma.

In some embodiments, the melanoma is a non-uveal melanoma.

In some embodiments, the method achieves an ORR of at least about 30% in a group of subjects diagnosed with the non-uveal melanoma.

In some embodiments, the method achieves an ORR of at least about 35% in a group of subjects diagnosed with MSI-H CRC.

In some embodiments, the method achieves an ORR of at least about 35% in a group of subjects diagnosed with dMMR CRC.

The invention also provides a method of treating a colorectal cancer (CRC), comprising administering to a subject diagnosed with the CRC an antagonistic anti-PD1 antibody or an antigen binding fragment thereof comprising a HCDR1 of SEQ ID NO: 1, a HCDR2 of SEQ ID NO: 2, a HCDR3 of SEQ ID NO: 3, a LCDR1 of SEQ ID NO: 4, a LCDR2 of SEQ ID NO: 5 and a LCDR3 of SEQ ID NO: 6 for a time sufficient to treat the CRC.

The invention also provides a method of treating a mismatch repair-deficient (dMMR) colorectal cancer (CRC) or high-level microsatellite instability (MSI-H) CRC, comprising administering to a subject diagnosed with the dMMR CRC or MSI-H CRC an antagonistic anti-PD 1 antibody or an antigen binding fragment thereof comprising a HCDR1 of SEQ ID NO: 1, a HCDR2 of SEQ ID NO: 2, a HCDR3 of SEQ ID NO: 3, a LCDR1 of SEQ ID NO: 4, a LCDR2 of SEQ ID NO: 5 and a LCDR3 of SEQ ID NO: 6 for a time sufficient to treat the dMMR CRC or the MSI-H CRC.

Approximately 15% of colorectal carcinomas (CRC) have deficient DNA mismatch repair (dMMR) which is characterized by microsatellite instability (MSI) in the tumor. Tumors with the dMMR/MSI result typically from germline mutation in one of the MMR genes or somatic inactivation of the same pathway. dMMR/MSI tumors include hereditary non-polyposis colorectal cancer (HNPCC), also called Lynch syndrome and sporadic MSI-H CRC. Lynch syndrome is caused by germline mutations in MMR genes MLH1, MSH2, MSH6 or PMS2, or epigenetic inactivation of MSH2. Sporadic MSI-H CRCs are frequently caused by methylation of MLH1 promoter. A subset of MSI-H tumors has no alterations in the MMR genes themselves, but instead overexpress various miRNAs that may silence the MMR genes. For example, miRNA-21 found overexpressed in MSI-H CRC targets MSH2 and MSH6 mRNA.

MSI-H CRC can be detected using polymerase chain reaction (PCR) of tumor tissue samples detecting stability of microsatellite markers. CRC is classified as MSI-H if instability is shown in 30% or more of microsatellite markers with at least 5 markers evaluated. The National Cancer Institute has recommended a panel of 5 microsatellites for MSI screening: BAT25 and BAT26 (mononucleotide repeats), D2S123, D5S346, and D17S250 (dinucleotide repeats). dMMR can be detected using immunohistochemistry of tumor tissues. CRC is classified as dMMR if loss of at least one MMR genes MLH1, MSH2, MSH6 or PMS2 is detected in the tumor tissue.

In some embodiments, the CRC is a stage II CRC or a stage III CRC. CRC staging is known, using for example the American Joint Committee on Cancer (AJCC) TNM system and diagnosis by an oncologist.

In some embodiments, the subject diagnosed with CRC is refractory to treatment with fluoropyrimidine, oxaliplatin or irinotecan, or any combination thereof.

In some embodiments, the subject diagnosed with CRC has a relapsed tumor after treatment with fluoropyrimidine, oxaliplatin or irinotecan, or any combination thereof.

Various qualitative and/or quantitative methods may be used to determine relapse or refractory nature of the disease. Symptoms that may be associated with relapse or refractory disease are, for example, a decline or plateau of the well-being of the patient or re-establishment or worsening of various symptoms associated with tumors, and/or the spread of cancerous cells in the body from one location to other organs, tissues or cells.

The invention also provides a method of treating a thymus cancer, comprising administering to a subject diagnosed with the thymus cancer an antagonistic anti-PD1 antibody or an antigen binding fragment thereof comprising a HCDR1 of SEQ ID NO: 1, a HCDR2 of SEQ ID NO: 2, a HCDR3 of SEQ ID NO: 3, a LCDR1 of SEQ ID NO: 4, a LCDR2 or SEQ ID NO: 5 and a LCDR3 of SEQ ID NO: 6 for a time sufficient to treat the thymus cancer.

The invention also provides a method of treating a thymus cancer, comprising administering to a subject diagnosed with the thymus cancer an antagonistic anti-PD1 antibody or an antigen binding fragment thereof comprising a heavy chain variable region (VH) of SEQ ID NO: 7 and a light chain variable region (VL) of SEQ ID NO: 8 for a time sufficient to treat the thymus cancer.

The invention also provides a method of treating a thymus cancer, comprising administering to a subject diagnosed with the thymus cancer an antagonistic anti-PD1 antibody comprising a heavy chain (HC) of SEQ ID NO: 9 and a light chain (LC) of SEQ ID NO: 10 for a time sufficient to treat the thymus cancer.

The invention also provides a method of treating a thymus cancer, comprising administering to a subject diagnosed with the thymus cancer an antagonistic anti-PD1 antibody comprising a heavy chain (HC) of SEQ ID NO: 9 and a light chain (LC) of SEQ ID NO: 10 at a dosage of between about 80 mg and about 1000 mg once every two weeks, once every three weeks, once every four weeks, once every five weeks or once every six weeks.

The invention also provides a method of treating a thymus cancer, comprising administering to a subject diagnosed with the thymus cancer an antagonistic anti-PD1 antibody comprising a heavy chain (HC) of SEQ ID NO: 9 and a light chain (LC) of SEQ ID NO: 10 at a dosage of about 80 mg once every two weeks, once every three weeks, once every four weeks, once every five weeks or once every six weeks.

The invention also provides a method of treating a thymus cancer, comprising administering to a subject diagnosed with the thymus cancer an antagonistic anti-PD1 antibody comprising a heavy chain (HC) of SEQ ID NO: 9 and a light chain (LC) of SEQ ID NO: 10 at a dosage of about 160 mg once every two weeks, once every three weeks, once every four weeks, once every five weeks or once every six weeks.

The invention also provides a method of treating a thymus cancer, comprising administering to a subject diagnosed with the thymus cancer an antagonistic anti-PD1 antibody comprising a heavy chain (HC) of SEQ ID NO: 9 and a light chain (LC) of SEQ ID NO: 10 at a dosage of about 240 mg once every two weeks, once every three weeks, once every four weeks, once every five weeks or once every six weeks.

The invention also provides a method of treating a thymus cancer, comprising administering to a subject diagnosed with the thymus cancer an antagonistic anti-PD1 antibody comprising a heavy chain (HC) of SEQ ID NO: 9 and a light chain (LC) of SEQ ID NO: 10 at a dosage of about 320 mg once every two weeks, once every three weeks, once every four weeks, once every five weeks or once every six weeks.

The invention also provides a method of treating a thymus cancer, comprising administering to a subject diagnosed with the thymus cancer an antagonistic anti-PD1 antibody comprising a heavy chain (HC) of SEQ ID NO: 9 and a light chain (LC) of SEQ ID NO: 10 at a dosage of about 400 mg once every two weeks, once every three weeks, once every four weeks, once every five weeks or once every six weeks.

The invention also provides a method of treating a thymus cancer, comprising administering to a subject diagnosed with the thymus cancer an antagonistic anti-PD1 antibody comprising a heavy chain (HC) of SEQ ID NO: 9 and a light chain (LC) of SEQ ID NO: 10 at a dosage of about 480 mg once every two weeks, once every three weeks, once every four weeks, once every five weeks or once every six weeks.

The invention also provides a method of treating a thymus cancer, comprising administering to a subject diagnosed with the thymus cancer an antagonistic anti-PD1 antibody comprising a heavy chain (HC) of SEQ ID NO: 9 and a light chain (LC) of SEQ ID NO: 10 at a dosage of about 560 mg once every two weeks, once every three weeks, once every four weeks, once every five weeks or once every six weeks.

The invention also provides a method of treating a thymus cancer, comprising administering to a subject diagnosed with the thymus cancer an antagonistic anti-PD1 antibody comprising a heavy chain (HC) of SEQ ID NO: 9 and a light chain (LC) of SEQ ID NO: 10 at a dosage of about 720 mg once every two weeks, once every three weeks, once every four weeks, once every five weeks or once every six weeks.

The invention also provides a method of treating a thymus cancer, comprising administering to a subject diagnosed with the thymus cancer an antagonistic anti-PD1 antibody comprising a heavy chain (HC) of SEQ ID NO: 9 and a light chain (LC) of SEQ ID NO: 10 at a dosage of about 800 mg once every two weeks, once every three weeks, once every four weeks, once every five weeks or once every six weeks.

The invention also provides a method of treating a thymus cancer, comprising administering to a subject diagnosed with the thymus cancer an antagonistic anti-PD1 antibody comprising a heavy chain (HC) of SEQ ID NO: 9 and a light chain (LC) of SEQ ID NO: 10 at a dosage of about 880 mg once every two weeks, once every three weeks, once every four weeks, once every five weeks or once every six weeks.

The invention also provides a method of treating a thymus cancer, comprising administering to a subject diagnosed with the thymus cancer an antagonistic anti-PD1 antibody comprising a heavy chain (HC) of SEQ ID NO: 9 and a light chain (LC) of SEQ ID NO: 10 at a dosage of about 960 mg once every two weeks, once every three weeks, once every four weeks, once every five weeks or once every six weeks.

In some embodiments, the thymus cancer is a thymoma.

In some embodiments, the thymoma is a type A thymoma.

In some embodiments, the thymoma is a type AB thymoma.

In some embodiments, the thymoma is a type B1 thymoma.

In some embodiments, the thymoma is a type B2 thymoma.

In some embodiments, the thymoma is a type B3 thymoma.

In some embodiments, the thymus cancer is a thymic carcinoma.

In some embodiments, the thymic carcinoma is a low grade thymic carcinoma.

In some embodiments, the thymic carcinoma is high grade thymic carcinoma.

In some embodiments, the thymus cancer is a metastatic thymic cancer.

In some embodiments, the thymus cancer has metastasized to lung, lymph node, heart or bone.

In some embodiments, the subject has been treated with surgery, radiation therapy, a chemotherapy or a hormone therapy.

In some embodiments, the subject has been treated with carboplatin, cisplatin, cyclophosphamide, doxorubicin, etoposide, ifosfamide, octreotide, paclitaxel or pemetrexed, or any combination thereof.

Thymus cancer may be staged for example according to the American Society of Clinical Oncology (ASCO) staging system.

In some embodiments, the antagonistic anti-PD-1 antibody or the antigen binding fragment thereof comprises a heavy chain variable region (VH) of SEQ ID NO: 7 and a light chain variable region (VL) or SEQ ID NO: 8.

In some embodiments, the antagonistic anti-PD-1 antibody or the antigen binding fragment thereof is an IgG1, an IgG2, and IgG3 or an IgG4 isotype.

In some embodiments, the antagonistic anti-PD-1 antibody or the antigen binding fragment thereof is an IgG4 isotype.

In some embodiments, the antagonistic anti-PD-1 antibody or the antigen binding fragment thereof is an IgG4 isotype and comprises proline at position 228, residue numbering according to the EU Index.

In some embodiments, the antagonistic anti-PD-1 antibody is a nG4m(a) allotype.

In some embodiments, the antagonistic anti-PD-1 antibody or an antigen binding fragment thereof has at least one substitution in an Fc region to modulate antibody effector functions or antibody half-life.

In some embodiments, the antagonistic anti-PD-1 antibody comprises a heavy chain of SEQ ID NO: 9 and a light chain of SEQ ID NO: 10.

The invention also provides a pharmaceutical composition comprising about 10 mg/ml of the antagonistic anti-PD-1 antibody comprising the HC of SEQ ID NO: 9 and the LC of SEQ ID NO: 10, about 10 mM histidine, about 8.0% (w/v) sucrose, about 0.04% (w/v) polysorbate 20 and about 20 µg/ml and EDTA at pH 6.5.

```
                                              SEQ ID NO: 1
SYAIS

SEQ ID NO: 2
GIIPIFDTANYAQKFQG

SEQ ID NO: 3
PGLAAAYDTGSLDY

SEQ ID NO: 4
RASQSVRSYLA
```

-continued
```
                                              SEQ ID NO: 5
DASNRAT

SEQ ID NO: 6
QQRNYWPLT

SEQ ID NO: 7
QVQLVQSGAEVKKPGSSVKVSCKASGGTFSSYAISWVRQAPGQGLEWMGG

IIPIFDTANYAQKFQGRVTITADESTSTAYMELSSLRSEDTAVYYCARPG

LAAAYDTGSLDYWGQGTLVTVSS

SEQ ID NO: 8
EIVLTQSPATLSLSPGERATLSCRASQSVRSYLAWYQQKPGQAPRLLIYD

ASNRATGIPARFSGSGSGTDFTLTISSLEPEDFAVYYCQQRNYWPLTFGQ

GTKVEIK

SEQ ID NO: 9
QVQLVQSGAEVKKPGSSVKVSCKASGGTFSSYAISWVRQAPGQGLEWMGG

IIPIFDTANYAQKFQGRVTITADESTSTAYMELSSLRSEDTAVYYCARPG

LAAAYDTGSLDYWGQGTLVTVSSASTKGPSVFPLAPCSRSTSESTAALGC

LVKDYFPEPVTVSWNSGALTSGVHTFPAVLQSSGLYSLSSVVTVPSSSLG

TKTYTCNVDHKPSNTKVDKRVESKYGPPCPPCPAPEFLGGPSVFLFPPKP

KDTLMISRTPEVTCVVVDVSQEDPEVQFNWYVDGVEVHNAKTKPREEQFN

STYRVVSVLTVLHQDWLNGKEYKCKVSNKGLPSSIEKTISKAKGQPREPQ

VYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLG

K

SEQ ID NO: 10
EIVLTQSPATLSLSPGERATLSCRASQSVRSYLAWYQQKPGQAPRLLIYD

ASNRATGIPARFSGSGSGTDFTLTISSLEPEDFAVYYCQQRNYWPLTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

The invention also provides a pharmaceutical composition comprising between about 10 mg/ml and about 30 mg/ml cetrelimab, about 10 mM histidine, about 8.0% (w/v) sucrose, about 0.04% (w/v) polysorbate-20 and about 20 µg/ml EDTA at pH 6.5;

about 10 mg/ml cetrelimab, about 10 mM histidine, about 8.0% (w/v) sucrose, about 0.04% (w/v) polysorbate-20 and about 20 µg/ml EDTA at pH 6.5;

about 30 mg/ml cetrelimab, about 10 mM histidine, about 8.0% (w/v) sucrose, about 0.04% (w/v) polysorbate-20 and about 20 µg/ml EDTA at pH 6.5;

a lyophilized formulation comprising between about 90 mg and about 240 mg of cetrelimab and one or more pharmaceutically acceptable excipients;

a lyophilized formulation comprising about 90 mg of cetrelimab and one or more pharmaceutically acceptable excipients; or a lyophilized formulation comprising about 240 mg of cetrelimab and one or more pharmaceutically acceptable excipients.

In some embodiments, the lyophilized formulation, once reconstituted, comprises about 30 mg/ml cetrelimab, about 10 mM histidine, about 8.0% (w/v) sucrose, about 0.04% (w/v) polysorbate-20 and about 20 µg/ml EDTA at pH 6.5.

The invention also provides a drug product comprising between about 10 mg/ml and about 30 mg/ml cetrelimab, about 10 mM histidine, about 8.0% (w/v) sucrose, about 0.04% (w/v) polysorbate-20 and about 20 µg/ml EDTA at pH 6.5;
about 10 mg/ml cetrelimab, about 10 mM histidine, about 8.0% (w/v) sucrose, about 0.04% (w/v) polysorbate-20 and about 20 µg/ml EDTA at pH 6.5;
about 30 mg/ml cetrelimab, about 10 mM histidine, about 8.0% (w/v) sucrose, about 0.04% (w/v) polysorbate-20 and about 20 µg/ml EDTA at pH 6.5;
a lyophilized formulation comprising between about 90 mg and about 240 mg of cetrelimab and one or more pharmaceutically acceptable excipients;
a lyophilized formulation comprising about 90 mg of cetrelimab and one or more pharmaceutically acceptable excipients; or
a lyophilized formulation comprising about 240 mg of cetrelimab and one or more pharmaceutically acceptable excipients.

In some embodiments, the lyophilized formulation, once reconstituted, comprises about 30 mg/ml cetrelimab, about 10 mM histidine, about 8.0% (w/v) sucrose, about 0.04% (w/v) polysorbate-20 and about 20 µg/ml EDTA at pH 6.5.

In some embodiments, the lyophilized formulation is reconstituted into sterile water for injection (sWFI).

The invention also provides a drug product comprising about 10 mg/ml cetrelimab, about 10 mM histidine, about 8.0% (w/v) sucrose, about 0.04% (w/v) polysorbate-20 and about 20 µg/ml EDTA at pH 6.5 in a volume of about 3.3 ml.

The invention also provides a drug product comprising a lyophilized formulation comprising about 90 mg cetrelimab that upon reconstitution into about 3.3 ml comprises about 30 mg/ml cetrelimab, about 10 mM histidine, about 8.0% (w/v) sucrose, about 0.04% (w/v) polysorbate-20 and about 20 µg/ml EDTA at pH 6.5.

The invention also provides a drug product comprising a lyophilized formulation comprising about 240 mg cetrelimab that upon reconstitution into about 8.6 ml comprises about 30 mg/ml cetrelimab, about 10 mM histidine, about 8.0% (w/v) sucrose, about 0.04% (w/v) polysorbate-20 and about 20 µg/ml EDTA at pH 6.5.

The invention also provides a drug product comprising between about 10 mg/ml and about 30 mg/ml cetrelimab, about 10 mM histidine, about 8.0% (w/v) sucrose, about 0.04% (w/v) polysorbate-20 and about 20 µg/ml EDTA at pH 6.5;
about 10 mg/ml cetrelimab, about 10 mM histidine, about 8.0% (w/v) sucrose, about 0.04% (w/v) polysorbate-20 and about 20 µg/ml EDTA at pH 6.5;
about 30 mg/ml cetrelimab, about 10 mM histidine, about 8.0% (w/v) sucrose, about 0.04% (w/v) polysorbate-20 and about 20 µg/ml EDTA at pH 6.5;
a lyophilized formulation comprising between about 90 mg and about 240 mg of cetrelimab and one or more pharmaceutically acceptable excipients;
a lyophilized formulation comprising about 90 mg of cetrelimab and one or more pharmaceutically acceptable excipients; or
a lyophilized formulation comprising about 240 mg of cetrelimab and one or more pharmaceutically acceptable excipients,
for the treatment of a cancer.

In some embodiments, the lyophilized formulation, once reconstituted, comprises about 30 mg/ml cetrelimab, about 10 mM histidine, about 8.0% (w/v) sucrose, about 0.04% (w/v) polysorbate-20 and about 20 µg/ml EDTA at pH 6.5.

In some embodiments, the drug product is provided for the treatment of a lung cancer, a non-small cell lung cancer (NSCLC), a melanoma, a head and neck cancer, a bladder cancer, a gastrointestinal cancer, a gastric cancer, a gastroesophageal junction cancer, an esophageal cancer, a liver cancer, a colorectal cancer (CRC), a colon cancer, a gallbladder cancer, a biliary tract cancer, an ovarian cancer, a fallopian tube cancer, a cervical cancer, a peritoneal cancer, an endometrial cancer, a small cell lung cancer (SCLC), a breast cancer, a pancreatic cancer, a renal cell carcinoma, a liver cancer, a Merkel cell carcinoma, a primary mediastinal B-cell lymphoma (PMBCL), a Hodgkin's lymphoma, a non-Hodgkin's lymphoma, a large diffuse B-cell cell lymphoma (DLBLC), a multiple myeloma, a glioblastoma, an urothelial cancer, a salivary cancer, a mesothelioma, an anal cancer, a prostate cancer, a basal cell carcinoma and an advanced cutaneous squamous cell carcinoma (CSCC), or any combination thereof.

In some embodiments, the drug product is provided for the treatment of a NSCLC, a melanoma, a bladder cancer, a renal cell carcinoma, a SLCL, a CRC, a gastric cancer, a prostate cancer, or an esophageal cancer.

In some embodiments, the drug product is provided for the treatment of PD-L1 high NSCLC.

In some embodiments, the drug product is provided for the treatment of a MSI-H CRC or a dMMR CRC.

In some embodiments, the drug product is provided for the treatment of a non-uveal melanoma.

In some embodiments, the drug product is administered
at a dosage of about 240 mg once in two weeks;
at a dosage of about 480 mg once in four weeks; or
as an initial dose of about 240 mg followed by a second dose of about 480 mg six weeks
after the initial dose, and thereafter about 480 mg once in four weeks; or
as an initial dose of about 240 mg followed by a second dose of about 480 mg six weeks
after the initial dose, and thereafter about 240 mg once in two weeks.

In some embodiments, the drug product the drug product is administered by an intravenous administration of by a subcutaneous administration, or a combination thereof.

Generation of Antibodies Used in the Methods of the Invention

Antagonistic anti-PD-1 antibodies or antigen-binding fragments thereof used in the methods of the invention may be generated using various technologies. For example, the hybridoma method of Kohler and Milstein may be used to generate monoclonal antibodies. In the hybridoma method, a mouse or other host animal, such as a hamster, rat or monkey, is immunized with human and/or cyno PD-1 antigens, such as the extracellular domain of PD-1, followed by fusion of spleen cells from immunized animals with myeloma cells using standard methods to form hybridoma cells. Colonies arising from single immortalized hybridoma cells may be screened for production of antibodies with desired properties, such as specificity of binding, cross-reactivity or lack thereof, affinity for the antigen, and functionality such as antagonistic activity.

Exemplary humanization techniques including selection of human acceptor frameworks include CDR grafting (U.S. Pat. No. 5,225,539), SDR grafting (U.S. Pat. No. 6,818,749), Resurfacing (Padlan, (1991) *Mol Immunol* 28:489-499), Specificity Determining Residues Resurfacing (U.S. Patent Publ. No. 2010/0261620), human framework adaptation (U.S. Pat. No. 8,748,356) or superhumanization (U.S. Pat. No. 7,709,226). In these methods, CDRs or a subset of CDR residues of parental antibodies are transferred onto human frameworks that may be selected based on their overall homology to the parental frameworks, based on similarity in CDR length, or canonical structure identity, or a combination thereof.

Humanized antibodies may be further optimized to improve their selectivity or affinity to a desired antigen by incorporating altered framework support residues to preserve binding affinity (backmutations) by techniques such as those described in Int. Patent Publ. Nos. WO1090/007861 and WO 1992/22653, or by introducing variation at any of the CDRs for example to improve affinity of the antibody.

Transgenic animals, such as mice or rat carrying human immunoglobulin (Ig) loci in their genome may be used to generate antibodies against PD-1, and are described in for example U.S. Pat. No. 6,150,584, Int. Patent Publ. No. WO1999/45962, Int. Patent Publ. Nos. WO2002/066630, WO2002/43478, WO2002/043478 and WO1990/04036. The endogenous immunoglobulin loci in such animal may be disrupted or deleted, and at least one complete or partial human immunoglobulin locus may be inserted into the genome of the animal using homologous or non-homologous recombination, using transchromosomes, or using minigenes. Companies such as Regeneron (http://_www_regeneron_com), Harbour Antibodies (http://_www_harbourantibodies_com), Open Monoclonal Technology, Inc. (OMT) (http://_www_omtinc_net), KyMab (http://_www_kymab_com), Trianni (http://_www.trianni_com) and Ablexis (http:_www_ablexis_com) may be engaged to provide human antibodies directed against a selected antigen using technologies as described above.

Antibodies may be selected from a phage display library, where the phage is engineered to express human immunoglobulins or portions thereof such as Fabs, single chain antibodies (scFv), or unpaired or paired antibody variable regions. The antibodies of the invention may be isolated for example from phage display library expressing antibody heavy and light chain variable regions as fusion proteins with bacteriophage pIX coat protein as described in Shi et al., (2010) *J Mol Biol* 397:385-96, and Int. Patent Publ. No. WO09/085462). The libraries may be screened for phage binding to human and/or cyno PD-1 and the obtained positive clones may be further characterized, the Fabs isolated from the clone lysates, and expressed as full length IgGs.

The CDRs of an antibody may be grafted on any human framework and the functionality of the resulting antibody may be tested. For example, antibody JNJ-63723283 comprises frameworks derived from human germline genes IGHV1-69 and IGKV3-11. Alternatively, JNJ-63723283 HCDRs may be grafted to other IGHV1 germline gene subgroup frameworks and the LCDRs may be grafted to other IGKV3 germline gene subgroup frameworks and the resulting antibodies are tested for desired functionality. The human germline gene sequences are well known and can be retrieved for example from ImMunoGeneTics Information System®.

Preparation of immunogenic antigens and monoclonal antibody production may be performed using any suitable technique, such as recombinant protein production. The immunogenic antigens may be administered to an animal in the form of purified protein, or protein mixtures including whole cells or cell or tissue extracts, or the antigen may be formed de novo in the animal's body from nucleic acids encoding said antigen or a portion thereof.

Methods of Producing Antibodies

Methods of producing antibodies at large scales are known. Antibodies may be produced for example in CHO cells cultured using known methods. The antibody may be isolated and/or purified from culture medium by removing solids by centrifugation or filtering as a first step in the purification process. The antibody may be further purified by standard methods including chromatography (e.g., ion exchange, affinity, size exclusion, and hydroxyapatite chromatography), gel filtration, centrifugation, or differential solubility, ethanol precipitation or by any other available technique for the purification of antibodies. Protease inhibitors such as phenyl methyl sulfonyl fluoride (PMSF), leupeptin, pepstatin or aprotinin can be added at any or all stages to reduce or eliminate degradation of the antibody during the purification process. One of ordinary skill in the art will appreciate that the exact purification technique will vary depending on the character of the polypeptide or protein to be purified, the character of the cells from which the polypeptide or protein is expressed, and the composition of the medium in which the cells were grown.

The present invention will now be described with reference to the following specific, non-limiting examples.

Example 1. A First-in-Human, Open-Label, Phase 1/2 Study to Evaluate the Safety, Pharmacokinetics, Pharmacodynamics, and Clinical Activity of JNJ-63723283 (Cetrelimab), an Anti-PD-1 Monoclonal Antibody, in Subjects with Advanced Cancers (NCT02908906)

This is a first-in-human (FIH), Phase 1/2, open-label, multicenter study to establish RP2D(s) for JNJ-63723283 in Part 1 and to evaluate the safety and efficacy of the RP2D(s) in Part 2. Part 1 will consist of dosage escalation cohorts and pharmacokinetic/pharmacodynamic cohorts. In Part 2, 1 or more RP2D(s) determined in Part 1 will be evaluated in selected solid tumor types including NSCLC, melanoma, bladder cancer, renal cancer, small-cell lung cancer (SCLC), gastric/esophageal cancer, MSI-H or dMMR CRC, and thymoma (including thymic carcinoma). The overall safety of JNJ-63723283 will be assessed by the Safety Evaluation Team (SET). Subjects will continue to receive JNJ-63723283 until disease progression, unacceptable toxicity, withdrawal of consent, or end of study.

Primary Objective:
  To identify the recommended Phase 2 dosage(s) (RP2D[s]) for JNJ-63723283 (Part 1)
  To assess the anti-tumor activity of JNJ-63723283 at the RP2D(s) in subjects with selected advanced cancers including NSCLC, melanoma, renal, bladder, SCLC, gastric/esophageal cancer, high-level microsatellite instability (MSI-H) or mismatch repair-deficient (dMMR) colorectal cancer (CRC), and thymoma (Part 2)

Secondary Objectives:
  To characterize the safety of JNJ-63723283 in subjects with advanced solid tumors
  To characterize the pharmacokinetics of JNJ-63723283 administered intravenously
  To assess the immunogenicity of JNJ-63723283
  To assess the clinical activity of JNJ-63723283

Primary Endpoint(s)
  Frequency and severity of dosage-limiting toxicity (DLT)
  Overall response rate (ORR) per the Response Evaluation Criteria in Solid Tumors (RECIST) v1.1 in subjects with selected advanced solid tumors Secondary Endpoint(s)
  Safety profile of JNJ-63723283 (safety parameters include but are not limited to the frequency and severity of adverse events [AEs] and immune-related AEs [irAEs], vital signs measurements, clinical laboratory values, and electrocardiograms [ECGs])
  Serum JNJ-63723283 pharmacokinetic parameters including but not limited to maximum observed serum concentration (Cmax), area under the concentration-time curve between 2 defined sampling points, t1 and t2 (AUCt1-t2), half-life (T½), total systemic clearance of drug after IV administration (CL), volume of distribution at steady-state (Vss), and accumulation ratio (R)
  Presence of anti-JNJ-63723283 antibodies and effect on serum JNJ-63723283 concentrations
  ORR per the Immune-Related Response Criteria (irRC), duration of response (DOR), clinical benefit rate (CBR), and progression-free survival by both RECIST v.1.1 and irRC, and OS Exploratory:
  To characterize the pharmacodynamics of JNJ-63723283 including quantification of JNJ-63723283 receptor occupancy on peripheral T cells and cytokine responses to ex vivo stimulation of peripheral T cells
  To explore the relationships between pharmacokinetics, pharmacodynamics, AE profiles, and clinical activity of JNJ-63723283

Subject Population
  Subjects must be ≥18 years of age and have an Eastern Cooperative Oncology Group (ECOG) performance status score of 0 or 1. All subjects will have a histologically or cytologically confirmed solid tumor, except lymphoma, that is metastatic or unresectable, and had previously received or were ineligible for standard treatment options. In addition, subjects will not have received prior treatment with an anti-PD-1 or anti-PD-L1 antibody (i.e., anti-PD-1 and anti-PD-L1 naïve). In Part 2, subjects will have one of the following selected tumor types: PD-L1-high NSCLC, bladder, gastric/esophageal, melanoma, renal, SCLC, MSI-H or dMMR CRC.

Dosage and Administration
  The study drug will initially be administered via IV infusion once every 2 weeks. Dosage escalation will begin at the starting dosage of 80 mg and may continue at dosages 160 mg, 240 mg, 320 mg, 400 mg, 480 mg, 560 mg, 640 mg, 720 mg and 800 mg. The administration schedule and infusion duration may be changed based on emerging safety, pharmacokinetic, and pharmacodynamic/biomarker data, and as confirmed by the SET. In Part 1 alternative dosages and schedules may be explored (e.g., administration once every 3 weeks or every 4 weeks). One or more RP2D(s) for JNJ-63723283 may be evaluated in Part 2.

Safety Evaluations
  Safety will be assessed by physical examinations, ECOG performance status, clinical laboratory tests, vital signs, electrocardiograms, AE monitoring, and concomitant medication usage. Echocardiogram or multigated acquisition scans will be assessed at screening; subsequent evaluations will be conducted if clinically indicated. The severity of AEs will be assessed using National Cancer Institute Common Terminology Criteria for Adverse Events (NCI-CTCAE, Version 4).

Efficacy Evaluations
  Response to treatment will be assessed by the investigator according to RECIST v1.1 and irRC. Efficacy evaluations will include the following: computed tomography (CT) scans and/or magnetic resonance imaging (MRI), physical examination, and other procedures as necessary.

Statistical Methods
  The purpose of Part 1 is to identify the RP2D(s) in subjects with advanced solid tumors. Dosage escalation will be supported by a modified Continual Reassessment Method (mCRM) based on a statistical model, Bayesian Logistic Regression Model (BLRM), with Escalation with Overdosage Control (EWOC) principle. The total number of subjects treated will depend on the number of dosage levels explored and the number of subjects enrolled at each dosage level. In Part 2, it is hypothesized that the ORR of JNJ-63723283 per RECIST v1.1 administered at the RP2D(s) is at least 15% in subjects with selected solid tumors. The following are also hypothesized: 35% ORR for MSI-H/dMMR CRC, 30% ORR for PD-L1-high NSCLC, and 25% ORR for melanoma. The ORR of thymoma is for hypothesis-generating research. Interim monitoring for efficacy will be conducted.

Rationale for Pharmacokinetic and Immunogenicity Sampling
  Serum samples will be collected and analyzed in Part 1 and Part 2 for JNJ-63723283 concentrations, and estimation of basic pharmacokinetic parameters from this concentration-time data will be performed. Pharmacokinetics will be assessed relative to available clinical safety, pharmacodynamic, and efficacy data, as well as to any efficacious concentration thresholds observed in nonclinical or competitor studies. Pharmacokinetic or pharmacokinetic/pharmacodynamic analysis and modeling will be used to aid selection of a RP2D regimen for use in Part 2. Immunogenicity (i.e., ADA) will be evaluated for impact on pharmacokinetics and safety. The serum glycoform profile of JNJ-63723283 will also be characterized.

Rationale for Pharmacodynamic and Biomarker Sampling
  It is expected that JNJ-63723283 will induce phenotypic changes consistent with activation of T cells in peripheral blood and tumor tissues. Pharmacodynamic evaluations will be based on assessment of activation and proliferation markers as well as cytokine profiles of T cells in peripheral blood. Peripheral blood samples will also be used to quantify the response of the immune cells in ex vivo stimulation assays. As PD-1 polymorphisms could impact the effect of anti-PD-1 antibodies, PD-1 polymorphisms may be evaluated for possible correlation with clinical activity. JNJ-63723283 is anticipated to demonstrate binding to PD-1 on circulating immune cells following administration to human subjects. PD-1 receptor occupancy by JNJ-63723283 on circulating $CD3^+$ T cells will be measured using flow cytometry. Characteristics including dosage-dependence, peak occupancy, plateau occupancy, and duration of occupancy at plateau will be assessed, as feasible.

Rationale for PD-L1 Testing for Part 2
  Expression of PD-L1, the ligand for PD-1, correlates with enhanced clinical activity in multiple tumor types including NSCLC cancer. In Part 2, tumor tissue for PD-L1 testing will be required for all tumor types. This is necessary to correlate the clinical response with PD-L1 expression on the tumor tissue.

Rationale for MSI or dMMR Testing for Part 2
  Compared with other tumors, MSI-H and dMMR CRC has a higher frequency of DNA mutations and higher level of immune infiltrates, and thus is more susceptible to PD-1 blockade therapies. For the CRC group in Part 2, prescreening for MSI-H or dMMR is required.

Dosing
  The recommended FIH starting dosage regimen of JNJ-63723283 is 80 mg administered as an IV infusion every 2 weeks. Additional dosing intervals such as every 3 weeks, 4 weeks, or 6 weeks may be explored in Part 1 in addition to dosing every 2 weeks for further characterization of JNJ-63723283 pharmacology. The maximum administered dosage is planned to be 800 mg but may be lower or higher based on emerging data. Administered intravenously, initially over a 60 (±10) minute infusion. In the absence of infusion-related reactions, subsequent infusions may be administered intravenously over 30 (−5/+10) minutes. Longer infusion times may occur if the infusion needs to be paused or slowed due to a safety concern. Also, it is not recommended to administer ≥100 mL of diluted drug product faster than 30 (−5/+10) minutes, or ≥250 mL of diluted drug product faster than 60 (+10) minutes.

Inclusion Criteria

Each potential subject must satisfy all of the following criteria to be enrolled in the study:

1. ≥18 years of age
2. Have evaluable disease,
    2a. For Part 2, at least 1 measurable lesion that can be accurately assessed at baseline by CT (or magnetic resonance imaging [MRI] where CT is contraindicated) and is suitable for repeated assessment as per RECIST v1.1
3.2. Type of Cancer:

Part 1 of the Study:

Has any type of advanced or refractory solid tumor malignancy, except lymphoma, that is metastatic or unresectable and previously received or was ineligible for standard treatment options including appropriate molecularly targeted therapies (e.g., subjects with epidermal growth factor receptor [EGFR] mutant NSCLC or with NSCLC with anaplastic lymphoma tyrosine kinase [ALK] rearrangement).

Part 2 of the Study:

Histologically or cytologically confirmed diagnosis of 1 of the following unresectable Stage III or IV solid tumor malignancies and previously received or was ineligible for standard treatment options including appropriate molecularly targeted therapies (e.g., subjects with EGFR mutant NSCLC or with NSCLC with ALK rearrangement):

NSCLC
    PD-L1-high tumor sample (≥50% tumor cells stained positive for PD-L1) by a PD-L1 immunohistochemistry (IHC) test performed by a local laboratory or by the central laboratory designated by the sponsor
    Documented disease progression on or after at least 1 prior therapy with platinum-containing chemotherapy for advanced/metastatic NSCLC
    Have no more than 3 prior systemic regimens for the treatment of advanced NSCLC and have disease progression on or after last prior treatment (based on RECIST v1.1)

Bladder cancer (urothelial carcinoma)
Renal cell carcinoma
Gastric/esophageal carcinoma
Melanoma
SCLC
MSI-H or dMMR CRC
    MSI-H or dMMR by a polymerase chain reaction (PCR), next generation sequencing, or IHC test performed by a local laboratory or by the central laboratory designated by the sponsor
    Progressed following treatment with a fluoropyrimidine, oxaliplatin, and irinotecan 4. Have an Eastern Cooperative Oncology Group [ECOG] performance status 0 or 1

5.2. Have organ and bone marrow function as follows without blood product support:

Hemoglobin ≥8.5 g/dL, ANC≥1.5×109/L, Platelets ≥75.0×109/L, AST and ALT ≤3×ULN (or ≤4×ULN for subjects with tumor involvement in the liver), Total bilirubin ≤1.5×ULNa, Serum creatinine ≤1.5×ULN or a calculated GFR≥50 mL/min/1.73 mm2, Left ventricular ejection fraction Within normal institutional limits; Corrected QT interval (QTcF or QTcB)≤480 msec based on the average of triplicate assessments performed 5 (±3) minutes apart 6.1. Has thyroid function laboratory values within normal range. Note: If thyroid stimulating hormone (TSH) is not within normal limits, the subject may still be eligible if T3 (either total or free) and free T4 are within normal limits.

7. Women of childbearing potential must have a negative serum pregnancy test at Screening using highly sensitive pregnancy test.

8. Willing to use contraceptive methods consistent with local regulations for subjects participating in clinical studies during and after the study until 5 months after the last dosage of study drug.
    a. Women of childbearing potential must agree to use 2 highly effective methods of contraception consistent with local regulations (<1% per year failure rate when used consistently and correctly).
    b. A man who is sexually active with a woman of childbearing potential and has not had a vasectomy must agree to use a barrier method of birth control.
    c. Women and men must agree not to donate sperm or eggs (ova, oocytes), respectively, during the study and after the study until 5 months after the last dosage of study drug.

9. Willing and able to adhere to the prohibitions and restrictions specified in this protocol.

10. Each subject (or their legally acceptable representative) must sign an informed consent form (ICF) indicating that he or she understands the purpose of and procedures required for the study and are willing to participate in the study. Consent is to be obtained prior to the initiation of any study-related tests or procedures that are not part of standard of care for the subject's disease.

11. Subjects enrolled into Part 2 must have tumor tissue available for correlative studies. Fresh tumor biopsy is preferred. Archival tissue must meet the following criteria: archival sections within 4 months of sectioning that have been stored at 2° to 8° C. in the dark or archival tumor blocks within 5 years of collection. Subjects without tissues meeting the aforementioned archived tissue criteria must undergo a fresh biopsy.

Exclusion Criteria

Any potential subject who meets any of the following criteria will be excluded from participating in the study:

1. Has uncontrolled intercurrent illness, including but not limited to ongoing or active infection requiring IV antibiotics, symptomatic congestive heart failure (New York Heart Association class III-IV), unstable angina pectoris, cardiac arrhythmia, poorly controlled hypertension or diabetes, or psychiatric illness/social situation that would limited compliance with study requirements 2. Has had prior treatment with an anti-PD-1 antibody, anti-PD-L1 antibody or anti-PD-L2 antibody 3. Treatment with any local or systemic anti-neoplastic therapy, radiotherapy (excluding limited palliative radiation), or investigational anticancer agent within 14 days or 4 halflives, whichever is longer, up to a maximum wash-out period of 28 days prior to the initiation of study drug administration.

4. Criterion modified per Amendment 2

4.1. Has brain or leptomeningeal metastases unless asymptomatic, have been treated, have been stable for >4 weeks as documented by radiographic imaging with no evidence of cavitation or hemorrhage in the brain lesion, and do not require prolonged (>2 weeks) systemic corticosteroid therapy. Subjects are not permitted to receive enzyme-inducing antiepileptic drugs.

5. Has not recovered (i.e., ≤Grade 1 or baseline) from AEs except alopecia, peripheral neuropathy related to prior anti-cancer therapy and stable anemia (i.e., untransfused Hb≥8.5 g/dL without the need for supportive transfusion within 2 weeks of screening) at the time of treatment allocation 6. Criterion modified per Amendment 2

6.1. Has an active autoimmune disease or a documented history of autoimmune disease that requires systemic steroids or immunosuppressive agents.

Note: Subjects with vitiligo or resolved childhood asthma/atopy would be an exception to this rule. Subjects that require intermittent use of bronchodilators or local steroid injections would not be excluded from the study. Subjects with hypothyroidism stable on hormone replacement will not be excluded from the study. Subjects with a history of transient autoimmune manifestations of an acute infectious disease that resolved upon treatment of the infectious agent (e.g., acute Lyme arthritis) will not be excluded from the study.

7. Grade 3 or higher toxicity effects from previous treatment with immunotherapy 8. Known allergies, hypersensitivity, or intolerance to protein-based therapies or with a history of any significant drug allergy (such as anaphylaxis, hepatotoxicity, or immune-mediated thrombocytopenia or anemia), or to JNJ-63723283 excipients (refer to Investigator's Brochure)

9. Has taken immunosuppressive dosages of systemic medications, such as corticosteroids (dosages >10 mg/day prednisone or equivalent), within 2 weeks before the planned first dosage of study drug 10. A woman who is pregnant, breast-feeding, or planning to become pregnant while enrolled in this study or within 5 months after the last dosage of study drug 11. A man who plans to father a child while enrolled in this study or within 5 months after the last dosage of study drug.

12. Has any condition for which, in the opinion of the investigator, participation would not be in the best interest of the subject (e.g., compromise the well-being) or that could prevent, limit, or confound the protocol-specified assessments 13. Had major surgery (e.g., requiring general anesthesia) within 4 weeks before dosing, or will not have fully recovered from surgery, or has surgery planned during the time the subject is expected to participate in the study or within 4 weeks after the last dosage of study drug administration.

Note: Subjects with planned surgical procedures to be conducted under local anesthesia may participate 14. Criterion modified per Amendment 2

14.1. Active or chronic hepatitis B or hepatitis C disease as determined by hepatitis B surface antigen (HBsAg), hepatitis B core antibody, or hepatitis C antibody (anti-HCV) positivity at screening. If positive, further testing of quantitative levels to rule out active infection is required.

15. Has a history of human immunodeficiency virus (HIV) antibody positive, or tests positive for HIV at Screening 16. Criterion modified per Amendment 2

16.1. Vaccinated with a live vaccine within 28 days prior to the first dosage of study drug. Annual inactivated influenza vaccine is permitted.

NOTE: Investigators should ensure that all study enrollment criteria have been met at screening.

If a subject's clinical status changes (including any available laboratory results or receipt of additional medical records) after screening but before the first dosage of study drug is given such that he or she no longer meets all eligibility criteria, then the subject should be excluded from participation in the study.

Permitted Medications

Throughout the study, investigators may prescribe concomitant medications or treatments (including nutritional support, correction of metabolic disorders, optimal symptom control, and pain management) deemed necessary to provide adequate supportive care. Subjects may continue the use of bisphosphonates or denosumab for bone disease. Concurrent use of hormones for non-cancer related conditions (e.g., insulin for diabetes and hormone replacement therapy) is acceptable. Concomitant medications (e.g., acetaminophen/paracetamol or diphenhydramine) deemed necessary by the investigator to provide adequate prophylaxis and management of IRR are allowed.

In addition, the following medications may be administered during the study:

Standard supportive care therapies (antiemetics, antidiarrheals, anticholinergics, antispasmodics, antipyretics, antihistamines, analgesics, antibiotics and other anti-microbials, histamine receptor [H2] antagonists or proton pump inhibitors, and other medications intended to treat symptoms or signs of disease) as clinically indicated, according to institutional standards and as deemed necessary by the investigator.

Documented infectious complication should be treated with oral or IV antibiotics or other anti-infective agents as considered appropriate by the treating investigator for a given infectious condition, according to standard institutional practice.

Growth factor support for the management of treatment-emergent hematological toxicity as recommended according to National Comprehensive Cancer Network/European Organization for Research and Treatment of Cancer (NCCN/EORTC) guidelines.

Biomarkers

Tumor Tissue at Baseline

Available (archival or fresh) tumor tissue from consenting subjects will be requested from all subjects in Part 1 and required from all subjects in Part 2 for biomarker analysis of PD-L1 expression by IHC by the sponsor or sponsor's designee. Prescreening PD-L1 testing will be required for NSCLC subjects in Part 2 and may be performed by a local laboratory or by the central laboratory designated by the sponsor. For all CRC subjects, prescreening MSI or dMMR testing will also be required by a local laboratory or by the central laboratory designated by the sponsor. Local test results will be centrally confirmed by the sponsor's designee laboratory. In cases of discordance between local and central results, the central results will be used for analysis. Tumor tissue from the most recent tumor biopsy should be a formalin-fixed paraffin embedded (FFPE) tissue block that has been collected within the past 5 years (preferred) or a minimum of 15 unstained slides that have been processed no more than 4 months prior to study participation and have been stored at 2° C. to 8° C. in the dark. An additional 5 slides will be collected from CRC patients to support MSI-H analysis. If a site does not have sufficient material, a fresh tumor biopsy will be required for subjects in Part 2. Whole blood will be collected from CRC patients to support tumor tissue MSI and dMMR testing. This blood collection may be stopped due to developments in assay platforms utilized for MSI/dMMR testing.

Physical Description of Study Drug

Drug Product 1 (DP1): The JNJ-63723283 DP1 study material supplied for this study is a sterile, frozen liquid in an 8R glass vial with serum stopper and aluminum seal with flip-off cap. Each vial of JNJ-63723283 clinical study material is filled with 3.3 mL of a 10 mg/mL solution of JNJ-63723283 (including 10% overfill in 10 mM histidine, 8.0% (w/v) sucrose, 0.04% (w/v) polysorbate 20, 20 µg/ml EDTA, pH 6.5, e.g. 30 mg/vial deliverable amount).

Drug Product 2 (DP2): The JNJ-63723283 DP2 study material supplied for this study is a sterile, lyophilized formulation in an 8R glass vial with serum stopper and aluminum seal with flip-off cap. Each vial of JNJ-63723283 clinical study material contains 90 mg per vial that after reconstitution is a 30 mg/mL solution of JNJ-63723283 in 10 mM histidine, 8.0% (w/v) sucrose, 0.04% Polysorbate 20 (w/v/), 20 µg/ml. EDTA, pH 6.5.

DP3: JNJ-63723283 may also be supplied as a sterile, lyophilized formulation in an 30 mL glass vial with serum stopper and aluminum seal with flip-off cap. Each vial of JNJ-63723283 clinical study material contains 240 mg per vial that after reconstitution is a 30 mg/mL solution of JNJ-63723283 in 10 mM histidine, 8.0% (w/v) sucrose, 0.04% Polysorbate 20 (w/v), 20 µg/ml. EDTA, pH 6.5.

Example 2. Interim Results of a Phase 1/2 Study of JNJ-63723283 in Patients with Advanced Cancers (NCT02908906)

At a clinical data cutoff 11 Dec. 2017, 38 patients were treated with 80 mg, 240 mg, 460 mg or 800 mg of the study drug once every 2 weeks (Q2W), or 480 mg once every 4 weeks (Q4W) in part 1 of the study. Patient demographics and baseline disease characteristics for part 1 are show in Table 1. 12 (32%) patients remain on treatment, 26 (68%) have discontinued from study treatment (Table 2). Median duration of treatment was 51 days (range 1-297 days).

TABLE 1

| | Treatment group | | | | | |
| --- | --- | --- | --- | --- | --- | --- |
| | 80 mg | 240 mg | 460 mg | 480 mg | 800 mg | Total |
| Age, years | | | | | | |
| Median (range) | 49.5 | 59.0 | 53.0 | 56.5 | 45.5 | 53.5 |
| Sex, n (%) | | | | | | |
| Male | 4 (100) | 5 (31) | 2 (50) | 6 (60) | 3 (75) | 20 (53) |
| Female | 0 | 11 (69) | 2 (50) | 4 (40) | 1 (25) | 18 (47) |
| Race, n (%) | | | | | | |
| White | 4 (100) | 15 (94) | 4 (100) | 10 (100) | 2 (50) | 35 (92) |
| Black/African | 0 | 1 (6) | 0 | 0 | 0 | 1 (3) |
| Unknown | 0 | 0 | 0 | 0 | 2 (50) | 2 (5) |
| ECOG PS, n (%) | | | | | | |
| 0 | 3 (75) | 8 (50) | 2 (50) | 4 (40) | 3 (75) | 20 (53) |
| 1 | 1 (25) | 8 (50) | 2 (50) | 6 (60) | 1 (25) | 18 (47) |
| Cancer type, n (%) | | | | | | |
| NSCLC | 0 | 3 (19) | 1 (25) | 0 | 0 | 4 (10) |
| Renal cell | 0 | 0 | 1 (25) | 0 | 0 | 1 (3) |
| SCLC | 0 | 0 | 0 | 1 (10) | 0 | 1 (3) |
| Gastric/Esophageal | 0 | 2 (12) | 0 | 2 (20) | 0 | 4 (10) |
| Other | 4 (100) | 11 (69) | 2 (50) | 7 (70) | 4 (100) | 28 (74) |
| Prior lines of therapy, n | | | | | | |
| Median (range) | 2.5 | 3.5 | 2.0 | 2.0 | 3.5 | 3.0 |

TABLE 2

| Patients, n (%) | 80 mg Q2W (n = 4) | 240 mg Q2W (n = 16) | 460 mg Q2W (n = 4) | 480 mg Q4W (n = 10) | 800 mg Q2W (n = 4) | Total (N = 38) |
| --- | --- | --- | --- | --- | --- | --- |
| Ongoing treatment | 0 | 4 (25) | 1 (25) | 4 (40) | 3 (75) | 12 (32) |
| Discontinued treatment | 4 (100) | 12 (75) | 3 (75) | 6 (60) | 1 (25) | 26 (68) |
| Progressive disease | 4 (100) | 9 (56) | 3 (75) | 6 (60) | 0 | 22 (58) |
| Adverse event | 0 | 3 (19) | 0 | 0 | 0 | 3 (8) |
| Death | 0 | 0 | 0 | 0 | 1 (25) | 1 (3) |

Safety
  Dose Limiting Toxicity (DLT)
    240 mg Q2W: Grade 3 pleural effusion in a patient with NSCLC that required pleurodesis on study day 26 that was considered by the investigator to be possibly related to study drug because of the temporal relationship to study drug administration.
    800 mg Q2W: Grade 5 dyspnea in a patient with thymoma secondary to myasthenia gravis 14 days after receiving a single dosage of study drug.
  The most common AEs were anemia, fatigue, and vomiting (26% each; Table 3); the most common grade 3-4 AEs were pleural effusion, hyponatremia, anemia, and hypertension (8% each).
  Observed serious AEs included pleural effusion (10%) and dyspnea (8%).
    Immune-related AEs (irAEs) were reported in 37% of patients; most common irAEs were rash, hypothyroidism, and dyspnea (5% each).
    3 patients discontinued treatment due to possible/probable grade 3 treatment-related pneumonitis, myopathy, and alanine aminotransferase increased.

TABLE 3

| Patients, n (%) | 80 mg Q2W (n = 4) | 240 mg Q2W (n = 16) | 460 mg Q2W (n = 4) | 480 mg Q4W (n = 10) | 800 mg Q2W (n = 4) | Total (N = 38) |
|---|---|---|---|---|---|---|
| Any grade AE | 4 (100) | 16 (100) | 4 (100) | 10 (100) | 2 (50) | 36 (95) |
| Grade 3-4 AE | 2 (50) | 9 (56) | 2 (50) | 6 (60) | 0 | 19 (50) |
| ≥1 serious AE | 3 (75) | 11 (69) | 3 (75) | 6 (60) | 1 (25) | 24 (63) |
| ≥1 irAE | 1 (25) | 9 (56) | 1 (25) | 2 (20) | 1 (25) | 14 (37) |
| AEs occurring in ≥20% of patients | | | | | | |
| Anemia | 0 | 7 (44) | 1 (25) | 2 (20) | 0 | 10 (26) |
| Fatigue | 0 | 4 (25) | 2 (50) | 3 (30) | 1 (25) | 10 (26) |
| Vomiting | 2 (50) | 4 (25) | 1 (25) | 3 (30) | 0 | 10 (26) |
| Nausea | 0 | 5 (31) | 2 (50) | 2 (20) | 0 | 9 (24) |
| Diarrhea | 0 | 8 (50) | 0 | 0 | 1 (25) | 9 (24) |
| Hyponatremia | 2 (50) | 5 (31) | 0 | 1 (10) | 0 | 8 (21) |
| Hypertension | 3 (75) | 5 (31) | 0 | 0 | 0 | 8 (21) |
| Decreased appetite | 2 (50) | 4 (25) | 0 | 2 (20) | 0 | 8 (21) |
| Sinus tachycardia | 2 (50) | 5 (31) | 0 | 1 (10) | 0 | 8 (21) |

AE = adverse event;

irAE = immune-related adverse event;

Q2W = once every 2 weeks;

Q4W = once every 4 weeks

Preliminary Efficacy
  4 patients at the 240 mg Q2W dosage (NSCLC, gastric cancer, thymoma, and microsatellite unstable colon cancer) and 1 patient at the 480 mg Q4W dosage (gastric cancer) achieved a partial response (PR). Patient with thymoma had a delayed response 2 months after discontinuation from the study due to immune-mediated hepatitis. 18 (55%) response-evaluable patients achieved stable disease (SD) or better based on RECIST v1.1 (Table 4 shows the investigator-assessed best overall response.

TABLE 4

| Patients, n (%) | Treatment group | | | | |
|---|---|---|---|---|---|
| | 80 mg Q2W (n = 4) | 240 mg Q2W (n = 16) | 460 mg Q2W (n = 4) | 480 mg Q4W (n = 9) | Total (N = 33) |
| ORR (CR + PR) | 0 | 4 (25) | 0 | 1 (11) | 5 (15) |
| Best overall response | | | | | |
| CR | 0 | 0 | 0 | 0 | 0 |
| PR | 0 | 4 (25) | 0 | 1 (11) | 5 (15) |
| SD | 2 (50) | 8 (50) | 2 (50) | 1 (11) | 13 (39) |
| PD | 2 (50) | 4 (25) | 2 (50) | 6 (67) | 14 (42) |
| Unknown | 0 | 0 | 0 | 1 (11) | 1 (3) |

ORR = overall response rate;

CR = complete response;

PR = partial response;

SD = stable disease;

PD = progressive disease;

Q2W = once every 2 weeks;

Q4W = once every 4 weeks.

Figure 2:
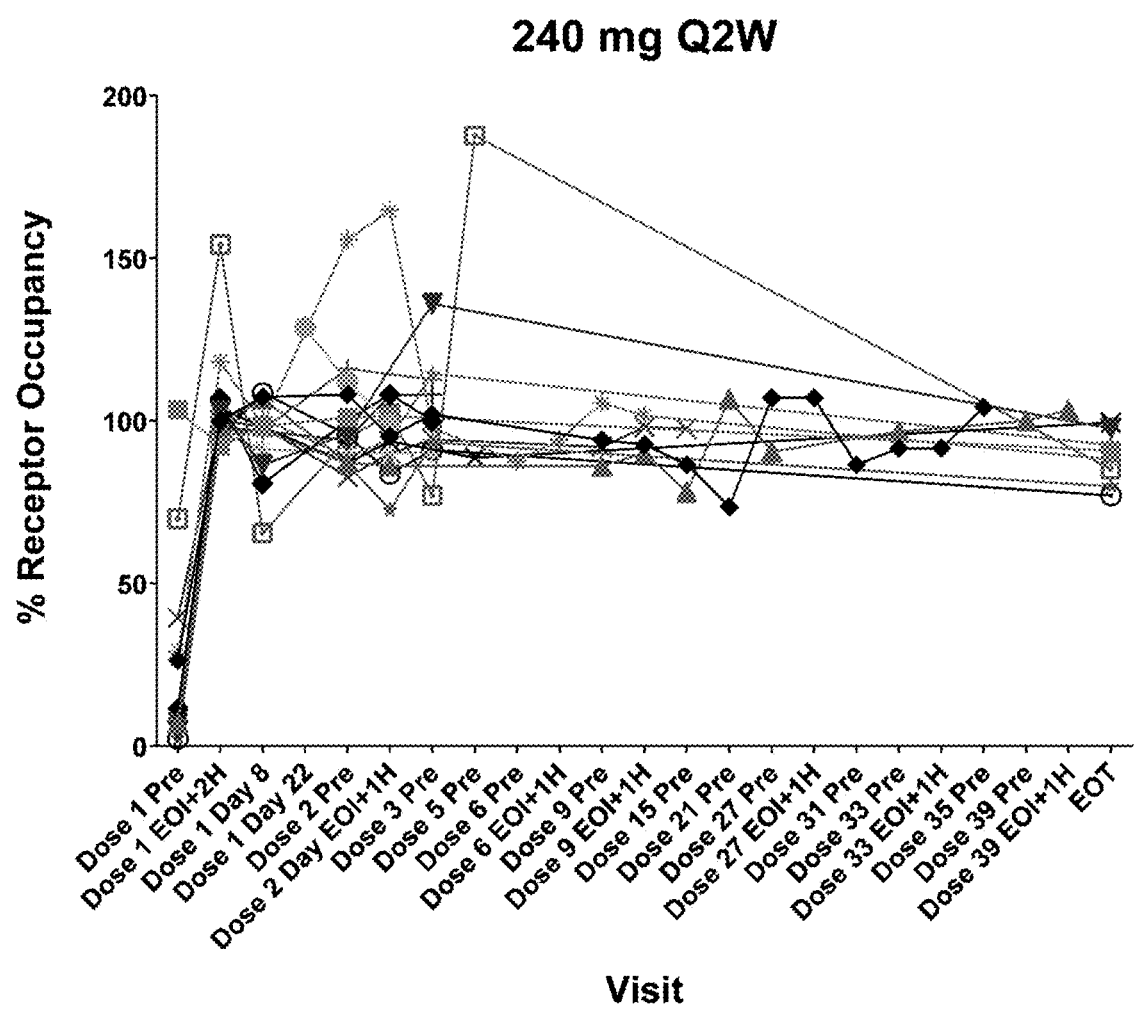
FIG. 2 shows the percentage (%) of PD-1 receptor occupancy of JNJ-63723283 (cetrelimab) on CD3+ circulating T cells over time (as indicated by administered doses 1-39) in subjects dosed 240 mg cetrelimab q2w. Pre: before dosing; EOI+2H: End of infusion plus 2 hours. EOI+1H: end of infusion plus 1 hour. EOT: end of treatment.
Figure 3:
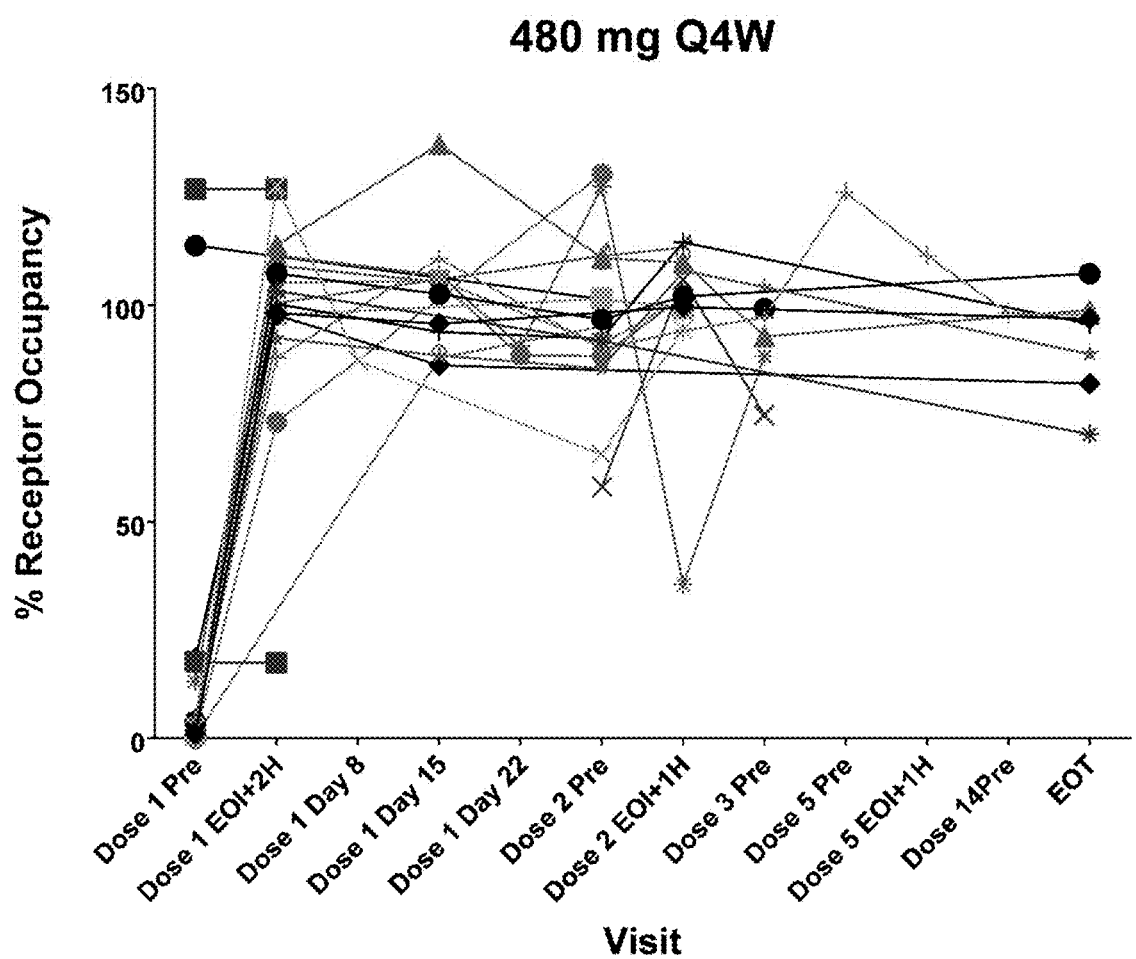
FIG. 3 shows the percentage (%) of PD-1 receptor occupancy of JNJ-63723283 (cetrelimab) on CD3+ circulating T cells over time (as indicated by administered doses 1-14) in subjects dosed 480 mg cetrelimab q4w. Pre: before dosing; EOI+2H: End of infusion plus 2 hours. EOI+1H: end of infusion plus 1 hour. EOT: end of treatment.

Pharmacokinetics and Receptor Occupancy
  Serum concentration of JNJ-63723283 in dosaged subjects were consistent with linear and dosage-proportional PK. Table 5 shows the preliminary PK parameters of JNJ-63723283 in patients dosaged 80 mg, 240 mg and 480 mg of JNJ-63723283 after the first dosage. FIG. 1 shows the mean serum concentration-time profiles of JNJ-63723283. Saturation of PD-1 receptors on circulating CD3$^+$ T cells was demonstrated after the first dosage and maintained throughout the dosing interval at all dosage levels (ranging from 80 mg to 480 mg) and all frequencies (ranging from Q2W to Q4W). The percentage (%) saturation of PD-1 receptors on circulating CD3$^+$ T cells is shown in FIG. 2. The percentage (%) saturation of PD-1 receptors on circulating CD3$^+$ T cells is shown in FIG. 3.

TABLE 5

| Dosage Level | n | $C_{max}$ (μg/mL) Mean (SD) | $T_{max}$ (hr) Median (range) | $C_{min1}$ (μg/mL) Mean (SD) | $AUC_{tau}{}^c$ (μg·hr/mL) Mean (SD) |
|---|---|---|---|---|---|
| 80 mg Q2W | 4 | 24.6 (3.57) | 2.0 (1.0-3.0) | 6.08 (0.65) | 3591 (156) |
| 240 mg Q2W[a] | 10[b] | 77.6 (18.4) | 1.0 (1.0-3.0) | 20.3 (5.2) | 11516 (2643) |
| 460 mg Q2W | 4 | 151.2 (7.4) | 2.0 (1.0-3.0) | 49.9 (1.2) | 24637 (4827) |
| 480 mg Q4W[d] | 9[e] | 171 (49.6) | 3.0 (1.0-7.0) | 30.1 (13.1) | 40493 (14379) |

[a]Pooled data from all patients in part 1 receiving 240 mg Q2W.
[b]n = 9 for $C_{min1}$ and $AUC_{tau}$;
[c]tau = 336 hr for the 80, 240, and 460 mg Q2W dosage groups; tau = 672 hr for the 480 mg Q4W dosage group.
[d]Pooled data from all patients in part 1 receiving 480 mg Q4W.
[e]n = 8 for $C_{min1}$ and $AUC_{tau}$.
$AUC_{tau}$ = area under the curve for 1 dosing interval;
$C_{max}$ = maximum serum concentration;
$C_{min1}$ = minimum serum concentration after the first dosage;
PK = pharmacokinetics;
Q2W = once every 2 weeks;
Q4W = once every 4 weeks;
SD = standard deviation;
$T_{max}$ = time to maximum serum concentration.

T Cell Functionality in Treated Patients

Figure 4:
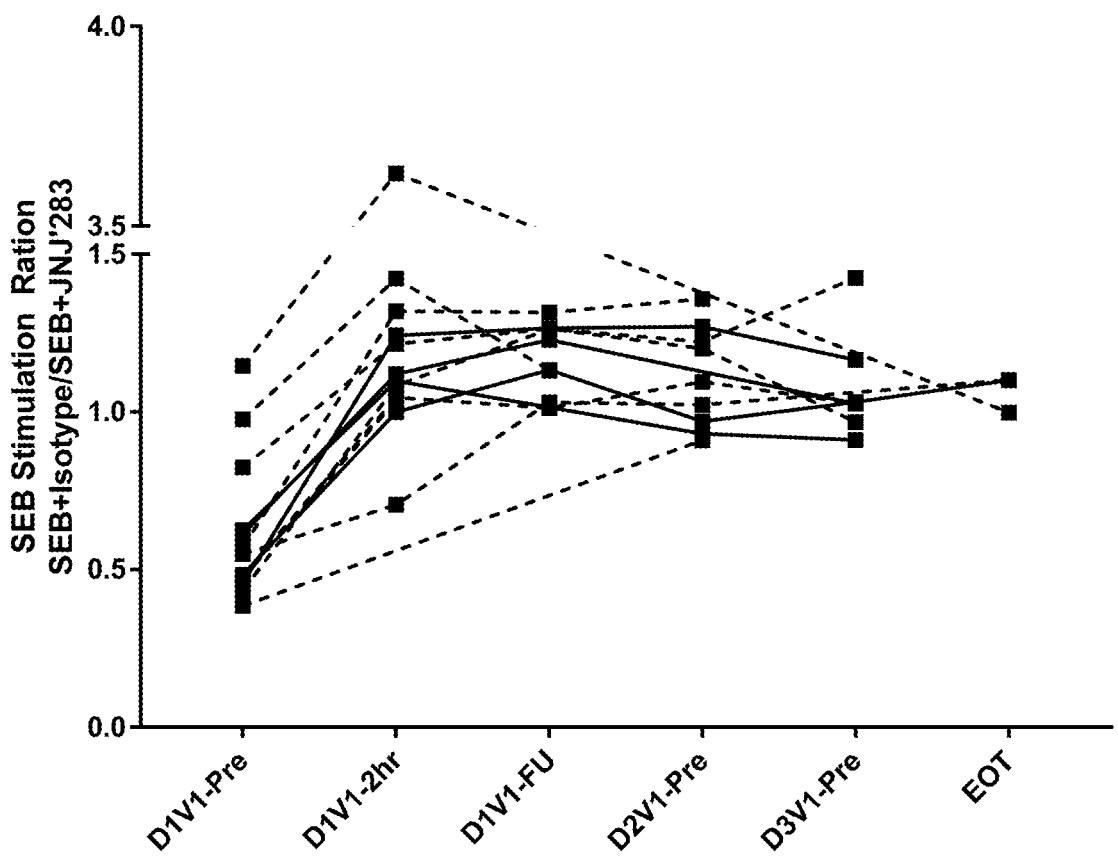
FIG. 4 shows the time course of T cell activation in patient receiving 240 mg once every two weeks (Q2W) (solid line) or 480 mg once every four weeks (Q4W) (dashed line) JNJ-63723283 (cetrelimab). Ratio of 1 indicates maximum T cell activation. D=dose; EOT=end of treatment (time points vary per patient); FU=follow-up; Pre=pre-infusion; Q2W=once every 2 weeks; Q4W=once every 4 weeks; SEB=staphylococcal enterotoxin B.

PBMCs from treated patients showed near maximal T cell activation in an ex vivo SEB stimulation assay at all dosages and time points tested. FIG. 4 shows the T cell activation in response to SEB prior to and 2 hours after dosage 1 (D1-Pre, D1-2 hr), at follow-up after dosage 1 (D1-FU), prior to dosage 2 (D2-Pre), prior to dosage 3 (D3-Pre) and at end of treatment (EOT) in patients who received 240 mg Q2W or 480 mg Q4Q of the antibody.

Methods: JNJ-63723283 pharmacodynamic modulation was characterized by evaluating IL-2 expression, as a measure of T cell activation, in pre- and post-treated ex vivo SEB (Staphylococcal enterotoxin B) stimulated whole blood samples. Briefly, blood samples were diluted 1:10 with RPMI 1640 media followed by a 4-day incubation with 100 ng/ml of SEB plus 10 μg/ml of JNJ-63723283 or isotype control, representing maximum and endogenous levels of IL-2 expression, respectively. The ratio of IL-2 expression levels between the isotype and JNJ-63723283 ex vivo treated blood samples was then calculated to assess the degree of PD modulation, with a ratio of 1 indicating maximum T cell activation.

Conclusions

JNJ-63723283 displayed a safety profile that was comparable to other anti-PD-1 antibodies.

The RP2D of 240 mg Q2W is being evaluated in phase 2; the RP2D may be administered at an alternative regimen of 480 mg Q4W to enable flexibility in various clinical settings.

Preliminary antitumor activity in patients with previously treated advanced cancers was observed, with 5 patients (15%) achieving a PR and 13 patients (39%) achieving SD.

JNJ-63723283 exhibited linear and dose-proportional PK within the dose range evaluated.

JNJ-63723283 demonstrated saturable PD-1 RO and enhanced T cell activity in ex-vivo SEB stimulation assays at all dose levels and throughout all dosing frequencies tested.

Additional dose levels and dosing frequencies may be explored.

The trial is ongoing to further characterize the safety, PK, and clinical activity of JNJ-63723283.

Example 3. Interim Results of a Phase 1/2 Study of JNJ-63723283 in Patients with Advanced Cancers (NCT02908906)

At a clinical data cutoff 4 Dec. 2018, 198 patients were treated with 80 mg, 240 mg, 460 mg or 800 mg of the study drug DP1 once every 2 weeks (Q2W), or 480 mg of the study drug DP1 or DP2 once every 4 weeks (Q4W) in part 1/2 of the study. Patient demographics and baseline disease characteristics for part 1 and part 2 subjects are shown in Table 6.

TABLE 6

| Total Number Of Subjects | NSCLC | Melanoma | Bladder | Renal Cell | SCLC | MSI-H/ dMMR | Gastric/ Esophageal | Other | Total |
|---|---|---|---|---|---|---|---|---|---|
| (N) | 35 | 50 | 4 | 2 | 11 | 47 | 16 | 33 | 198 |
| Sex (M:F) | 29:6 | 29:21 | 3:1 | 1:1 | 7:4 | 20:27 | 10:6 | 15:18 | 114:84 |
| ECOG | | | | | | | | | |
| 0 | 13 | 29 | 2 | 0 | 3 | 26 | 8 | 18 | 99 |
| 1 | 22 | 21 | 2 | 2 | 8 | 21 | 8 | 15 | 99 |
| No. Prior Regimens | | | | | | | | | |
| 0 | 0 | 13 | 0 | 0 | 0 | 0 | 0 | 0 | 13 |
| 1 | 18 | 12 | 1 | 1 | 5 | 2 | 3 | 5 | 47 |
| 2 | 12 | 15 | 2 | 0 | 4 | 20 | 6 | 8 | 67 |
| ≥3 | 5 | 10 | 1 | 1 | 2 | 25 | 7 | 20 | 71 |

TABLE 6-continued

| Total Number Of Subjects | NSCLC | Melanoma | Bladder | Renal Cell | SCLC | MSI-H/ dMMR | Gastric/ Esophageal | Other | Total |
|---|---|---|---|---|---|---|---|---|---|
| Grade at Screening | | | | | | | | | |
| Well Diff | 3 | 0 | 0 | 0 | 0 | 1 | 0 | 2 | 3 |
| Mod Diff | 2 | 0 | 0 | 0 | 0 | 15 | 1 | 2 | 18 |
| Poorly Diff | 5 | 0 | 2 | 1 | 1 | 10 | 3 | 1 | 18 |
| Other | 0 | 2 | 0 | 0 | 0 | 2 | 2 | 1 | 7 |
| N/A | 0 | 15 | 0 | 0 | 0 | 0 | 1 | 2 | 18 |
| Unknown | 25 | 33 | 2 | 1 | 10 | 19 | 9 | 25 | 99 |
| Stage at Screening | | | | | | | | | |
| II | | | | | | | | 1 | 1 |
| III | 2 | 1 | | | 1 | | | | 4 |
| IV | 33 | 42 | 4 | 2 | 10 | 43 | 15 | 26 | 142 |
| IVA | | 2 | | | | 0 | 1 | 3 | 6 |
| IVB | | 5 | | | | 4 | 0 | 3 | 12 |
| PDL1 | | | | | | | | | |
| Positive | 19 | 12 | | | | | | | 31 |
| Negative | 12 | 31 | | | | | | | 43 |
| Unknown | 4 | 7 | | | | | | | 11 |
| Ongoing Treatment | 15 | 22 | 0 | 1 | 1 | 22 | 1 | 5 | 67 |
| Discontinued Treatment | 20 | 28 | 4 | 1 | 10 | 25 | 15 | 28 | 131 |
| Treatment Duration Median (days) | 127 | 198 | 55 | 303 | 51 | 85 | 56.5 | 71 | 103 |
| Reason for Discontinuation | | | | | | | | | |
| AE | 2 | 3 | 0 | 0 | 0 | 5 | 0 | 2 | 12 |
| Death | 0 | 0 | 0 | 0 | 0 | 1 | 2 | 1 | 4 |
| WD by Subject | 0 | 0 | 0 | 0 | 0 | 1 | 0 | 1 | 2 |
| PD | 17 | 25 | 4 | 1 | 10 | 17 | 12 | 24 | 110 |
| Other | 1 | 0 | 0 | 0 | 0 | 1 | 1 | 0 | 3 |

Table 7 shows the mutation status, number and type of prior therapies for melanoma patients in Part 2. Table 8 shows the PD-L1 status, number and type of prior therapies for NSCLC patients in Part 2. Table 9 shows the MSI (Microsatellite Instability) status (Central testing result) in CRC.

TABLE 7

| Mutation status | |
|---|---|
| BRAF Mutation V600E: N (%) | 20 (46.5%) |
| BRAF Wildtype: N (%) | 18 (41.9%) |
| Number of Prior Therapies | |
| 0 | 13 (26.0%) |
| 1 | 12 (24.0%) |
| 2 | 15 (30.0%) |
| ≥3 | 10 (20.0%) |
| Type of Prior Therapies | |
| Ipilimumab: N (%) | 19 (38%) |
| BRAF/MEK: N (%) | 13 (26%) |
| Chemotherapy: N (%) | 18 (36%) |
| Interferon alpha: N (%) | 12 (24%) |

TABLE 8

| PDL1 status | Number of patients (percentage of patients)* |
|---|---|
| Positive | 19 (63.3%) |
| Negative | 11 (36.7%) |
| Number of Prior Therapies | |
| 0 | 0 |
| 1 | 16 (53.3%) |
| 2 | 11 (36.7%) |
| ≥3 | 3 (10.0%) |
| Type of Prior Therapies | |
| Ipilimumab: N (%) | 0 |
| BRAF/MEK: N (%) | 0 |
| Chemotherapy: N (%) | 29 (96.7%) |
| Interferon alpha: N (%) | 0 |

*percentages expressed as percent of NSCLC patients enrolled into Part 2

TABLE 9

| MSI Status (Central testing) | Number of patients (percentage of patients)* |
|---|---|
| Abnormal (High) | 19 (45.2%) |
| Normal | 12 (28.6%) |
| Other | 11 (26.2%) |

*Percentages expressed as percent of locally confirmed MSI-High/dMMR CRC patients enrolled into Part 2.

Safety
The most common TE-AEs (Treatment Emergent Adverse Events) reported were asthenia (22.2%), fatigue (19.2%), diarrhea (18.2%), dyspnoea (18.2%), pyrexia (17.7%), decreased appetite (16.7%), anaemia (16.7%), nausea (15.7%), back pain (14.1%), ALT increased (12.6%), cough (12.1%), vomiting (11.6%), AST increased (11.6%), abdominal pain (10.1%), constipation (10.1%).

The most common grade 3-4 TE-AEs reported were anaemia (6.6%), dyspnea (5.1%), pleural effusion (2.5%), pyrexia (5.1%), hyponatremia (3.0%), hyperamylasemia (2.5%), abdominal pain (2.5%), intestinal obstruction (2.5%), fatigue (2.5%), general physical health deterioration (2.5%), ALT increased (3.0%), AST increased (3.0%), GGT increased (3.0%), and hypertension (3.0%).

Serious TEAEs were observed in nearly 50% of subjects. The most common TE SAEs were dyspnoea (5.1%), pleural effusion (3.5%), intestinal obstruction (3.5%), general physical health deterioration (3.0%), and pyrexia (3.0%).

Immune-related AEs (irAEs) were reported in 35.9% of patients.

Infusion Related Reactions (IRRs) were reported in 14.1% of all subjects, and 13.6% in subjects receiving the 240 mg Q2W dose. All except 2 IRRs were CTCAE grade 1/2. Only 1 subject did not complete an infusion due to an IRR of a grade 3 hypertension event.

Table 10 shows the summary of the reported adverse events in part 1/2. Table 11 shows the adverse events occurring in >10% subjects.

TABLE 10

|  | 80 mg Q2W | 240 mg Q2W | 460 mg Q2W | 480 mg Q4W DP1 | 480 mg Q4W DP2 | 800 mg Q2W | Total |
|---|---|---|---|---|---|---|---|
| Number of Subjects | 4 | 162 | 4 | 11 | 11 | 6 | 198 |
| All TE-AEs | 4 (100.0%) | 150 (92.6%) | 4 (100.0%) | 11 (100.0%) | 10 (90.9%) | 6 (100.0%) | 185 (93.4%) |
| Grade 3 or higher TE-AEs | 2 (50.0%) | 79 (48.8%) | 2 (50.0%) | 7 (63.6%) | 5 (45.5%) | 5 (83.3%) | 100 (50.5%) |
| SAEs | 3 (75.0%) | 73 (45.1%) | 3 (75.0%) | 6 (54.5%) | 4 (36.4%) | 5 (83.3%) | 94 (47.5%) |
| Fatal TE-AEs | 0 | 0 | 0 | 0 | 0 | 1 (16.7%) | 1 (0.5%) |
| irAEs | 1 (25.0%) | 64 (39.5%) | 1 (25.0%) | 1 (9.1%) | 2 (18.2%) | 2 (33.3%) | 71 (35.9%) |
| Grade 3 or higher irAEs | 0 | 11 (6.8%) | 0 | 0 | 0 | 2 (33.3%) | 13 (6.6%) |
| IRR | 0 | 22 (13.6%) | 1 (25.0%) | 1 (9.1%) | 1 (9.1%) | 3 (50.0%) | 28 (14.1%) |
| Grade 3 or higher IRRs | 0 | 1 (0.6%) | 0 | 0 | 0 | 1 (16.7%) | 2 (1.0%) |

TE-AE: treatment emergent adverse events
SAE: serious adverse events
irAE: immune related TE-AEs
IRR: infusion related reactions

TABLE 11

|  | 80 mg N = 4 | 240 mg N = 162 | 460 mg N = 4 | 480 mg Q4W DP1, N = 11 | 480 mg Q4W DP2, N = 11 | 800 mg N = 6 | Total N = 198 |
|---|---|---|---|---|---|---|---|
| Subject with TEAEs Preferred Term* | 4 (100.0%) | 150 (92.6%) | 4 (100.0%) | 11 (100.0%) | 10 (90.9%) | 6 (100.0%) | 185 (93.4%) |
| Asthenia | 0 | 40 (24.7%) | 1 (25.0%) | 2 (18.2%) | 0 | 1 (16.7%) | 44 (22.2%) |
| Fatigue | 0 | 27 (16.7%) | 2 (50.0%) | 4 (36.4%) | 2 (18.2%) | 3 (50.0%) | 38 (19.2%) |
| Diarrhoea | 0 | 32 (19.8%) | 0 | 0 | 2 (18.2%) | 2 (33.3%) | 36 (18.2%) |
| Dyspnoea | 1 (25.0%) | 31 (19.1%) | 0 | 2 (18.2%) | 1 (9.1%) | 1 (16.7%) | 36 (18.2%) |
| Pyrexia | 0 | 31 (19.1%) | 0 | 2 (18.2%) | 1 (9.1%) | 1 (16.7%) | 35 (17.7%) |
| Decreased appetite | 2 (50.0%) | 27 (16.7%) | 0 | 2 (18.2%) | 2 (18.2%) | 0 | 33 (16.7%) |
| Anaemia | 0 | 26 (16.0%) | 1 (25.0%) | 3 (27.3%) | 1 (9.1%) | 2 (33.3%) | 33 (16.7%) |
| Nausea | 0 | 25 (15.4%) | 2 (50.0%) | 2 (18.2%) | 1 (9.1%) | 1 (16.7%) | 31 (15.7%) |

TABLE 11-continued

| | 80 mg N = 4 | 240 mg N = 162 | 460 mg N = 4 | 480 mg Q4W DP1, N = 11 | 480 mg Q4W DP2, N = 11 | 800 mg N = 6 | Total N = 198 |
|---|---|---|---|---|---|---|---|
| Back pain | 0 | 22 (13.6%) | 0 | 3 (27.3%) | 2 (18.2%) | 1 (16.7%) | 28 (14.1%) |
| Alanine aminotransferase increased | 1 (25.0%) | 22 (13.6%) | 0 | 0 | 1 (9.1%) | 1 (16.7%) | 25 (12.6%) |
| Cough | 1 (25.0%) | 22 (13.6%) | 0 | 0 | 1 (9.1%) | 0 | 24 (12.1%) |
| Vomiting | 2 (50.0%) | 15 (9.3%) | 1 (25.0%) | 3 (27.3%) | 1 (9.1%) | 1 (16.7%) | 23 (11.6%) |
| Aspartate aminotransferase increased | 1 (25.0%) | 19 (11.7%) | 0 | 1 (9.1%) | 1 (9.1%) | 1 (16.7%) | 23 (11.6%) |
| Abdominal pain | 1 (25.0%) | 14 (8.6%) | 0 | 3 (27.3%) | 0 | 2 (33.3%) | 20 (10.1%) |
| Constipation | 0 | 11 (6.8%) | 2 (50.0%) | 3 (27.3%) | 4 (36.4%) | 0 | 20 (10.1%) |

*Occurring in >10% subjects, All treated subjects (N = 198)
TEAE: Treatment Emergent Adverse Event Preliminary Efficacy Observed in Part 2 Subjects.

140 patients at the 240 mg Q2W dosage (NSCLC, melanoma, and MSI-H/dMMR CRC) were evaluable for response evaluation based on 4 Dec. 2018 dataset. 4 (2.9%) patients achieved a complete response (CR) and 23 (16.4%) achieved a partial response (PR). 73 (52.1%) response-evaluable patients achieved stable disease (SD) or better based on RECIST v1.1. The following ORRs were observed by histologic subtype: 37.5% in PDL1+≥50% NSCLC, 32.6% in non-uveal melanoma, and 12.5% in MSI-H/dMMR CRC. In patients with centrally confirmed MSI-H CRC, the ORR increased to 16.7%. (Table 12 shows the investigator-assessed best overall response and associated 80% confidence intervals.)

TABLE 12

| | Treatment Group | | | | | |
|---|---|---|---|---|---|---|
| | NSCLC (Unselected) | NSCLC (PDL1+ ≥50%) | Melanoma | Melanoma (excluding Uveal) | CRC | All Part 2 |
| N | 27 | 16 | 49 | 43 | 40 | 140 |
| ORR: N (%) | 7 (25.9%) | 6 (37.5%) | 14 (28.6%) | 14 (32.6%) | 5 (12.5%) | 27 (19.3%) |
| 80% CI | (15.1-39.7) | (21.0-56.5) | (20.1-38.4) | (23.1-43.4) | (6.2-22.0) | |
| Confirmed ORR | 5 (18.5%) | 4 (25%) | 13 (26.5%) | 13 (30.2%) | 3 (7.5%) | 22 (15.7%) |
| 80% CI | (9.3-31.7) | (11.4-43.9) | (18.3-36.3) | (21.0-40.9) | (2.8-15.9) | |
| DCR (CR + PR + SD) 80% CI | 18 (66.7%) (52.5-78.8) | | 32 (65.3%) (55.2-74.4) | 32 (74.4%) | 19 (47.5%) (36.4-58.8) | 73 (52.1%) |
| Best Response | | | | | | |
| CR | 0 | | 4 (8.2%) | 4 (9.3%) | 0 (0%) | 4 (2.9%) |
| PR | 7 (25.9%) | | 10 (20.4%) | 10 (23.3%) | 5 (12.5%) | 23 (16.4%) |
| SD | 11 (40.7%) | | 18 (36.7%) | 18 (41.9%) | 14 (35.0%) | 46 (32.9%) |
| PD | 9 (33.3%) | | 17 (34.7%) | 11 (25.6%) | 21 (52.5%) | 67 (47.9%) |

ORR = overall response rate;
CR = complete response;
PR = partial response;
SD = stable disease;
PD = progressive disease;
CI = Confidence Interval Conclusions
- JNJ-63723283 displayed a safety profile in immune-sensitive advanced cancers that was comparable to other anti-PD-1 antibodies.
- JNJ-63723283 exhibited linear and dose-proportional PK within the dose range evaluated.
- JNJ-63723283 demonstrated saturable PD-1 RO and enhanced T cell activity in ex-vivo SEB stimulation assays at all dose levels and throughout all dosing frequencies tested.
- The RP2D of 240 mg Q2W is being evaluated in phase 2; the RP2D may be administered at an alternative regimen of 480 mg Q4W to enable flexibility in various clinical settings.
- Additional dose levels, administration routes (subcutaneous injection), and dosing frequencies may be explored.
- Patients with advanced cancers achieved an ORR of 19% overall; by histologic subtype, observed ORRs were 37.5% in PDL1+NSCLC, 32.6% in non-uveal melanoma, and 13% in MSI-H/dMMR.
- Follow-up is ongoing on the centrally confirmed MSI-H CRC cohort
- The trial is ongoing to further characterize the safety, PK, and clinical activity of JNJ-63723283 at the RP2D of 240 mg Q2W.

---

We claim:

1. A method of treating a cancer, comprising administering to a subject diagnosed with the cancer a dose of between about 240 mg and about 480 mg of an antagonistic human anti-PD-1 antibody or an antigen binding fragment thereof that comprises
   a heavy chain of SEQ ID NO: 9 and a light chain of SEQ ID NO: 10, thereby treating the cancer,
   wherein the cancer is a solid tumor that is metastatic or unresectable.

2. The method of claim 1, wherein the antagonistic anti-PD-1 antibody or the antigen binding fragment thereof is administered once every two weeks, once every three weeks, once every four weeks, once every five weeks or once every six weeks.

3. The method of claim 1, wherein the antagonistic anti-PD-1 antibody or the antigen binding fragment thereof is administered a) at a dosage of about 240 mg once every two weeks, once every three weeks, once every four weeks, once every five weeks or once every six weeks;
b) at the dosage of about 240 mg once every two weeks;
c) at the dosage of about 240 mg once every three weeks;
d) at the dosage of about 240 mg once every four weeks;
e) at the dosage of about 240 mg once every five weeks;
f) at the dosage of about 240 mg once every six weeks;
g) at a dosage of about 480 mg once every two weeks, once every three weeks, once every four weeks, once every five weeks or once every six weeks;
h) at the dosage of about 480 mg once every two weeks;
i) at the dosage of about 480 mg once every three weeks;
j) at the dosage of about 480 mg once every four weeks;
k) at the dosage of about 480 mg once every five weeks; or
l) at the dosage of about 480 mg once every six weeks.

4. The method of claim 3, wherein the cancer is selected from the group consisting of a lung cancer, a non-small cell lung cancer (NSCLC), a melanoma, a head and neck cancer, a bladder cancer, a gastrointestinal cancer, a gastric cancer, a gastro-esophageal junction cancer, an esophageal cancer, a liver cancer, a colorectal cancer (CRC), a colon cancer, a gallbladder cancer, a biliary tract cancer, an ovarian cancer, a fallopian tube cancer, a cervical cancer, a peritoneal cancer, an endometrial cancer, a small cell lung cancer (SCLC), a breast cancer, a pancreatic cancer, a renal cell carcinoma, a liver cancer, a Merkel cell carcinoma, a primary mediastinal B-cell lymphoma (PMBCL), a Hodgkin's lymphoma, a non-Hodgkin's lymphoma, a large diffuse B-cell cell lymphoma (DLBLC), a multiple myeloma, a glioblastoma, an urothelial cancer, a salivary cancer, a mesothelioma, an anal cancer, a prostate cancer, a basal cell carcinoma and an advanced cutaneous squamous cell carcinoma (CSCC), or any combination thereof.

5. The method of claim 4, wherein the subject is PD-1 axis naïve.

6. The method of claim 4, wherein the subject has received one, two, three or more prior therapeutics to treat the cancer.

7. The method of claim 6, wherein the one, two, three or more prior therapeutics to treat the cancer are an anti-CTLA4 antibody, ipilimumab, BRAF/MEK inhibitor, chemotherapy or interferon alpha, or any combination thereof.

8. The method of claim 6, wherein the subject is resistant, refractory or resistant and refractory to the one, two, three or more prior therapeutics to treat the cancer, or any combination thereof.

9. The method of claim 8, wherein the one, two, three or more prior therapeutics to treat the cancer are an anti-CTLA4 antibody, ipilimumab, BRAF/MEK inhibitor, chemotherapy or interferon alpha, or any combination thereof.

10. The method of claim 4, wherein the cancer is PD-L1 positive.

11. The method of claim 10, wherein the cancer is PD-L1 high.

12. The method of claim 4, wherein PD-L1 expression in the cancer is undetermined.

13. The method of claim 4, wherein the cancer expresses a mutant BRAF.

14. The method of claim 13, wherein the mutant BRAF comprises a V600E mutation.

15. The method of claim 4, wherein the cancer expresses a wild-type BRAF.

16. The method of claim 4, wherein the antagonistic anti-PD-1 antibody or the antigen binding fragment thereof is
a) administered or provided for administration in a pharmaceutical composition comprising between about 10 mg/ml to about 30 mg/ml of the antagonistic anti-PD-1 antibody or the antigen binding fragment thereof, about 10 mM histidine, about 8.0% (w/v) sucrose, about 0.04% (w/v) polysorbate-20 and about 20 ug/ml EDTA at pH 6.5;
b) administered or provided for administration in a pharmaceutical composition comprising about 10 mg/ml of the antagonistic anti-PD-1 antibody or the antigen binding fragment thereof, about 10 mM histidine, about 8.0% (w/v) sucrose, about 0.04% (w/v) polysorbate-20 and about 20 ug/ml EDTA at pH 6.5;
c) administered or provided for administration in a pharmaceutical composition comprising about 30 mg/ml of the antagonistic anti-PD-1 antibody or the antigen binding fragment thereof, about 10 mM histidine, about 8.0% (w/v) sucrose, about 0.04% (w/v) polysorbate-20 and about 20 ug/ml EDTA at pH 6.5;
d) provided for administration as a lyophilized formulation comprising between about 90 mg and about 240 mg of the antagonistic anti-PD-1 antibody or the antigen binding fragment thereof and one or more pharmaceutically acceptable excipients;
e) provided for administration as a lyophilized formulation comprising about 90 mg of the antagonistic anti-PD-1 antibody or the antigen binding fragment thereof and one or more pharmaceutically acceptable excipients; or
f) provided for administration as a lyophilized formulation comprising about 240 mg of the antagonistic anti-PD-1 antibody or the antigen binding fragment thereof and one or more pharmaceutically acceptable excipients.

17. The method of claim 16, wherein the lyophilized formulation of d), e) and/or f), once reconstituted, comprises about 30 mg/ml of the antagonistic anti-PD-1 antibody or the antigen binding fragment thereof, about 10 mM histidine, about 8.0% (w/v) sucrose, about 0.04% (w/v) polysorbate-20 and about 20 ug/ml EDTA at pH 6.5.

18. The method of claim 4, wherein the antagonistic anti-PD-1 antibody or the antigen binding fragment thereof is administered by an intravenous infusion.

19. The method of claim 4, wherein the antagonistic anti-PD-1 antibody or the antigen binding fragment thereof is administered by a subcutaneous injection.

20. The method of claim 4, wherein the method achieves an overall response rate (ORR) of at least about 15% in a group of subjects diagnosed with the cancer.

21. The method of claim 20, wherein the ORR of at least about 15% is achieved after a median duration of treatment of about 1 ½ months or more.

22. The method of claim 20, wherein the method achieves an ORR of at least about 19% in the group of subjects diagnosed with the cancer.

23. The method of claim 4, wherein the cancer is the non-small cell lung cancer (NSCLC).

24. The method of claim 23, wherein the method achieves an ORR of at least about 30% in a group of subjects diagnosed with PD-L1 high NSCLC or an ORR of at least about 25% in a group of subjects whose PD-L1 expression in the cancer is undetermined.

25. The method of claim 24, wherein the method achieves an ORR of at least about 35% in the group of subjects diagnosed with PD-L1 high NSCLC.

26. The method of claim 4, wherein the cancer is the melanoma.

27. The method of claim 26, wherein the method achieves an ORR of at least about 25% in a group of subjects diagnosed with the melanoma.

28. The method of claim 27, wherein the melanoma is a non-uveal melanoma.

29. The method of claim 28, wherein the method achieves an ORR of at least about 30% in a group of subjects diagnosed with the non-uveal melanoma.

30. The method of claim 4, wherein the CRC is a microsatellite instability-high (MSI-H) CRC or a mismatch repair-deficient (dMMR) CRC, or a combination thereof.

31. The method of claim 30, wherein the CRC is a stage II CRC or a stage III CRC.

32. The method of claim 1, wherein administration of the anti-PD-1 antibody at a dosage of from about 240 mg to about 480 mg results in decreased grade three or higher adverse events compared to administration of the anti-PD-1 antibody at a dosage of 800 mg.

33. The method of claim 1, wherein administration of the anti-PD-1 antibody at a dosage of from about 240 mg to about 480 mg results in an increased response rate compared to administration of the anti-PD-1 antibody at a dosage 80 mg).

34. A method of treating a cancer, comprising administering to a subject diagnosed with the cancer a dose of between about 240 mg and about 480 mg of an antagonistic human anti-PD-1 antibody or an antigen binding fragment thereof that comprises
    a heavy chain of SEQ ID NO: 9 and a light chain of SEQ ID NO: 10,
    thereby treating the cancer,
    wherein the subject has previously received or was ineligible for standard treatment options.

\* \* \* \* \*

SEQUENCE LISTING

```
<160> NUMBER OF SEQ ID NOS: 11

<210> SEQ ID NO 1
<211> LENGTH: 5
<212> TYPE: PRT
<213> ORGANISM: Artificial Sequence
<220> FEATURE:
<223> OTHER INFORMATION: antibody HCDR1

<400> SEQUENCE: 1

Ser Tyr Ala Ile Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Antibody HCDR2

<400> SEQUENCE: 2

Gly Ile Ile Pro Ile Phe Asp Thr Ala Asn Tyr Ala Gln Lys Phe Gln
1               5                   10                  15

Gly

<210> SEQ ID NO 3
<211> LENGTH: 14
<212> TYPE: PRT
<213> ORGANISM: Artificial Sequence
<220> FEATURE:
<223> OTHER INFORMATION: Antibody HDR3

<400> SEQUENCE: 3

Pro Gly Leu Ala Ala Ala Tyr Asp Thr Gly Ser Leu Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Antibody LCDR1

<400> SEQUENCE: 4

Arg Ala Ser Gln Ser Val Arg Ser Tyr Leu Ala
1               5                   10

<210> SEQ ID NO 5
<211> LENGTH: 7
<212> TYPE: PRT
<213> ORGANISM: Artificial Sequence
```

-continued

```
<220> FEATURE:
<223> OTHER INFORMATION: Antibody LCDR2

<400> SEQUENCE: 5

Asp Ala Ser Asn Arg Ala Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Antibody LCDR3

<400> SEQUENCE: 6

Gln Gln Arg Asn Tyr Trp Pro Leu Thr
1               5

<210> SEQ ID NO 7
<211> LENGTH: 123
<212> TYPE: PRT
<213> ORGANISM: Artificial Sequence
<220> FEATURE:
<223> OTHER INFORMATION: Antibody VH

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Asp Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Leu Ala Ala Ala Tyr Asp Thr Gly Ser Leu Asp Tyr
            100                 105                 110

Trp Gly Gln Gly Thr Leu Val Thr Val Ser Ser
        115                 120

<210> SEQ ID NO 8
<211> LENGTH: 107
<212> TYPE: PRT
<213> ORGANISM: Artificial Sequence
<220> FEATURE:
<223> OTHER INFORMATION: Antibody VL

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80
```

-continued

Glu Asp Phe Ala Val Tyr Tyr Cys Gln Gln Arg Asn Tyr Trp Pro Leu
                85                  90                  95

Thr Phe Gly Gln Gly Thr Lys Val Glu Ile Lys
            100                 105

<210> SEQ ID NO 9
<211> LENGTH: 450
<212> TYPE: PRT
<213> ORGANISM: Artificial Sequence
<220> FEATURE:
<223> OTHER INFORMATION: Antibody HC

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Asp Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Gly Leu Ala Ala Tyr Asp Thr Gly Ser Leu Asp Tyr
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

```
Lys Thr Ile Ser Lys Ala Lys Gly Gln Pro Arg Glu Pro Gln Val Tyr
            340                 345                 350

Thr Leu Pro Pro Ser Gln Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
                420                 425                 430

Glu Ala Leu His Asn His Tyr Thr Gln Lys Ser Leu Ser Leu Ser Leu
            435                 440                 445

Gly Lys
    450

<210> SEQ ID NO 10
<211> LENGTH: 214
<212> TYPE: PRT
<213> ORGANISM: Artificial Sequence
<220> FEATURE:
<223> OTHER INFORMATION: Antibody LC

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Arg Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Tyr Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
```

```
<211> LENGTH: 268
<212> TYPE: PRT
<213> ORGANISM: Homo sapiens

<400> SEQUENCE: 11

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
130                 135                 140

Gln Phe Gln Thr Leu Val Val Gly Val Val Gly Gly Leu Leu Gly Ser
145                 150                 155                 160

Leu Val Leu Leu Val Trp Val Leu Ala Val Ile Cys Ser Arg Ala Ala
                165                 170                 175

Arg Gly Thr Ile Gly Ala Arg Arg Thr Gly Gln Pro Leu Lys Glu Asp
            180                 185                 190

Pro Ser Ala Val Pro Val Phe Ser Val Asp Tyr Gly Glu Leu Asp Phe
        195                 200                 205

Gln Trp Arg Glu Lys Thr Pro Glu Pro Pro Val Pro Cys Val Pro Glu
    210                 215                 220

Gln Thr Glu Tyr Ala Thr Ile Val Phe Pro Ser Gly Met Gly Thr Ser
225                 230                 235                 240

Ser Pro Ala Arg Arg Gly Ser Ala Asp Gly Pro Arg Ser Ala Gln Pro
                245                 250                 255

Leu Arg Pro Glu Asp Gly His Cys Ser Trp Pro Leu
            260                 265
```